US010895576B2

(12) United States Patent
Gatto et al.

(10) Patent No.: US 10,895,576 B2
(45) Date of Patent: Jan. 19, 2021

(54) CANCER BIOMARKERS

(71) Applicant: Elypta AB, Stockholm (SE)

(72) Inventors: Francesco Gatto, San Diego, CA (US); Jens Nielsen, Gothenburg (SE)

(73) Assignee: ELYPTA AB, Stockholm (SE)

( * ) Notice: Subject to any disclaimer, the term of this patent is extended or adjusted under 35 U.S.C. 154(b) by 0 days.

(21) Appl. No.: 15/451,840

(22) Filed: Mar. 7, 2017

(65) Prior Publication Data

US 2017/0254811 A1 Sep. 7, 2017

Related U.S. Application Data

(60) Provisional application No. 62/304,734, filed on Mar. 7, 2016.

(30) Foreign Application Priority Data

Aug. 5, 2016 (GB) .................................. 1613539.4

(51) Int. Cl.
| | |
|---|---|
| G01N 33/574 | (2006.01) |
| G01N 33/50 | (2006.01) |
| C12Q 1/6886 | (2018.01) |
| A61K 31/44 | (2006.01) |
| A61K 31/404 | (2006.01) |
| A61K 31/436 | (2006.01) |
| A61K 31/4439 | (2006.01) |
| A61K 31/506 | (2006.01) |

(52) U.S. Cl.
CPC ..... *G01N 33/57438* (2013.01); *A61K 31/404* (2013.01); *A61K 31/436* (2013.01); *A61K 31/44* (2013.01); *A61K 31/4439* (2013.01); *A61K 31/506* (2013.01); *C12Q 1/6886* (2013.01); *G01N 33/50* (2013.01); *C12Q 2600/118* (2013.01); *C12Q 2600/158* (2013.01); *G01N 2800/52* (2013.01)

(58) Field of Classification Search
CPC .......... G01N 2800/50; G01N 2800/52; G01N 2800/56; G01N 2800/60; G01N 2800/7023; G01N 2800/7028; G01N 2800/7071; G01N 33/66; A61B 5/4842; A61B 5/4848; A61B 5/4836; A61B 5/4839
See application file for complete search history.

(56) References Cited

PUBLICATIONS

Ucakturn, E. et al. "Capillary electrophoresis for total glycosaminoglycan analysis." Anal. Bioanal. Chem. (2014) 19 4617-4626. (Year: 2014).*
Kim et al., "Urine Metabolomic Analysis Identifies Potential Biomarkers and Pathogenic Pathways in Kidney Cancer", OMICS: A Journal of Integrative Biology, 15(5):293-303 (2011).
Lin et al., "LC-MS based serum metabonomic analysis for renal cell carcinoma diagnosis, staging, and biomarker discovery", Journal of Proteome Research, 10:1396-1405 (2011).
Lin et al., "LC-MS-based serum metabolic profiling for genitourinary cancer classification and cancer type-specific biomarker discovery", Proteomics, 12:2238-2246 (2012).
Zira et al., "$^1$H NMR Metabonomic Analysis in Renal Cell Carcinoma: a Possible Diagnostic Tool", Journal of Proteome Research, 9:4038-4044 (2010).
Agren et al., "Identification of anticancer drugs for hepatocellular carcinoma through personalized genome-scale metabolic modeling", Molecular Systems Biology, 10:721, pp. 1-13 (2014).
Galeotti et al., "Capillary electrophoresis separation of human milk neutral and acidic oligosaccharides derivatized with 2-aminoacridone", Electrophoresis, 35:811-818 (2014).
Gatto et al., "Glycosaminoglycan Profiling in Patients' Plasma and Urine Predicts the Occurrence of Metastatic Clear Cell Renal Cell Carcinoma", Cell Reports, 15:1822-1836 (2016).
Jonasch et al., "State of the Science: An Update on Renal Cell Carcinoma", Molecular Cancer Research, 10(7):859-880 (2012).
Kottler et al., "Development of a high-throughput glycoanalysis method for the characterization of oligosaccharides in human milk utilizing multiplexed capillary gel electrophoresis with laser-induced fluorescence detection", Electrophoresis, 34:2323-2336(2013).
Law et al., "voom: precision weights unlock linear model analysis tools for RNA-seq read counts", Genome Biology, 15(2):R29, pp. 1-17 (2014).
Maroto et al., "Molecular Biomarkers in Advanced Renal Cell Carcinoma", Clinical Cancer Research, 20(8):2060-2071 (2014).
Maruzzo et al., "Role of dose exposure and inflammatory status in a single center, real-world analysis of sunitinib in patients with metastatic renal cell carcinoma", Future Oncology, 12(7):909-919 (2016).
Moch et al., "Biomarkers in renal cancer", Virchows Arch, 464:359-365 (2014).
Negrier et al., "Interleukin-6, Interleukin-10, and Vascular Endothelial Growth Factor in Metastatic Renal Cell Carcinoma: Prognostic Value of Interleukin-6-From the Groupe Français d'Immunotherapie", Journal of Clinical Oncology, 22(12):2371-2378 (2004).
Ramankulov et al., "Serum amyloid A as indicator of distant metastases but not as early tumor marker in patients with renal cell carcinoma", Cancer Letters, 269:85-92 (2008).
Rasmuson et al., "Serum Insulin-like Growth Factor-1 is an Independent Predictor of Prognosis in Patients with Renal Cell Carcinoma", Acta Oncologica, 43(8):744-748 (2004).
Rossi et al., "Dynamic changes of live/apoptotic circulating tumour cells as predictive marker of response to Sunitinib in metastatic renal cancer", British Journal of Cancer, 107:1286-1294 (2012).

(Continued)

*Primary Examiner* — Christopher Adam Hixson
(74) *Attorney, Agent, or Firm* — Wenderoth, Lind & Ponack, L.L.P.

(57) ABSTRACT

The present invention relates to a method of screening for renal cell carcinoma in a subject, said method comprising determining the level and/or chemical composition of one or both of the glycosaminoglycans (GAGs) chondroitin sulfate (CS) and heparan sulfate (HS) in a body fluid sample, wherein said sample has been obtained from said subject.

23 Claims, 17 Drawing Sheets

(56) References Cited

PUBLICATIONS

Figure 1A:
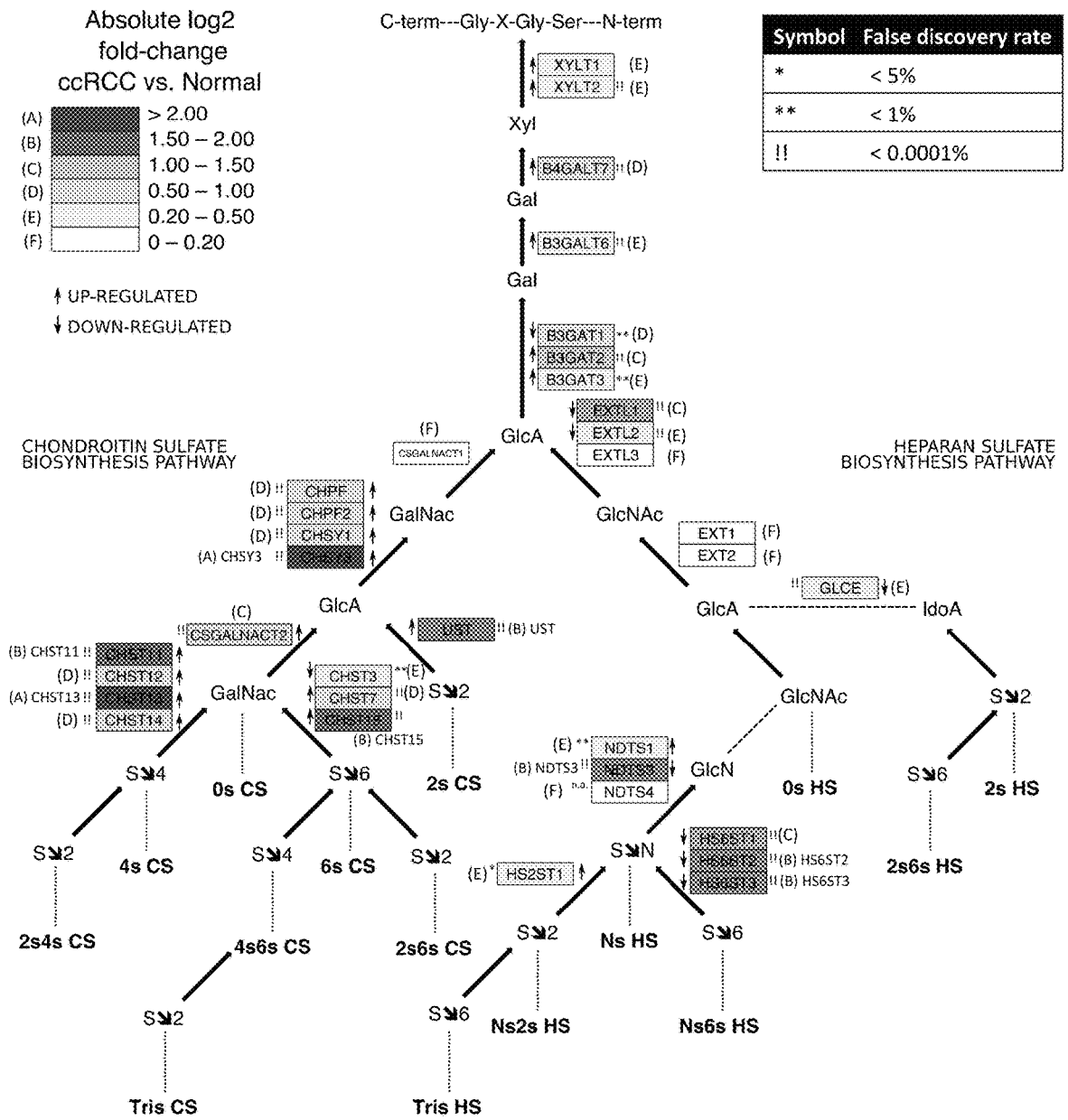

Sawyers, "The cancer biomarker problem", Nature, 452:548-552 (2008).

Smyth, "Linear Models and Empirical Bayes Methods for Assessing Differential Expression in Microarray Experiments", Statistical Applications in Genetics and Molecular Biology, 3(1), Article 3:1-25 (2004).

Sun et al., "Prognostic Factors and Predictive Models in Renal Cell Carcinoma: A Contemporary Review", European Urology, 60:644-661 (2011).

Tibshirani, "Regression Shrinkage and Selection via the Lasso", Journal of the Royal Statistical Society, Series B (Methodological), 58(1):267-288 (1996).

Ucakturk et al., "Changes in composition and sulfation patterns of glycoaminoglycans in renal cell carcinoma", Glycoconj J, 33:103-112 (2016).

Väremo et al., "Kiwi: a tool for integration and visualization of network topology and gene-set analysis", BMC Bioinformatics, 15:408, pp. 1-6 (2014).

Väremo et al., "Enriching the gene set analysis of genome-wide data by incorporating directionality of gene expression and combining statistical hypotheses and methods", Nucleic Acids Research, 41(8):4378-4391 (2013).

Volpi et al., "Analysis of glycosaminoglycan-derived, precolumn, 2-aminoacridone-labeled disaccharides with LC-fluorescence and LC-MS detection", Nature Protocols, 9(3):541-558 (2014).

Volpi et al., "High-performance liquid chromatography-mass spectrometry for mapping and sequencing glycosaminoglycan-derived oligosaccharides", Nature Protocols, 5(6):993-1004 (2010).

Volpi et al., "Glycosaminoglycan Composition of the Large Freshwater Mollusc Bivalve *Anodonta anodonta*", Biomacromolecules, 6:3174-3180 (2005).

Volpi et al., "Microdetermination of chondroitin sulfate in normal human plasma by fluorophore-assisted carbohydrate electrophoresis (FACE)", Clinica Chimica Acta, 356:125-133 (2005).

Coppa et al., "Composition and structure elucidation of human milk glycosaminoglycans", Glycobiology, 21(3):295-303 (2011).

Batista et al., "Heparanase expression and glycosaminoglycans profile in renal cell carcinoma", International Journal of Urology, 19:1036-1040 (2012).

López-Ratón et al., "OptimalCutpoints: An R Package for Selecting Optimal Cutpoints in Diagnostic Tests", Journal of Statistical Software, 61(8):1-36 (2014).

Volpi, "Advances in Chondroitin Sulfate Analysis: Application in Physiological and Pathological States of Connective Tissue and During Pharmacological Treatment of Osteoarthritis", Current Pharmaceutical Design, 12:639-658 (2006).

Galeotti et al., "Online Reverse Phase-High-Performance Liquid Chromatography-Fluorescence Detection-Electrospray Ionization-Mass Spectrometry Separation and Characterization of Heparan Sulfate, Heparin, and Low-Molecular Weight-Heparin Disaccharides Derivatized with 2-Aminoacridone", Analytical Chemistry, 83:6770-6777 (2011).

Volpi et al., "Electrophoretic approaches to the analysis of complex polysaccharides", Journal of Chromatography B, 834:1-13 (2006).

Volpi et al., "Detection of submicrogram quantities of glycosaminoglycans on agarose gels by sequential staining with toluidine blue and Stains-All", Electrophoresis, 23:4060-4066 (2002).

Rodriguez-Cuartero, "Urinary glycosaminoglycans in renal cell carcinoma", Clinical Nephrology, 50(6):394 (1998).

Sarica et al., "Evaluation of Urinary Glycosaminoglycan Excretion in Patients with Renal Cell Carcinoma", European Urology, 31:54-57 (1997).

Mikami et al., "Expression of Heparanase in Renal Cell Carcinomas: Implications for Tumor Invasion and Prognosis", Clinical Cancer Research, 14(19):6055-6061 (2008).

Pastore et al., "Serum and Urine Biomarkers for Human Renal Cell Carcinoma", Disease Markers, 2015:1-9, Article ID 251403 (2015).

Gatto, "The Origin of Symmetry in the Metabolism of Cancer", Chalmers University of Technology, Thesis for the Degree of Doctor of Philosophy, 145 pages (2015).

\* cited by examiner

CANCER BIOMARKERS

The present invention relates to biomarkers for renal cell carcinoma and to methods of screening for renal cell carcinoma, in particular clear cell renal cell carcinoma (ccRCC). Such methods involve determining the level and/or composition of certain biomarkers which are indicative of renal cell carcinoma in a subject.

Clear cell renal cell carcinoma (ccRCC) is the most common form of kidney cancer. However, currently, no diagnostic biomarkers have been identified which are being used in the clinic.

Thus, what is needed in the art are new methods of screening for renal cell carcinoma. The identification of novel biomarkers for renal cell carcinoma (RCC) may potentially have clinical implications for a large number of patients and would be an important clinical advancement. So far, among the major difficulties that have impaired biomarker discovery and its translation into clinical practice are the detection of targets in accessible samples and the reproducibility of results (Sawyers, 2008). Here, the inventors provide evidence for a plasmatic and/or urinary marker of ccRCC which can be used in a highly specific and sensitive assay to detect ccRCC. Advantageously therefore, such methods are non-invasive and performed on readily obtainable samples, as well as being highly accurate and reproducible.

The availability of such a test has value for a number of medical decisions: to monitor ccRCC before and after surgery or drug treatment; to rule out the relapse of the disease during a longer period of time after which a patient is typically declared cured; to assess the occurrence of ccRCC in a population at risk, such as genetically predisposed individuals; to ascertain whether a metastasis is due to ccRCC or other neoplasms; to predict metastatic relapse in patients with confined ccRCC during follow-up; to distinguish small renal masses suspicious of ccRCC from non malignant diseases.

In this regard, the present inventors have identified that certain glycosaminoglycans (GAGs), i.e. chondroitin sulfate (CS) and heparan sulfate (HS), and chemical compositions of said GAGs, are found at differential levels in body fluid samples from renal cell carcinoma patients in comparison to control subjects. These differential levels of the GAGs CS or HS, or differential chemical compositions of the GAGs CS or HS (GAG profiles), can act as biomarkers for renal cell carcinoma and thus are useful in screening for renal cell carcinoma in subjects. The present inventors have thus determined that GAG profiles from accessible fluids are suitable to be used as a biomarker of disease, in particular as a diagnostic biomarker and as a prognostic biomarker.

A previous study (Batista et al., 2012, International Journal of Urology, 19:1036-1040) found an increase in CS levels and a decrease in HS levels and dermatan sulfate (DS) levels in RCC tissues versus non-neoplastic tissues from the same patient. However, this study reported that the GAG levels in urine showed no significant difference between RCC and control samples.

Surprisingly and advantageously, the present inventors have found that changes in the level of the GAGs CS and HS are observed in accessible body fluids of RCC patients and that these GAG profiles are suitable to be used as a biomarker of disease. The present inventors have also shown that in addition to the overall (total) levels or concentration of CS and HS and HA, other changes in the chemical composition, for example the specific disaccharide sulfation patterns, of CS and HS are also observed between cancer samples and normal samples and can be used very effectively to diagnose RCC. The inventors believe that they are the first to analyse the specific sulfation patterns of HS and CS in body fluids of RCC patients and, advantageously, such analysis of further parameters associated with the specific composition (e.g. sulfation) of the GAGs provides improved diagnostic and prognostic results.

Clearly the finding that diagnosis and/or prognosis can be carried out in an accessible body fluid sample, e.g. plasma or urine, from a subject is extremely advantageous and it is particularly surprising that changes are observed in plasma samples as the GAG composition in the plasma of healthy individuals is typically not affected by any tissue and is usually stable because it reflects a healthy homeostasis. Here however, the inventors observed a systemic alteration of GAG composition that was concomitant with ccRCC.

Advantageously the present inventors have also shown that the identified markers that are distinctive of occurrence of ccRCC and that are calculated based on measurements in accessible body fluids, are predictive of the clinical outcome independently of certain confounding factors, and are accurate and robust predictors of the disease. The ability to predict prognosis is also demonstrated.

Thus, in one aspect the present invention provides a method of screening for renal cell carcinoma in a subject, said method comprising determining the level and/or chemical composition of one or both of the glycosaminoglycans (GAGs) chondroitin sulfate (CS) and heparan sulfate (HS) in a body fluid sample, wherein said sample has been obtained from said subject.

In preferred methods of the invention an altered level and/or composition of chondroitin sulfate (CS) and/or heparan sulfate (HS) in said sample in comparison to a control level and/or composition is indicative of renal cell carcinoma in said subject.

In preferred methods of the invention both the level and the chemical composition are determined. In other preferred methods of the invention the chemical composition alone is determined, or, in other preferred methods, the level (total level or total concentration) of CS and/or HS alone is determined.

In other embodiments of the invention, the level (total level or total concentration) of hyaluronic acid (HA) can be measured either alone or in combination with the level and/or chemical composition of HS and/or CS. Thus, further methods of the invention provide a method of screening for renal cell carcinoma in a subject, said method comprising determining the level and/or chemical composition of one or more of the glycosaminoglycans (GAGs) chondroitin sulfate (CS), heparan sulfate (HS) and hyaluronic acid (HA) in a body fluid sample, wherein said sample has been obtained from said subject.

Glycosaminoglycans (GAGs) are sugar containing molecules which are attached to proteins on serine residues, i.e. can form a parts of a proteoglycan. They are formed from linear or unbranched chains of monosaccharides (i.e. are polysaccharides) which can be sulphated. Heparan sulphate (HS), chondroitin sulphate (CS), keratan sulphate (KS), hyaluronic acid (HA) and heparin are the common types of GAG, of which HS and CS are examples of sulfated GAGs. The different types of GAG are distinguished by different repeating disaccharide units. However, all types have the same tetrasaccharide core attached to the serine residue of the protein.

Thus, for example, CS and HS are GAGs that share a common biosynthetic route in the linkage to the core protein, but thereafter they differ in their polymerisation in that the CS repeating disaccharide is made up of repeating N-acetylgalactosamine (GalNAc) and glucuronic acid residues (GlcA), whilst the repeating disaccharide in HS is typically made up of repeating N-acetylglucosamine (GlcNAc) and glucuronic acid (GlcA) residues. Each monosaccharide is attached by a specific enzyme allowing for multiple levels of regulation over GAG synthesis.

The "level" of HS or CS or HA as referred to herein generally refers to the total level or amount (e.g. concentration) of the HS or CS or HA present in the sample. The level of CS and/or HS and/or HA in a sample can be measured or determined by any appropriate method which would be well-known and described in the art. A preferred method involves electrophoresis, in particular capillary electrophoresis, e.g. capillary electrophoresis with fluorescence detection, e.g. laser-induced fluorescence detection. Other suitable methods are gel electrophoresis, e.g. agarose gel electrophoresis (e.g. FACE, fluorophore-assisted carbohydrate electrophoresis) or mass spectrometry or liquid chromatography, e.g. HPLC, optionally in combination with mass spectrometry (HPLC-MS). Conveniently these levels can be measured as a concentration, for example, as a number of microgram per ml (μg/ml). However, again, any appropriate measure of level may be used.

In the methods of the present invention the levels of HS or CS or HA are determined separately or individually. In other words the methods do not involve the measurement of total GAG levels in a sample or the total levels of all the GAGs present in combination, but involve the measurement of the levels of one or more of the individual GAGs HS or CS or HA.

In preferred embodiments of the invention, an increased level (or concentration) of CS in said sample and/or an increased level (or concentration) of HS in said sample is indicative of RCC in said subject and can be used to screen, diagnose, etc., subjects as described elsewhere herein.

In particular embodiments, the level (e.g. total level, or concentration) of CS can be determined in for example plasma or urine samples.

In other particular embodiments, the level (e.g. total level or concentration) of HS can be determined in for example plasma or urine samples. Preferably said sample is a plasma sample.

In particular, an increased level (or concentration) of CS in a plasma sample is indicative of RCC in said subject.

In particular, an increased level (or concentration) of CS in a urine sample is indicative of RCC in said subject.

In particular, an increased level (or concentration) of HS in a plasma sample is indicative of RCC in said subject.

In particular, an increased level (or concentration) of HS in a urine sample is indicative of RCC in said subject.

In particular, an increased level (or concentration) of HA in a urine sample is indicative of RCC in said subject.

In particular, a decreased level (or concentration) of HA in a plasma sample is indicative of RCC in said subject.

The individual monosaccharide units making up the CS and HS can have different sulfation patterns in terms of the position of the sulfate molecules and the amount/number of sulfate molecules. For CS, sulfation may most commonly occur at one or more of position 2 of the GlcA and positions 4 and 6 of the GalNAc. For HS, sulfation may occur at one or more of position 2 of the GlcA after epimerization to IdoA (iduronic acid), positions 3 and 6 of the GlcNAc, and N-sulfation of the GlcNAc. Thus, each individual disaccharide in the GAG chain may have 0 (i.e. be unsulfated), 1, 2, 3 or 4 (only in HS) sulfation forms and this in turn gives rise to different overall chemical compositions of GAG chains in terms of sulfation levels and specific disaccharide sulfation patterns.

As described elsewhere herein, preferred embodiments of the invention involve the determination of the chemical composition of one or both of CS and HS. The term "chemical composition" as used herein can refer to both the levels of the GAGs as well as the disaccharide sulfation composition of the GAGs. In particular, this term includes a determination of one or more particular forms, e.g. sulfation forms, of the disaccharides making up the CS or HS GAGs. Put another way, the term "chemical composition" refers to the amount or level of one or more of the various sulfated and/or unsulfated forms of CS or HS disaccharides, as well as for example some other properties of the individual GAGs present, such as total HS or CS or HA GAG levels, or other properties related to GAG sulfation such as HS charge or CS charge as described further elsewhere herein. Such a chemical composition which is analysed or determined in the present invention can also be referred to herein as a GAG profile, GAG forms, GAG features or GAG properties. In this regard, up to 22 different GAG properties as described in more detail below can be measured in the methods of the invention and a collection or group (e.g. two or more) of these measurements taken from a particular sample can be referred to as a GAG profile. In preferred embodiments of the invention up to 20 different GAG properties as described in more detail below can be measured.

Thus, for example, the term "chemical composition" as used herein may refer to a determination or analysis of the sulfation patterns (e.g. one or more of the sulfation forms) of the disaccharides making up CS and/or HS.

For example, for CS, there are 8 main sulfated and unsulfated forms (sulfation patterns, disaccharide sulfation forms) which are: 0s CS (also referred to as unsulfated CS or CS 0 unit), 2s CS (also referred to as chondroitin-2-sulfate), 4s CS (also referred to as chondroitin-4-sulfate or CS A unit), 6s CS (also referred to as chondroitin-6-sulfate or CS C unit), 2s4s CS (also referred to as chondroitin-2-4-sulfate), 2s6s CS (also referred to as chondroitin-2-6-sulfate or CS D unit), 4s6s CS (also referred to as chondroitin-4-6-sulfate or CS E unit) and Tris CS (also referred to as chondroitin-2-4-6-sulfate or trisulfated CS).

Each of the above is a form of CS GAG (a CS GAG form or property) which may be measured in the methods of the present invention. One or more of these forms may be measured, for example up to 8, e.g. 1, 2, 3, 4, 5, 6, 7 or all 8 of these sulfation forms may be measured. In some embodiments, measurement of all 8 of these sulfation forms is preferred. Another GAG property for CS which may be measured in the methods of the present invention is the total concentration of CS (also referred to herein as CS tot or Tot CS) or the total level of CS. This is typically measured as a concentration, e.g. in μg/ml, as described elsewhere herein. In embodiments of the invention where the total concentration of CS is measured as one of the GAG properties, then it is preferred that at least one other GAG property or CS property is measured, e.g. a property that is not based on the total level of the other individual GAGs present (e.g. not total HS or total HA). In some embodiments the total concentration of CS is not measured. In some embodiments, the measurement of one or more CS GAG properties is preferred, in particular where the sample is a urine sample.

"Charge CS" is another GAG form or property which may be measured in the present invention, e.g. as part of the GAG profile. "Charge CS" refers to the total fraction of sulfated disaccharides of CS, i.e. the fraction of sulfated disaccharides of CS present or measured in a sample out of the total CS disaccharides present or measured in a sample (i.e. sulfated CS disaccharides/sulfated+unsulfated CS disaccharides). By way of example, in addition to the unsulfated form of CS (0s CS), where the sample is a plasma sample 4s CS may also be measured as a main sulfation form in order to calculate the charge CS (4s CS/4s CS+0s CS). Alternatively, in addition to the unsulfated form of CS (0s CS), where the sample is a urine sample 4s CS and 6s CS may also be measured as the main sulfation forms in order to calculate the charge CS (4s CS+6s CS/4s CS+6s CS+0s CS).

As the measurement of "charge CS" is dependent on the measurement of other properties, i.e. the measurement of levels of sulfated and unsulfated CS disaccharides, this property is not referred to herein as an independent GAG property or CS property. Thus, up to 9 independent CS properties can be measured in the methods of the present invention, which are the 8 sulfated and unsulfated forms listed above, together with the total CS. In some embodiments all 9 of these independent CS properties are measured.

In some embodiments it is preferred to measure up to 8 or all 8 of the CS sulfation forms (i.e. the sulfated and unsulfated forms), together with total CS and charge CS.

For example, for HS, there are 8 main sulfated and unsulfated forms (sulfation patterns, disaccharide sulfation forms) which are: 0s HS (also referred to as unsulfated HS), 2s HS (which is sulfated at the 2-position of GlcA), Ns HS (which is sulfated at the N-position of the GlcNAc), 6s HS (which is sulfated at the 6-position of the GlcNAc), 2s6s HS (which is sulfated at the 2-position of GlcA and the 6-position of the GlcNAc), Ns6s HS (which is sulfated at the 6-position and N-position of GlcNAc), Ns2s HS (which is sulfated at the 2-position of GlcA and the N-position of GlcNAc, Tris HS (which is sulfated at the 2-position of GlcA and 6-position and N-position of GlcNAc, also referred to as trisulfated HS). Note that sulfation in position 3 of the GlcNAc is also possible but rarely observed.

Each of the above is a form of HS GAG (an HS GAG form or property) which may be measured or determined in the methods of the present invention. However, due to its rarity, in preferred embodiments of the invention, the sulfation form with sulfation in position 3 of the GlcNAc is not measured. Thus, in the methods of the invention, one or more of these 9 (or preferably 8) forms may be measured, for example up to 9 (or preferably up to 8), e.g. 1, 2, 3, 4, 5, 6, 7, 8 or all 9 of these sulfation forms may be measured. In some embodiments, measurement of all 8 of these sulfation forms (excluding the sulfation form with sulfation in position 3 of the GlcNAc) is preferred. Another GAG property for HS which may be measured in the methods of the present invention is the total concentration of HS (also referred to herein as HS tot or Tot HS) or the total level of HS. This is typically measured as a concentration, e.g. in μg/ml, as described elsewhere herein. In embodiments of the invention where the total concentration of HS is measured as one of the GAG properties, then it is preferred that at least one other GAG property or HS property is measured, e.g. a property that is not based on the total level of the other individual GAGs present (e.g. not total CS or total HA). In some embodiments the total concentration of HS is not measured. The measurement of one or more HS GAG properties is preferred in the methods of the invention, e.g. where the sample is plasma or urine, in particular where the sample is a urine sample.

"Charge HS" is another GAG form or property which may be measured in the present invention, e.g. as part of the GAG profile. Charge HS refers to the total fraction of sulfated disaccharides of HS, i.e. the fraction of sulfated disaccharides of HS present or measured in a sample out of the total HS disaccharides present or measured in a sample (i.e. sulfated HS disaccharides/sulfated+unsulfated HS disaccharides). By way of example, in addition to the unsulfated form of HS (0s HS), where the sample is a plasma or urine sample Ns HS, 6s HS and/or 2s HS may also be measured as main sulfation forms in order to calculate the charge HS (e.g. Ns HS+6s HS+2s HS/Ns HS+6s HS+2s HS+0s HS).

As the measurement of "charge HS" is dependent on the measurement of other properties, i.e. the measurement of sulfated and unsulfated HS disaccharides, this property is not referred to herein as an independent GAG property or HS property. Thus, up to 10 independent HS properties can be measured in the methods of the present invention, which are the 9 sulfated and unsulfated forms listed above (preferably excluding the sulfation form with sulfation in position 3 of the GlcNAc), together with the total HS. Thus, in some embodiments 9 independent HS properties are measured (the 8 main sulfated and unsulfated HS forms plus total HS).

In some embodiments it is preferred to measure up to 8 or all 8 of the HS main sulfation forms (i.e. the sulfated and unsulfated forms listed above excluding the sulfation form with sulfation in position 3 of the GlcNAc), together with total HS and charge HS.

In some embodiments 9 independent HS properties are measured (the 8 main sulfated and unsulfated HS forms plus total HS) and the 9 independent CS properties are measured, i.e. 18 independent GAG properties.

These GAG properties or GAG forms, e.g. disaccharide sulfation forms (with the exception of total CS or total HS) are typically measured as a fraction size or fraction or proportion or relative measurement, rather than as absolute levels or concentrations, for example are given a value of less than 1 or are normalised to 1 depending on the levels of all the sulfation forms (or all the main sulfation forms) measured in the sample. In other words, the level of each of the desired sulfation forms is measured independently and then normalised to 1. When calculating such fractions, it is preferred that at least the main sulfation forms of CS or HS are measured in order to be able to normalise the fraction of the particular individual sulfation form to 1. In some embodiments, preferably at least the unsulfated forms of HS or CS are measured as the main sulfation form. In addition to the unsulfated form of CS, where the sample is a plasma sample 4s CS may also be measured as the main sulfation forms. In addition to the unsulfated form of CS, where the sample is a urine sample 4s CS and 6s CS may also be measured as the main sulfation forms. In addition to the unsulfated form of HS, where the sample is a plasma or urine sample Ns HS, 6s HS and/or 2s HS may also be measured as the main sulfation forms.

By way of example, levels of 0s CS, 4sCS and 6sCs are individually measured in a sample and then divided by the sum of the three measurements in order to obtain the measurement of the fraction. Relative measurements are generally preferred because they are more easy to interpret, for example, a measurement of 0s CS of 0.6 indicates that 60% of the CS disaccharides are unsulfated. However, absolute levels can also be measured.

Another GAG property which may be measured in the methods of the present invention is the total concentration of HA (also referred to herein as HA tot or Tot HA) or the total level of HA. This is typically measured as a concentration, e.g. in μg/ml, as described elsewhere herein. In embodiments of the invention where the total concentration of HA is measured as one of the GAG properties, then it is preferred that at least one other GAG property is measured, e.g. a property that is not based on the total level of the other individual GAGs present (e.g. not total CS or total HS).

In preferred embodiments of the invention, total HA is not measured, or put another way, only CS forms/properties and/or HS forms/properties are measured.

Thus, in preferred embodiments of the invention, the disaccharide composition (for example the specific sulfation patterns (e.g. sulfation forms)) of one or more of the disaccharides making up CS and/or HS is measured or determined. In more preferred embodiments one or more sulfation properties or forms of CS and/or HS such as those outlined above (e.g. 0s CS, 2s CS, etc), are measured or determined. Appropriate methods of doing this would be well known to a skilled person in the art and any of these could be used. However, a convenient method to achieve such quantification of disaccharide composition or the appropriate properties or forms of CS or HS (and separation of the disaccharide forms) is to use electrophoresis, in particular capillary electrophoresis, and preferably capillary electrophoresis with fluorescence detection, e.g. capillary electrophoresis with laser-induced fluorescence detection (CE-LIF). An alternative method is liquid chromatography, preferably HPLC (high-performance liquid chromatography), for example SAX HPLC. Preferably mass spectrometry is also used (e.g. HPLC-MS), for example electrospray ionization mass spectrometry (ESI-MS). Alternatively, mass spectrometry can be used without chromatography, e.g. liquid chromatography. Particularly preferred methods are outlined in the Examples. One example of a particularly preferred method is capillary electophoresis with laser-induced fluorescence detection. Another example of a particularly preferred method is HPLC ESI-MS.

In some methods of the invention where the levels of one or more individual disaccharide forms are measured, the GAGs are subjected to a processing step, for example a step of fragmentation or cleavage or digestion, e.g. by chemical digestion or enzyme treatment, e.g. with chondroitinase ABC or chondroitinase B, in order to obtain the disaccharide units which are then analysed.

In some methods of the invention the GAGs in the sample are subjected to a step of extraction (e.g. using a protease such as proteinase K) and/or purification, e.g. using an anion-exchange resin.

In some methods of the invention the GAGs in the sample (e.g. various different GAG forms in the sample) are subjected to a step of separation and/or quantification, as described elsewhere herein.

Other methods which might be used are known in the art. However, examples are analytical techniques involving the use of antibodies to various GAG forms, e.g. techniques such as Western blot, ELISA or FACS, or methods involving agarose gel electrophoresis (e.g. fluorophore-assisted carbohydrate electrophoresis (FACE)) or polyacrylamide gel electrophoresis (PAGE).

Thus preferred methods of the invention provide a method of screening for renal cell carcinoma in a subject, said method comprising determining or measuring the amount or level in a body fluid sample of one or more of the various sulfated and/or unsulfated forms of CS or HS disaccharides (in other words determining the GAG sulfation patterns), the total fraction of sulfated disaccharides of HS or CS (i.e. charge HS or charge CS), or the total concentration of CS or HS or HA. For CS this may involve determining one or more of the forms of CS selected from the group consisting of: charge CS, CS tot, 0s CS, 2s CS, 6s CS, 4s CS, 2s6s CS, 2s4s CS, 4s6s CS and Tris CS. For HS, this may involve determining one or more of the forms of HS selected from the group consisting of: charge HS, HS tot, 0s HS, 2s HS, 6s HS, 2s6s HS, Ns HS, Ns2s HS, Ns6s HS and Tris HS. For HA, this may involve determining the total concentration of HA, i.e. HA tot.

As discussed herein, methods of the present invention may comprise determining or measuring one or more specific GAG forms (or groups of GAG forms) "selected from the group consisting of" certain specific GAG forms (or groups of GAG forms) set forth herein. For the avoidance of doubt, in some embodiments in which one or more of the specific GAG forms (or groups of GAG forms) discussed herein is measured or determined, one or more other (or distinct) GAG forms and/or one or more other biomarkers may additionally be measured or determined. Thus, "selected from the group consisting of" may be an "open" term. In some embodiments, only one or more of the specific GAG forms (or groups of GAG forms) discussed herein is measured or determined (e.g. other GAG forms or other biomarkers are not measured or determined).

In some embodiments, 2s6s HS is not determined.

In some embodiments, an increased level in said sample of one or more of: Ns2s HS, Ns6s HS and Tris HS, for example in comparison to a control level, is indicative of RCC in said subject.

Particularly preferred GAG forms to be measured or determined in the methods of the invention are one or more of: 6s CS, 4s CS, Ns HS, Ns6s HS, the relative level of 4s CS with respect to 6s CS (e.g. the ratio 4s CS/6s CS or the inverse ratio 6s CS/4s CS), charge HS and CS total. Other preferred GAG forms to be measured in the methods of the invention are one or more of: the relative level of 6s CS with respect to 0s CS (e.g. the ratio 6s CS/0s CS or the inverse ratio 0s CS/6s CS) or the relative level of 4s CS with respect to 0s CS (e.g. the ratio 4s CS/0s CS or the inverse ratio 0s CS/4s CS).

For plasma samples, in preferred embodiments of the invention the methods involve the determination of one or more of: charge CS, CS tot, 2s CS, 6s CS, 4s CS, 2s6s CS, 2s4s CS, 4s6s CS, the relative level of 6s CS with respect to 4s CS (e.g. the ratio 6s CS/4s CS or the inverse ratio 4s CS/6s CS), the relative level of 6s CS with respect to 0s CS (e.g. the ratio 6s CS/0s CS or the inverse ratio 0s CS/6s CS) or the relative level of 4s CS with respect to 0s CS (e.g. the ratio 4s CS/0s CS or the inverse ratio 0s CS/4s CS).

For plasma samples, an increase in one or more of the sulphated forms of CS or total CS is indicative of RCC. In particular, an increase in one or more of: charge CS, CS tot, 2s CS, 6s CS, 4s CS, 2s6s CS, 4s6s CS, 2s4s CS, the relative level of 6s CS with respect to 4s CS (e.g. the ratio 6s CS/4s CS), the relative level of 6s CS with respect to 0s CS (e.g. the ratio 6s CS/0s) or the relative level of 4s CS with respect to 0s CS (e.g. the ratio 4s CS/0s), is indicative of RCC in said subject. Alternatively, an increase in one or more of: charge CS, 2s CS, 2s6s CS, 2s4s CS, the relative level of 6s CS with respect to 4s CS (e.g. the ratio 6s CS/4s CS), the relative level of 6s CS with respect to 0s CS (e.g. the ratio 6s CS/0s) or the relative level of 4s CS with respect to 0s CS (e.g. the ratio 4s CS/0s), is indicative of RCC in said subject.

For plasma samples, a decrease in the relative level of 4s CS with respect to 6s CS (e.g. the ratio 4s CS/6s CS) is indicative of RCC in said subject. A decrease in the relative level of 0s CS with respect to 6s CS (e.g. the ratio 0s CS/6s CS) or the relative level of 0s CS with respect to 4s CS (e.g. the ratio 0s CS/4s CS), is also indicative of RCC in said subject.

Thus, these markers can be used in the methods of the invention individually, although they can also be used in combination, e.g. in the form of a multi-marker assay. The ratios are particularly preferred markers, most particularly those reflecting the relative level of 4s CS with respect to 6s CS (e.g. the ratios 4s CS/6s CS or 6s CS/4s CS).

For plasma samples, in preferred embodiments of the invention the methods involve the determination of one or more of: charge HS, HS tot, 0s HS, Ns HS and Ns2s HS are determined. In other preferred embodiments of the invention the methods involve the determination of one or more of: charge HS, 0s HS and Ns HS. In particular an increase in the level of one or more of: HS tot, 0s HS, and Ns2s HS, for example in comparison to a control level, is indicative of RCC in said subject. Alternatively, a decrease in the level of one or more of: charge HS and Ns HS, for example in comparison to a control level, is indicative of RCC in said subject. Thus, these markers can be used in the methods of the invention individually, although they can also be used in combination, e.g. in the form of a multi-marker assay.

For plasma samples, in some embodiments HA tot may be measured. A decrease in the level of HA tot, for example in comparison to a control level, is indicative of RCC in said subject.

For urine samples, in preferred embodiments of the invention the methods involve the determination of one or more of: charge CS, CS tot, 0s CS, 6s CS, 4s CS, Tris CS, the relative level of 6s CS with respect to 0s CS (e.g. the ratio 6s CS/0s CS or the inverse ratio 0s CS/6s CS), the relative level of 4s CS with respect to 0s CS (e.g. the ratio 4s CS/0s CS or the inverse ratio 0s CS/4s CS) are determined. In other preferred embodiments of the invention one or more of: charge CS, 0s CS, Tris CS, the relative level of 6s CS with respect to 0s CS (e.g. the ratio 6s CS/0s CS or the inverse ratio 0s CS/6s CS), or the relative level of 4s CS with respect to 0s CS (e.g. the ratio 4s CS/0s CS or the inverse ratio 0s CS/4s CS) are determined.

In particular for urine samples an increase in the level of one or more of: CS tot and 0s CS (unsulfated CS), for example in comparison to a control level, is indicative of RCC in said subject. In particular embodiments, an increase in the level of 0s CS, for example in comparison to a control level, is indicative of RCC in said subject. Alternatively, a decrease in the level of one or more of the sulfated forms of CS, for example in comparison to a control level, is indicative of RCC in said subject. In particular, a decrease in the level of one or more of: charge CS, 6s CS, 4s CS, Tris CS, the relative level of 6s CS with respect to 0s CS (e.g. the ratio 6s CS/0s CS) and the relative level of 4s CS with respect to 0s CS (e.g. the ratio 4s CS/0s CS), for example in comparison to a control level, is indicative of RCC in said subject.

Thus, these markers can be used in the methods of the invention individually, although they can also be used in combination, e.g. in the form of a multi-marker assay. The ratios are particularly preferred markers.

For urine samples, in preferred embodiments of the invention the methods involve the determination of one or more of: charge HS, HS tot, 0s HS, 2s HS, 6s HS, Ns HS, Ns2s HS, Ns6s HS and Tris HS are determined. In other preferred embodiments one or more of: charge HS, 0s HS, 2s HS, Ns HS, and Tris HS are determined. For example, in urine samples, an increase in the level of one or more of the sulphated forms of HS or total HS, for example in comparison to a control level, is indicative of RCC. In particular, an increase in the level of one or more of: charge HS, HS tot, 2s HS, 6s HS, Ns HS, Ns2s HS, Ns6s HS and Tris HS, for example in comparison to a control level, is indicative of RCC in said subject. Alternatively, a decrease in the level of 0s HS (unsulfated HS), for example in comparison to a control level, is indicative of RCC in said subject. Thus, these markers can be used in the methods of the invention individually, although they can also be used in combination, e.g. in the form of a multi-marker assay.

For urine samples, in some embodiments HA tot may be measured. An increase in the level of HA tot, for example in comparison to a control level, is indicative of RCC in said subject.

Thus, in some embodiments, the level of a single GAG form (GAG property) is determined. For example, In one embodiment, the method comprises determining the level in a sample of one or more GAG features (GAG properties) that are identified in Table A herein as being significantly altered between RCC and healthy samples, i.e. those features with a "% in ROPE" (Region of Practical Equivalence) of less than 5.00.

In other embodiments, the level of more than one of the GAG forms (GAG properties) is determined (e.g. the level of two or more GAG forms, or three or more GAG forms, or four or more GAG forms, or five or more GAG forms is determined). By "more than one" is meant 2, 3, 4, 5, 6, 7, 8, 9, 10 etc. . . . 20 or 22 (including all integers between 2 and 20 or 2 and 22). In any list of markers or GAG properties provided herein, it is a preferred embodiment that all are measured. Also, a determination of the level of each and every possible combination of the GAG forms can be performed.

Thus, in some embodiments multi-marker methods are performed. Determining the level of multiple of the GAG forms (biomarker multiplexing) may improve screening (e.g. diagnostic) accuracy.

In a preferred embodiment, the level of two of the stated GAG forms is determined. In another preferred embodiment, the level of three of the stated GAG forms is determined. In yet another preferred embodiment, the level of four or five of the stated GAG forms is determined.

In the case of plasma, particularly preferred markers to be determined are one or more, or all, of: 6s CS, CS tot, the ratio of 4s CS to 6s CS (e.g. 6s CS/4s CS or 4s CS/6s CS) and Ns HS; or one or more, or all, of: 6s CS, CS tot and the ratio of 4s CS to 6s CS (e.g. 6s CS/4s CS or 4s CS/6s CS); or the ratio of 4s CS to 6s CS (e.g. 6s CS/4s CS or 4s CS/6s CS). Thus, one or more, two or more, three or more, or preferably all of these GAG forms might be measured in the methods of the invention.

In the case of plasma, the highest accuracy was reached by determining the level of the following GAG forms (properties), ranked by accuracy: 6s CS, the ratio 4s CS to 6s CS (e.g. 4s CS/6s CS), Ns HS, the ratio 6s CS to 0s CS (e.g. 6s CS/0s CS). Thus, one or more, two or more, three or more, or preferably all of these GAG forms might be measured in the methods of the invention. In preferred embodiments the most accurate form is used first, i.e. 6s CS. If other forms are added, then preferably they are added in the order shown in the list, i.e. the ratio 4s CS to 6s CS next, etc. In other embodiments 6s CS is not measured.

Other preferred GAG forms in plasma can be identified as having a % in ROPE value of less than 5.00 in Table A, e.g. less than 4.00, 3.00, 2.00 or 1.00 or even a value of 0.00.

In the case of urine, particularly preferred markers to be determined are one or more, or all, of: Ns6s HS, charge HS and 4s CS. Thus, one or more, two or more, or preferably all of these GAG forms might be measured in the methods of the invention.

In the case of urine, the highest accuracy was reached by determining the level of the following GAG forms (properties), ranked by accuracy: 4s CS, the ratio 4s CS to 0s CS (e.g. 4s CS/0sCS), the CS charge, 0s HS. Thus, one or more, two or more, three or more, or preferably all of these GAG forms might be measured in the methods of the invention. In preferred embodiments the most accurate form is used first, i.e. 4s CS. If other forms are added, then preferably they are added in the order shown in the list, i.e. the ratio 4s CS to 0s CS next, etc. In other embodiments 4s CS is not measured.

In some embodiments, the relative level of 4s CS with respect to 6s CS (e.g. the ratios 4s CS/6s CS or 6s CS/4s CS) is measured or determined (e.g. in plasma samples) in methods of the invention (e.g. in diagnostic or prognostic methods).

Based on the observed alterations in the levels of various GAG forms in RCC patients versus healthy patients, if desired, scoring methods, scoring systems, markers or formulas can be designed which use such levels of various GAG forms in order to arrive at an indication, e.g. in the form of a value or score, which can then be used for diagnosis. Appropriate scoring systems and parameters (e.g. GAG forms) to be measured can readily be designed based for example on the data described herein, for example in Table A, for example, based on one or more of the individual GAG features or properties which show significant differences in particular samples (plasma or urine) as indicated in Table A. In particular, GAG properties in Table A that are most different between RCC samples and healthy samples (e.g. preferably one or more or all properties which have a % in ROPE value of 0.00 or close to 0.00, e.g. one or more or all properties which have a % in ROPE value equal to or less than 5.00 or 4.00 or 3.00 or 2.00 or 1.00) are selected.

For example, with reference to Table A, two examples of plasma GAG properties that are most differential in mccRCC vs. healthy subjects are CS 4s and CS 6s. A simple formula for use in the methods of the invention is based on the ratio of these two properties:

$$\text{Plasma score} = \frac{[6s\ CS]}{[4s\ CS]}$$

As described elsewhere herein, appropriate threshold or cut-off values (used to declare a sample positive or negative) for use with this formula can be designed by a person skilled in the art. For example, the inventor used a cut-off value of 0.0146, where scores above this cut-off classify the sample as RCC with 85% accuracy and an AUC of 0.969.

In the attached Examples, the scoring systems (formulas) have been designed using measurements of multiple GAG forms such that a high score results in a positive diagnosis (i.e. the finding of the presence of RCC), but equally a skilled person could readily design and choose the scoring method and parameters used in such scoring method such that a low score gives rise to a positive diagnosis. The relevant features to be analysed in such scoring system can also be chosen based on the sample type to be analysed, again for example using the data as presented in Table A.

Some preferred and exemplary scoring systems or methods (formulae) are provided herein.

Thus, a preferred scoring system giving rise to a score when a plasma sample from a subject is analysed is:

$$\text{Plasma score} = \frac{[6s\ CS] + CS_{tot}}{\frac{3}{10}\frac{[4s\ CS]}{[6s\ CS]} + [Ns\ HS]}$$

A preferred scoring system when urine from a subject is analysed is:

$$\text{Urine score} = \frac{[Ns6s\ HS] + 60 \cdot \text{Charge } HS}{[4s\ CS]}$$

A preferred scoring system to be used when both plasma and urine samples are analysed is:

$$\text{Combined score} = \text{mean}(\text{Plasma score}, \text{Urine score})$$

In the above scoring systems the terms in brackets represent the fraction of the particular GAG form concerned (as described elsewhere herein), CS tot is the total concentration of CS in µg/ml and charge HS is the total fraction of sulphated disaccharides of HS. In other embodiments, these specific formulae are not used.

It should be noted that these preferred scoring systems are given as preferred examples, wherein a high score gives rise to a positive screening for, diagnosis of etc., the presence of RCC. However, it is clear that minor changes to these formula and/or to the parameters (GAG properties, GAG forms) measured in a particular sample could be made without having a significant impact on the score or the diagnostic result.

For example, with reference to the formula that yields the plasma score, a small variation could be the change of the coefficient of the term $$\frac{[4s\ CS]}{6s\ CS]}$$

and the removal of the term [Ns HS].

An example of such modified formula could be:

$$\text{Plasma score} = \frac{[6s\ CS] + CS_{tot}}{\frac{[4s\ CS]}{[6s\ CS]}}$$

As described elsewhere herein, appropriate threshold or cut-off values (used to declare a sample positive or negative) for use with this formula can be designed by a person skilled in the art. For example, the inventor used a cut-off value of 0.080, where scores above this cut-off classify the sample as RCC with 82% accuracy and an AUC of 0.981.

Where the aim is to provide a scoring system in which a high score is indicative of the presence of cancer then conveniently said scoring system can be designed as a ratio or fraction, where the numerator is the sum of the values associated with one or more GAG properties (GAG forms) associated with RCC and the denominator is the sum of the values associated with one or more GAG properties (GAG forms) associated with the healthy state.

Of course, as discussed above, alternative scoring systems (formulae) could equally be designed where for example the numerator is the sum of the values associated with one or more GAG properties (GAG forms) associated with the healthy state and the denominator is the sum of the values associated with one or more GAG properties (GAG forms) associated with RCC, and a low score is indicative of the presence of RCC.

For instance, alternative scoring methods, scoring systems, markers or formulas can be used that comprises any appropriate combination of the GAG properties in order to arrive at an indication, e.g. in the form of a value or score, which can then be used for diagnosis. For example, said methods etc., can be an algorithm that comprises any appropriate combination of the GAG properties as input, to e.g. perform pattern recognition of the samples, in order to arrive at an indication, e.g. in the form of a value or score, which can then be used for diagnosis. Non-limiting examples of such algorithms include machine learning algorithms that implement classification (algorithmic classifiers), such as linear classifiers (e.g. Fisher's linear discriminant, logistic regression, naive Bayes classifier, perceptron); support vector machines (e.g. least squares support vector machines); quadratic classifiers; kernel estimation (e.g. k-nearest neighbor); boosting; decision trees (e.g. random forests); neural networks; learning vector quantization.

The use of such classifiers, e.g. machine learning classifiers, e.g. random forest classifiers, would be within the skill of a person skilled in the art. For example, such classifiers can conveniently be trained on GAG properties from a training set of samples and then tested in terms of accuracy on a test set of samples. The classifier generates a black-box model that is trained on the most important GAG properties and can thus be used to identify the most important GAG properties which can be used to arrive at an accurate diagnosis.

By using a random forest classifier the five most important GAG properties for an accurate diagnosis in plasma were (in order): the ratio of 4s CS to 6s CS, Ns HS, the ratio of 6s CS to 0s CS, 6s CS, and 0s HS. The next seven most important GAG properties were (in order): 2s4s CS, 4s6s CS, Ns2s HS, 0s CS, 4s CS, charge HS, and 6s HS (see FIG. 7). Thus, one or more, two or more, three or more, etc., or all 5 or all 12 of these GAG forms might be measured in the methods of the invention. In preferred embodiments the most accurate form is used first, i.e. the ratio of 4s CS to 6s CS. If other forms are added, then preferably they are added in the order shown in the list, i.e. Ns HS next, etc.

By using a random forest classifier the five most important GAG properties for an accurate diagnosis in urine were (in order): 4s CS, the ratio of 4s CS to 0s CS, 0s CS, charge CS, 0s HS. The next seven most important GAG properties were (in order): charge HS, the ratio of 6s CS to 0s CS, Ns2s HS, Ns6s HS, 6s HS, total CS and total HS (see FIG. 8). Thus, one or more, two or more, three or more, etc., or all 5 or all 12 of these GAG forms might be measured in the methods of the invention. In preferred embodiments the most accurate form is used first, i.e. 4s CS. If other forms are added, then preferably they are added in the order shown in the list, i.e. the ratio of 4s CS to 0s CS next, etc.

The performance of the three specific disease scores given above (plasma, urine and combined scores) was evaluated using the receiver operating characteristic (ROC) curves and the area under the curve (AUC) was found to be 1.000 (i.e. a perfect classifier) in the case of the combined and plasma score and 0.966 for the urine score. This is shown in FIG. 4B and Table B. Taken together, these findings demonstrate that alterations in plasma and urine GAG chemical composition occurring in RCC can be summarised into scores. In turn, these scores accurately distinguished diseased from healthy individuals and can thus be used for screening, diagnosis, etc. These scores have also been validated on an independent cohort and, using an appropriate threshold or cut-off value (used to declare a sample positive or negative), show excellent results (AUC of 1.000) with a specificity of 100% for all three marker scores and sensitivities of 100% (for the combined marker score), 77.8% (for the plasma marker score) and 85.7% (for the urine marker score), see FIG. 4D and Table B. Thus, these results shown that the above invention provides a simple and accessible test to allow accurate diagnosis of the presence of RCC in an individual.

In the methods of the invention, appropriate threshold or cut-off scores can be calculated by methods known in the art, for example from the ROC curve, for use in the methods of the invention. Thus, in the Examples, for the three specific marker systems discussed above, an optimal threshold (cut-off) score was determined/selected which would maximise the positive predictive value (PPV) of the marker (e.g. Lopez-Raton et al., 2014, J. Stat Softw 61, 1-36), i.e. a sample whose marker score is below this threshold (cut-off) value has the maximum probability of not being RCC, or, put another way, a sample whose marker score is above this cut-off value has the maximum probability of being RCC. These cut-off scores were 0.616 (for the combined marker score), 0.234 (for the plasma marker score) and 1.133 (for the urine marker score), see FIGS. 4B and 4D and Table B. This way of determining threshold values could be used for any of the markers described herein. Such threshold (cut-off) scores can then conveniently be used to assess the appropriate samples in subjects and to arrive at a diagnosis.

For comparison, AUC values for biomarkers currently used in the clinic are in the range of 0.60-0.70. Thus, it can be seen that the methods of the invention provide a significant advance on this (AUC values of 1 can be achieved) and should be clinically useful. In addition, 90-95% is a desired level of PPV for use in the clinic, which is also achieved by methods of the present invention (PPV values of 100% can be achieved).

As discussed above, the present invention provides a method of screening for RCC in a subject. Alternatively viewed, the present invention provides a method of diagnosing RCC in a subject. Alternatively viewed, the present invention provides a method for the prognosis of RCC in a subject (prognosis of the future severity, course and/or outcome of RCC). Alternatively viewed, the present invention provides a method of monitoring for the occurrence of RCC in a subject at risk. Alternatively viewed, the present invention provides a method for monitoring the progression of RCC in a subject. Alternatively viewed, the present invention provides a method of determining the clinical severity of RCC in a subject. Alternatively viewed, the present invention provides a method for predicting the response of a subject to therapy for RCC. Alternatively viewed, the present invention provides a method of determining the efficacy of a therapeutic or surgical regime for RCC in a subject. Alternatively viewed, the present invention provides a method for detecting the recurrence of RCC. Alternatively viewed, the present invention provides a method of patient selection or treatment selection, for example as it provides a means of distinguishing patients with small renal masses which are not RCC, e.g. are non-malignant, benign or indolent masses (but which can display some problematic renal symptoms and may be suspected to be RCC) from patients with RCC. Thus, alternatively viewed, the present invention provides a method for distinguishing RCC from non-malignant diseases.

Thus, the method of screening for RCC in accordance with the present invention can be used, for example, for diagnosing RCC, for the prognosis of RCC, for monitoring for the occurrence of RCC in a subject at risk, for monitoring the progression of RCC, for determining the clinical severity of RCC, for predicting the response of a subject to therapy for RCC, for determining the efficacy of a therapeutic or surgical regime being used to treat RCC, for detecting the recurrence of RCC, for patient selection or treatment selection, or for distinguishing small renal masses suspicious of RCC from other non malignant diseases. Methods for diagnosing RCC and methods for the prognosis of RCC are preferred.

Thus, in one aspect the present invention provides a method for diagnosing RCC in a subject. In some embodiments, a positive diagnosis (i.e. the presence of RCC) is made if the level of one or more of the GAG forms in the sample is altered (increased or decreased as the case may be) in comparison to a control level. GAG forms for which an increased level is indicative of (e.g. diagnostic of) RCC are described elsewhere herein. GAG forms for which a decreased level is indicative of (e.g. diagnostic of) RCC are described elsewhere herein. Alternatively, a number of different GAG forms or properties are analysed as described elsewhere herein to arrive at a diagnosis, e.g. using a scoring system or method. The methods of the invention can also be used to ascertain whether a metastasis is due to RCC, e.g. ccRCC, or other neoplasms.

In another aspect, the present invention provides a method for the prognosis of RCC in a subject. In such methods the level of one or more of the GAG forms discussed above in the sample is indicative of the future severity, course and/or outcome of RCC, e.g. survival chances. For example, an alteration (increase or decrease as the case may be) in the level of one or more of the GAG forms in the sample in comparison to a control level may indicate a poor prognosis. A highly altered level (or score), e.g. compared to control levels (or scores), may indicate a particularly poor prognosis.

Thus, in some embodiments, an increased level of one or more of the GAG forms for which an increased level is indicative of RCC is suggestive of (i.e. indicative of) a poor prognosis. In some embodiments, a decreased level of one or more of the GAG forms for which a decreased level is indicative of RCC is suggestive of (i.e. indicative of) a poor prognosis. Conversely, if one or more GAG forms has an unaltered level (or an essentially unaltered level) that can be indicative of a good prognosis.

Serial (periodic) measuring of the level of one or more of the GAG forms (biomarkers) in accordance with the present invention may also be used for prognostic purposes looking for either increasing or decreasing levels (or scores) over time. In some embodiments, an altering level (increase or decrease, as appropriate) of one or more of the GAG forms over time (in comparison to a control level, e.g. a level moving further away from the control level) may indicate a worsening prognosis. In some embodiments, an altering level (increase or decrease, as appropriate) of one or more of the GAG forms over time (in comparison to a control level, e.g. a level moving closer to the control level) may indicate an improving prognosis.

In one aspect the present invention provides a method for monitoring for the occurrence of RCC in a subject at risk of developing RCC. Such methods and the GAG forms which are measured are similar to the diagnostic methods as described herein, but are carried out on subjects that are at particular risk for developing RCC and thus may benefit from closer monitoring. Such "at risk" subjects would be readily identified by a person skilled in the art but would include for example subjects with a family history of RCC or a genetic predisposition to RCC, or subjects in remission from RCC, or subjects with recognized risk factors for RCC (for example subjects with chronic renal disease).

In this way, it can be seen that in some embodiments of the invention, the methods can be carried out on "healthy" patients (subjects) or at least patients (subjects) which are not manifesting any clinical symptoms of RCC, for example, patients with very early or pre-clinical stage RCC, e.g. patients where the primary tumor is so small that it cannot be assessed or detected or patients in which cells are undergoing pre-cancerous changes associated with RCC but have not yet become malignant.

Thus, the methods of the present invention can also be used to monitor disease progression. Such monitoring can take place before, during or after treatment of RCC by surgery or therapy, e.g. pharmaceutical therapy. Thus, in another aspect the present invention provides a method for monitoring the progression of RCC in a subject.

Methods of the present invention can be used in the active monitoring of patients which have not been subjected to surgery or therapy, e.g. to monitor the progress of RCC in untreated patients. Again, serial measurements can allow an assessment of whether or not, or the extent to which, the RCC is worsening, thus, for example, allowing a more reasoned decision to be made as to whether therapeutic or surgical intervention is necessary or advisable.

As discussed above, monitoring can also be carried out, for example, in an individual, e.g. a healthy individual, who is thought to be at risk of developing RCC, in order to obtain an early, and ideally pre-clinical, indication of RCC.

In another aspect, the present invention provides a method for determining the clinical severity of RCC in a subject. In such methods the level of one or more of the GAG forms in the sample shows an association with the severity of the RCC. Thus, the level of one or more of the GAG forms is indicative of the severity of the RCC. In some embodiments, the more altered (more increased or more decreased as the case may be) the level (or score) of one or more of the GAG forms in comparison to a control level, the greater the likelihood of a more severe form of RCC. In some embodiments the methods of the invention can thus be used in the selection of patients for therapy.

Serial (periodical) measuring of the level (or score) of one or more of the GAG forms (biomarkers) may also be used to monitor the severity of RCC looking for either increasing or decreasing levels over time. Observation of altered levels (increase or decrease as the case may be) may also be used to guide and monitor therapy, both in the setting of sub-clinical disease, i.e. in the situation of "watchful waiting" before treatment or surgery, e.g. before initiation of pharmaceutical therapy or surgery, or during or after treatment to evaluate the effect of treatment and look for signs of therapy failure.

Thus, the present invention also provides a method for predicting the response of a subject to therapy or surgery. For example, a subject with a less severe form or an early stage of RCC, as determined by the level of one or more of the GAG forms in a sample in accordance with the present invention, is generally more likely to be responsive to therapy or surgery, in particular surgery. In such methods the choice of therapy or surgery may be guided by knowledge of the level of one or more of the GAG forms in the sample.

The present invention also provides a method of determining (or monitoring) the efficacy of a therapeutic regime being used to treat RCC, in other words following or monitoring a response to treatment. In such methods, an alteration (increase or decrease as the case may be) in the level (or scores) of one or more of the GAG forms in accordance with the present invention indicates the efficacy of the therapeutic regime being used. For example, if the level of one or more of the GAG forms for which an increased level (or score) is indicative of RCC is reduced during (or after) therapy, this is indicative of an effective therapeutic regime. Conversely, for example, if the level of one or more of the GAG forms for which a decreased level (or score) is indicative of RCC is increased during (or after) therapy, this is indicative of an effective therapeutic regime. In such methods, serial (periodical) measuring of the level of one or more of the GAG forms (biomarkers) over time can also be used to determine the efficacy of a therapeutic regime being used. Similar methods can be used to provide a method of determining (or monitoring) the efficacy of a surgical regime being used to treat RCC.

The present invention also provides a method for detecting the recurrence (relapse) of RCC, for example in a subject that has previously had RCC but been successfully treated, e.g. by surgery or therapy (e.g. pharmaceutical therapy) such that they are judged to be in remission or cured, or for example to predict metastatic relapse in patients with confined ccRCC during follow-up. Such subjects form an "at risk" category and may well benefit from regular monitoring for RCC. Such methods for detecting the recurrence (or relapse) of RCC use the diagnostic methods as described herein in order to detect the presence or absence of RCC.

The present invention also provides a method of patient selection or treatment selection as it provides a means of distinguishing patients with RCC from patients with non-malignant diseases, e.g. non-malignant renal diseases (for example in the form of small renal masses which are not RCC, e.g. are non-malignant, but which can display some problematic renal symptoms and may be suspected to be RCC). Thus, alternatively viewed, the methods of the present invention provide a method for distinguishing RCC from non-malignant diseases.

Such methods of patient selection or treatment selection or methods for distinguishing RCC from non-malignant diseases use the diagnostic methods as described herein in order to detect the presence or absence of RCC.

The features and discussion herein in relation to the method of screening for RCC (e.g. in relation to preferred GAG forms or combinations thereof for measurement) apply, mutatis mutandis, to the other related methods of present invention (e.g. to a method of diagnosing RCC, etc.).

In one embodiment, the invention provides the use of the methods of the invention (e.g. screening, diagnostic or prognostic methods, etc., as described herein) in conjunction with other known screening, diagnostic or prognostic methods for RCC, such as radiological imaging (e.g. computed tomography, CT, scan) or magnetic resonance imaging (MRI scan), or histological assessment, e.g. using a tumor biopsy. Thus, for example, the methods of the invention can be used to confirm a diagnosis of RCC in a subject. In some embodiments the methods of the present invention are used alone.

The level of the GAG form in question can be determined or measured by analyzing the sample which has been obtained from or removed from the subject by an appropriate means. The determination is typically carried out in vitro.

Levels of one or more of the GAG forms in the sample can be measured (determined) by any appropriate assay, a number of which are well known and documented in the art. As described elsewhere herein, electrophoresis, e.g. agarose gel electrophoresis or capillary electrophoresis (in particular capillary electrophoresis with fluorescence detection such as CE-LIF) or liquid chromatography, in particular HPLC (high-performance liquid chromatography) in combination with mass spectrometry (MS) are preferred techniques for measuring (determining) the levels of one or more of the GAG forms in accordance with the present invention.

Suitable electrophoresis, e.g. capillary electrophoresis, and liquid chromatography, e.g. HPLC techniques for GAG form analysis, together with appropriate mass spectrometry methods (and associated data processing techniques) are well known and documented in the art.

A particularly preferred method for determining the level of one or more of the GAG forms in the sample is described herein in the Examples. For example, a preferred method used in the invention is capillary electrophoresis with laser-induced fluorescence detection, CE-LIF (e.g. as described in Galeotti et al., 2014, Electrophoresis 35: 811-818; and Kottler et al., 2013, Electrophoresis 34: 2323-2336). HPLC combined with post column derivatization and fluorimetric detection can also be used, e.g. as described in Volpi 2006, Curr Pharm Des 12:639-658, as can HPLC combined with ESI-MS (electrospray ionization-mass spectrometry), e.g. as described in Volpi and Linhardt, 2010, Nature protocols 5:993-1004, also with fluorimetric detection, e.g. as described in Galeotti and Volpi, 2011, Anal Chem 83:6770-6777, or Volpi et al., 2014, Nature Protocols 9:541-558. Agarose gel electrophoresis can also be used, e.g. FACE (fluorophore assisted carbohydrate electrophoresis) as described in Volpi and Maccari, 2006, Analyt Technol Biomed Life Sci, 834:1-13; and Volpi and Maccari, 2002, Electrophoresis 23:4060-4066.

Appropriate methods of sample preparation, e.g. GAG extraction and purification are also known and described in the art, for example Volpi and Maccari, 2005, Biomacromolecules 6:3174-3180 and Clin Chim Acta 356:125-133, Coppa et al., 2011 Glycobiology 21:295-303.

In some embodiments HPLC and mass spectrometry (and associated data processing techniques) is used to obtain a fraction of the level of one or more particular GAG forms (e.g. the sulfated or unsulfated discaccharide forms) in the sample in comparison to the total amount. For example, after sample preparation, GAGs can be digested using enzymes, separated in an HPLC column and characterized using MS. As described elsewhere herein, the quantities of one or more individual GAG forms (e.g. a particular sulfated or unsulfated discaccharide form) are conveniently normalised (i.e. divided) by the sum of all the quantities of individual GAG forms measured, to yield fractions.

In accordance with the present invention, a quantitative, semi-quantitative or qualitative assessment (determination) of the level of one or more of the GAG forms can be made. Appropriate methods of doing this would be well known to a skilled person in the art and any of these could be used. However, a convenient method to achieve such quantification of disaccharide composition or the appropriate properties or forms of CS or HS (and separation of the disaccharide forms) is to use electrophoresis, in particular capillary electrophoresis, and preferably capillary electrophoresis with fluorescence detection, e.g capillary electrophoresis with laser-induced fluorescence detection (CE-LIF) (e.g. as described in Galeotti 2014, supra, or Kottler 2013, supra). An alternative method is to use liquid chromatography, preferably HPLC (high-performance liquid chromatography), for example SAX HPLC or for example as described in Volpi 2006, supra, Galeotti and Volpi 2011, supra, Volpi et al., 2014, supra or Volpi and Linhardt, 2010, supra. Preferably mass spectrometry is also used (HPLC-MS), for example electrospray ionization mass spectrometry (ESI-MS), e.g. HPLC ESI-MS. Particularly preferred methods are outlined in the Examples. Thus, one example of a particularly preferred method is capillary electrophoresis (e.g. for example, capillary electophoresis with laser-induced fluorescence detection). Another example would be HPLC followed by MS (HPLC-MS), e.g. HPLC ESI-MS. Alternatively, mass spectrometry can be used without chromatography, e.g. liquid chromatography.

Generally, the determination of the GAG properties or forms in accordance with the present invention does not involve the measurement of GAG molecules in the exact same form as found in the body fluid of a subject (e.g. does not involve the measurement of a naturally occurring form of GAG). For example, such native or naturally occurring GAG molecules are often found in the form of long sugar chains attached to proteins, whereas for levels to be determined in accordance with the present invention generally such GAG molecules have to be at least separated or extracted from the proteins to which they are attached and often further processed. Thus, generally the methods of the invention are carried out on samples which have been processed in some way (e.g. are man-made rather than native samples).

Thus, in some embodiments, methods of the invention may include a step of processing a sample. In some embodiments, the methods of the invention may thus be performed on such processed samples or materials derived from such processed samples. Processing steps include, but are not limited to, extraction or purification of GAGs from the sample, steps of fragmentation or cleavage or digestion of proteins present in the sample, e.g. as a means of separating or extracting or removing GAGs from the protein to which they are attached, e.g. through the use of a protease such as proteinase K, purification of GAGs, e.g. using an anion-exchange resin, isolating cells from the sample, isolating cell components from the sample, extracting (e.g. isolating or purifying) proteins/peptides and/or nucleic acid molecules (DNA or RNA) from the sample. Said processing steps thus also include steps carried out on a body fluid sample to prepare it for analysis, e.g. in the case of a blood sample, such steps might include the steps to prepare an appropriate blood component for analysis, e.g. plasma or serum, or, in the case of a urine sample, the removal of cells or other impurities. A processing step may involve one or more of digestion, extraction, purification, boiling, filtration, lyophilization, fractionation, centrifugation, concentration, dilution, inactivation of interfering components, addition of reagents, derivatization, complexation and the like. Exemplary processing steps are described in the Examples.

In some methods of the invention where the levels of certain individual disaccharide forms are measured, the GAGs, e.g. the full length GAG molecules or the GAG molecules attached to proteins on serine residues, or polymerised polysaccharide chains of GAGs, or chains of repeating disaccharide units of GAGs, are subjected to a processing step, for example a step of fragmentation or cleavage or digestion, e.g. by chemical digestion or enzyme treatment, e.g. with chondroitinase ABC or chondroitinase B, in order to obtain the disaccharide units which are then analysed.

Other methods to determine levels or compositions of GAGs which might be used are known in the art. However, examples are analytical techniques involving the use of antibodies to various GAG forms, e.g. techniques such as Western blot, ELISA or FACS, or methods involving agarose gel electrophoresis (e.g. fluorophore-assisted carbohydrate electrophoresis (FACE)) or polyacrylamide gel electrophoresis (PAGE).

Thus, in some embodiments, the level of one or more GAG forms (e.g. specific sulfated or unsulfated forms of CS or HS disaccharides, which have for example been derived from the full length GAG molecule or a chain of repeating disaccharide units of a GAG molecule by fragmentation, cleavage or digestion) in association with (e.g. physical association with or in complex with or derivitized with) a reagent that is being used to detect the GAG form is determined. Thus, in some embodiments the level of a complex of a GAG form and the reagent used to detect the GAG form is determined. Reagents suitable for detecting particular GAG forms are discussed elsewhere herein, but include antibodies, or some kind of fluorophore (or other detectable label or dye) attached to (or used to derivitize) the GAG form in question, for example to make it detectable by a fluorimeter (or other detection device). Thus, purely by way of example, in some embodiments the level of a GAG form in association with (e.g. in complex with or derivitized with) an antibody or fluorophore or the like may be determined.

An altered level (or composition) of one or more of the GAG forms (GAG properties) as described herein includes any measurable alteration or change of the GAG form (biomarker) in question when the GAG form in question is compared with a control level. An altered level includes an increased or decreased level. Preferably, the level is significantly altered, compared to the level found in an appropriate control sample or subject. More preferably, the significantly altered levels are statistically significant, preferably with a p-value of <0.05.

The "increase" in the level or "increased" level of one or more of the GAG forms (GAG properties) as described herein includes any measurable increase or elevation of the GAG form (biomarker) in question when the GAG form in question is compared with a control level. Preferably, the level is significantly increased, compared to the level found in an appropriate control sample or subject. More preferably, the significantly increased levels are statistically significant, preferably with a p-value of <0.05.

The "decrease" in the level or "decreased" level of one or more of the GAG forms (GAG properties) as described herein includes any measurable decrease or reduction of the GAG form (biomarker) in question when the GAG form in question is compared with a control level. Preferably, the level is significantly decreased, compared to the level found in an appropriate control sample or subject. More preferably, the significantly decreased levels are statistically significant, preferably with a p-value of <0.05.

A "control level" is the level of a GAG form (GAG property) in a control subject or population (e.g. in a sample that has been obtained from a control subject or population). Appropriate control subjects or samples for use in the methods of the invention would be readily identified by a person skilled in the art, for example an appropriate control group is as described in the Examples. Such subjects might also be referred to as "normal" subjects or as a reference population. Examples of appropriate populations of control subjects would include healthy subjects, for example, individuals who have no history of any form of kidney disease (e.g. RCC) and no other concurrent disease, or subjects who are not suffering from, and preferably have no history of suffering from, any form of kidney disease, in particular individuals who are not suffering from, and preferably have no history of suffering from, renal cancer or RCC. Preferably such control subjects are also not suffering from, and more preferably have no history of suffering from, liver cancers. Preferably such control subjects are also not suffering from inflammatory pathologies. Preferably control subjects are not regular users of any medication. In a preferred embodiment control subjects are healthy subjects.

The control level may correspond to the level of the equivalent GAG form in appropriate control subjects or samples, e.g. may correspond to a cut-off level or range found in a control or reference population. Alternatively, said control level may correspond to the level of the marker (GAG form) in question in the same individual subject, or a sample from said subject, measured at an earlier time point (e.g. comparison with a "baseline" level in that subject). This type of control level (i.e. a control level from an individual subject) is particularly useful for embodiments of the invention where serial or periodic measurements of GAG form(s) in individuals, either healthy or ill, are taken looking for changes in the levels of the GAG form(s). In this regard, an appropriate control level will be the individual's own baseline, stable, nil, previous or dry value (as appropriate) as opposed to a control or cutoff level found in the general control population. Control levels may also be referred to as "normal" levels or "reference" levels. The control level may be a discrete figure or a range.

Although the control level for comparison could be derived by testing an appropriate set of control subjects, the methods of the invention would not necessarily involve carrying out active tests on control subjects as part of the methods of the present invention but would generally involve a comparison with a control level which had been determined previously from control subjects and was known to the person carrying out the methods of the invention.

The methods of screening, diagnosis etc., of the present invention are for renal cell carcinoma (RCC). In preferred embodiments, the renal cell carcinoma subtype is clear cell renal cell carcinoma (ccRCC). The methods of the present invention can be carried out on any stage of RCC or ccRCC, for example can be used for early or initial stages of RCC (e.g. clinical stage I and stage II RCC, which typically do not involve spread of disease to the lymph nodes or distant metastasis), or advanced or late stage RCC disease (e.g. clinical stage III, which typically involves spread of disease to the lymph nodes, and stage IV RCC, which includes patients with distant metastasis, i.e. metastatic RCC). Methods of screening etc., for the advanced stages of RCC (stages III or IV) are preferred embodiments of the invention, although early or initial stages can also be detected.

The classification of RCC as stages I to IV can be carried out by any art recognised and accepted definition. However, for reference, a preferred classification system is the TNM (T=primary tumour; N=Regional lymph nodes; M=distant metastasis) stage I-IV classification system of the American Joint Committee on Cancer (AJCC: Kidney. In: Edge S B et al., eds: AJCC Cancer Staging Manual. 7th ed. New York, N.Y.: Springer, 2010, 479-489).

In other preferred embodiments the renal cell carcinoma is a stage IV RCC or, more preferably, a metastatic form of renal cell carcinoma (as opposed to localized or confined RCC). Indeed, metastatic clear cell renal cell carcinoma (mccRCC) is particularly preferred, as well as advanced or late stage RCC. Other subtypes of RCC which can be screened using the methods of the present invention are papillary, collecting duct or sarcomatoid.

The methods of the present invention can be carried out on any appropriate body fluid sample. In this regard, although the present invention is exemplified with plasma and urine, appropriate GAG forms to be measured in other types of body fluid sample could be determined by a skilled person following the teaching as provided herein. Typically the sample has been obtained from (removed from) a subject, preferably a human subject. In other aspects, the method further comprises a step of obtaining a sample from the subject.

Reference herein to "body fluid" includes reference to all fluids derived from the body of a subject. Exemplary fluids include blood (including all blood derived components, for example plasma, serum, etc.), urine, saliva, tears, bronchial secretions or mucus. Preferably, the body fluid is a circulatory fluid (especially blood or a blood component) or urine. Especially preferred body fluids are plasma or urine or both. In some preferred embodiments the sample is a blood sample. In some preferred embodiments the sample is urine.

The term "sample" also encompasses any material derived by processing a body fluid sample (e.g. derived by processing a blood or urine sample). Processing of biological samples to obtain a test sample may involve one or more of: digestion, boiling, filtration, distillation, centrifugation, lyophilization, fractionation, extraction, concentration, dilution, purification, inactivation of interfering components, addition of reagents, derivatization, complexation and the like, e.g. as described elsewhere herein.

Any suitable method for isolating urine or blood/plasma samples may be employed.

Samples can be used immediately or can be stored for later use (e.g. at −80° C.).

The methods of the invention as described herein can be carried out on any type of subject which is capable of suffering from RCC. The methods are generally carried out on mammals, for example humans, primates (e.g. monkeys), laboratory mammals (e.g. mice, rats, rabbits, guinea pigs), livestock mammals (e.g. horses, cattle, sheep, pigs) or domestic pets (e.g. cats, dogs). Preferably the subject is a human.

In one embodiment, the subject (e.g. a human) is a subject at risk of developing RCC or at risk of the occurrence of RCC, e.g. a healthy subject or a subject not displaying any symptoms of renal disease or any other appropriate "at risk" subject as described elsewhere herein. In another embodiment the subject is a subject having, or suspected of having (or developing), or potentially having (or developing) RCC.

In some aspects, a method of the invention may further comprise an initial step of selecting a subject (e.g. a human subject) at risk of developing RCC or at risk of the occurrence of RCC, or having or suspected of having (or developing), RCC, or potentially having (or developing) RCC. The subsequent method steps can be performed on a sample from such a selected subject.

In some aspects, methods of the invention are provided which further comprise a step of treating RCC by therapy (e.g. pharmaceutical therapy) or surgery. For example, if the result of a method of the invention is indicative of RCC in the subject (e.g. a positive diagnosis of RCC is made), then an additional step of treating the RCC by therapy or surgery can be performed. In some embodiments of prognostic methods of the invention, an additional step of treating the RCC by therapy or surgery can be performed (e.g. if there is a poor prognosis). Methods of treating RCC by therapy or surgery are known in the art. For example, one surgical option is nephrectomy, which is aimed at eradication of the tumour and can be either radical (total removal) or partial (nephron sparing). Pharmaceutical treatment can include standard chemotherapy (e.g. gemcitabine, vinblastine, floxuridine, 5-fluorouracil, or capecitabine), targeted therapies (including tyrosine kinase inhibitors, mTOR pathway inhibitors, VEGF pathway inhibitors, or more specific examples such as sorafenib, sunitinib, temsirolimus, everolimus, bevacizumab, pazopanib, or axitinib) and immunotherapy (such as interferon-gamma, interleukin-2, interferon-alpha, or PD-1 or PD-L1 blockers such as nivolumab), in addition to therapies which are subject to ongoing clinical trials. Alternatively, methods of the invention are provided which further comprise a step of carrying out an additional diagnostic or prognostic procedure, e.g. a CT scan.

Thus, in some embodiments, methods of the invention (e.g. screening or diagnosis or prognosis methods) which further comprise a step of treating RCC may comprise administering to the subject a therapeutically effective amount of one or more agents selected from the group consisting of a chemotherapeutic agent, for example selected from gemcitabine, vinblastine, floxuridine, 5-fluorouracil, or capecitabine; an agent for targeted therapy, for example selected from tyrosine kinase inhibitors, mTOR pathway inhibitors, VEGF pathway inhibitors, or more specific examples such as sorafenib, sunitinib, temsirolimus, everolimus, bevacizumab, pazopanib, or axitinib; or an agent for immunotherapy, for example selected from interferon-gamma, interleukin-2, interferon-alpha, or PD-1 or PD-L1 blockers such as nivolumab.

In some embodiments, if the level of one or more GAG properties in a sample, or a score based on these levels, is altered by a particular degree in comparison to a control level or score, then a further step of administering a therapeutically effective amount of a pharmaceutical agent (e.g. a chemotherapeutic agent etc., as described above) to the patient is performed and/or surgery is performed. Preferred degrees of alteration are discussed elsewhere herein.

In some embodiments, if a subject is already undergoing pharmaceutical therapy (e.g. chemotherapeutic therapy or other therapy as described above) and the level of one or more GAG properties in a sample, or a score based on these levels, is altered (or indeed not altered) by a particular degree in comparison to a control level (e.g. in comparison to a previously recorded level or score for the same subject), then this may be indicative that the current therapeutic agent is not being effective and that a therapeutic agent other than the previous therapeutic agent should be used. Thus, a step of administering a therapeutically effective amount of a therapeutic agent (e.g. a chemotherapeutic agent etc. as described above) other than the therapeutic agent previously administered to the subject may be performed.

In some embodiments, if a method of the invention reveals that a current treatment regimen is ineffective, e.g. if serial or periodic measurements of one or more GAG properties in a sample, or a score based on these levels reveal treatment is being ineffective, a step of altering (e.g. increasing) the dosage of the therapeutic agent may be performed.

More specifically for example, in some such aspects of the invention, methods are provided which comprise determining the level of one or more GAG properties in a sample and if one or more levels, or a score based on these levels, are determined to be greater than an appropriate cut-off level, e.g. a cut-off level pre-specified to maximise the predictive value for a positive diagnosis of RCC or a cut-off level pre-specified to maximise the predictive value for prognosis (e.g. poor prognosis), then said methods may comprise the further step of performing a surgery (e.g. nephrectomy), or performing an additional diagnostic or prognostic procedure (e.g. a CT scan), or administering a therapeutically-effective amount of a recommended drug agent for the treatment of RCC, such agents for example comprising targeted therapies like sorafenib, sunitinib, temsirolimus, everolimus, bevacizumab, pazopanib, or axitinib, immunotherapies like interleukin-2, interferon-alpha, or PD-1 or PD-L1 blockers such as nivolumab, or chemotherapies like vinblastine, floxuridine, 5-fluorouracil, capecitabine or gemcitabine.

Conversely, methods are provided which comprise determining the level of one or more GAG properties in a sample and if one or more levels, or a score based on these levels, are determined to be lower than an appropriate cut-off level, e.g. a cut-off level pre-specified to maximise the predictive value for a negative diagnosis of RCC or a cut-off level pre-specified to maximise the predictive value for prognosis (e.g. good prognosis), then said methods may comprise the further step of not performing a surgery (e.g. nephrectomy), or performing an additional diagnostic or prognostic procedure (e.g. a CT scan) or altering the current dosage of drug agent(s) or administering a therapeutically-effective amount of a distinct recommended drug agent for RCC to the one already being used, such agents e.g. comprising targeted therapies like sorafenib, sunitinib, temsirolimus, everolimus, bevacizumab, pazopanib, or axitinib, immunotherapies like interleukin-2, interferon-alpha or PD-1 or PD-L1 blockers such as nivolumab, or chemotherapies like vinblastine, floxuridine, 5-fluorouracil, capecitabine and gemcitabine.

As indicated above, in one aspect the present invention provides a method for the prognosis of RCC in a subject, said method comprising determining the level and/or chemical composition of one or both of the glycosaminoglycans (GAGs) chondroitin sulfate (CS) and heparan sulfate (HS) in a body fluid sample, wherein said sample has been obtained from said subject.

In some embodiments, an alteration (an increase or decrease as the case may be) in the level and/or chemical composition of one or both of the glycosaminoglycans (GAGs) chondroitin sulfate (CS) and heparan sulfate (HS) in a body fluid sample (e.g. in comparison to a control level or score) may be indicative of prognosis.

Thus, prognostic methods of the invention may be used to predict (or estimate) the prognosis, e.g. whether a subject has a good (or a better) prognosis or whether a subject has a poor (or worse) prognosis. In some embodiments, an alteration (an increase or decrease as the case may be) in the level and/or chemical composition of one or both of the glycosaminoglycans (GAGs) chondroitin sulfate (CS) and heparan sulfate (HS) in a body fluid sample may be indicative of a good (or better) prognosis in relation to the prognosis for a control subject or control population (or average (e.g. median) control subject or level in a control or reference population) from which the control level (or score) was obtained (or derived). In some embodiments, an alteration (an increase or decrease as the case may be) in the level and/or chemical composition of one or both of the glycosaminoglycans (GAGs) chondroitin sulfate (CS) and heparan sulfate (HS) in a body fluid sample may be indicative of a poor (or worse) prognosis in relation to the prognosis for the control subject or control population (or average (e.g. median) control subject or level in a control or reference population) from which the control level (or score) was obtained (or derived).

Prognosis may be considered as an assessment of the survival prospects for a subject (e.g. over a given time period, e.g. 3, 6, 9, 12, 15, 18, 21, 24, 27, 30 or 33 months, or e.g. 5-year survival). Thus, alternatively viewed, the present invention provides a method of predicting (or determining) the survival prospects for a subject having RCC. In some embodiments, "survival" may be calculated as the time (e.g. in days) between the date of sampling (the date a sample is obtained from a subject) and the time of an "event". In some embodiments, "survival" may be calculated from start of RCC treatment, e.g the start of pharmaceutical therapy or the day of surgery.

In some embodiments, "survival" is "overall survival" (OS) or "progression-free survival" (PFS) or "recurrence-free survival" (RFS). Thus, the present invention provides a method of predicting (or determining) the overall survival (OS) prospects or progression-free survival (PFS) prospects or recurrence-free survival (RFS) prospects for a subject. In some embodiments, "survival" is "overall survival" (OS) or "progression-free survival" (PFS).

In one embodiment, "survival" is "overall survival" (OS). In such embodiments, the "event" is the date of death. Thus, in some embodiments, prognostic methods of the invention may be used to predict (or estimate) the probability of death occurring in a particular future time period (e.g. 3, 6, 9, 12, 15, 18, 21, 24, 27, 30 or 33 months, or e.g. 5-year survival). In some embodiments, prognostic methods of the invention may be used to predict or estimate the amount of time before death.

In one embodiment, "survival" is "progression-free survival" (PFS). In such embodiments, the "event" is the date of progression (i.e. the date of disease progression). Thus, in some embodiments, prognostic methods of the invention may be used to predict (or estimate) the probability of the disease progressing in a particular future time period (e.g. 3, 6, 9, 12, 15, 18, 21, 24, 27, 30 or 33 months, or e.g. 5-year survival). In some embodiments, prognostic methods of the invention may be used to predict (or estimate) the amount of time before the disease progresses (or worsens).

In one embodiment, "survival" is "recurrence-free survival" (RFS). In such embodiments, the "event" is the date of recurrence or relapse (i.e. the date of disease recurrence or relapse). In some embodiments, recurrence is metastatic recurrence or metastatic relapse. In some embodiments, recurrence is local recurrence or local relapse. Thus, in some embodiments, prognostic methods of the invention may be used to predict (or estimate) the probability of the disease recurrence or relapse in a particular future time period (e.g. 3, 6, 9, 12, 15, 18, 21, 24, 27, 30 or 33 months, or e.g. 5-year survival). In some embodiments, prognostic methods of the invention may be used to predict (or estimate) the amount of time before the disease recurs or relapses.

In some embodiments of the prognostic methods of the invention, the bodily fluid is plasma and/or urine. In a preferred embodiment, the bodily fluid is urine.

In some embodiments, a bodily fluid sample (e.g. urine and/or plasma) is obtained just once (a single time) from a subject.

As discussed above, various GAG properties (or GAG forms) and combinations thereof may be used for measurement, and these may used, as appropriate, in relation to the prognostic methods of the invention.

Based on the observed alterations in the levels of various GAG forms in RCC patients (e.g. ccRCC or metastatic ccRCC) scoring methods, scoring systems, markers or formulas can be designed which use such levels of various GAG forms in order to arrive at an indication, e.g. in the form of a value or score, which can then be used for prognosis. Scoring methods and systems are discussed elsewhere herein and any suitable scoring system may be used. In certain preferred embodiments of the prognostic methods of the invention, a score is derived and the score is used for prognosis (e.g. to provide an indication of the overall survival prospects and/or progression-free survival prospects).

In some embodiments, a urine score is obtained (or calculated). In a preferred embodiment, the urine score is obtained according to the following formula:

$$\text{Urine score} = \frac{[Ns6s\ Hs] + 60 \cdot \text{Charge}\ HS}{[4s\ CS]}$$

In some embodiments, a plasma score is obtained (or calculated). In a preferred embodiment, the plasma score is obtained according to the following formula:

$$\text{Plasma score} = \frac{[6s\ CS] + CS_{tot}}{\frac{3}{10}\frac{[4s\ CS]}{[6s\ CS]} + [Ns\ HS]}$$

In some embodiments, a combined plasma and urine score may be used (combined score=mean(Plasma score, urine score)), as described elsewhere herein.

Prognostic methods of the present invention are for the prognosis of RCC and thus in some embodiments, subjects have RCC (have a current diagnosis of RCC) or are known to have had RCC (have had a former diagnosis of RCC) or are at risk of developing RCC during their lifetime.

In some embodiments, subjects have RCC (have a current diagnosis of RCC) or are known to have had RCC (have had a former diagnosis of RCC).

In a preferred embodiment of the prognostic methods of the invention, the method is a method for the prognosis of clear cell RCC (ccRCC). Thus, in some embodiments, subjects are known to have ccRCC (have a current diagnosis of ccRCC) or are known to have had ccRCC (have had a former diagnosis of ccRCC).

In a particularly preferred embodiment of the prognostic methods of the invention, the method is for the prognosis of metastatic ccRCC (mccRCC). Thus, in some embodiments, subjects are known to have mccRCC (have a current diagnosis of mccRCC) or are known to have had mccRCC (have had a former diagnosis of mccRCC). In a preferred embodiment, the subject is known to have mccRCC (have a current diagnosis of mccRCC). In this regard, even if a subject is already known to have metastatic ccRCC, the prognostic methods of the present invention still provide useful prognostic information in terms of survival prospects (e.g. overall survival prospects or progression-free survival prospects) for a subject having mccRCC. Thus, within a group of subjects having metastatic ccRCC, the level and/or composition of chondrotin sulfate (CS) or heparan sulfate in the sample (e.g. in comparison to a control level or composition) can be used to predict which mccRCC subjects have a good (or better) prognosis (e.g. in terms of overall survival prospects or progression-free survival prospects) and which mccRCC subjects have a poor (or worse) prognosis (e.g. in terms of overall survival prospects or progression-free survival prospects). For example, when the preferred scoring system (e.g. plasma score and/or urine score) described herein is employed, those mccRCC subjects having a high (or higher) biomarker score have a worse prognosis (e.g. a significantly worse prognosis) than those mccRCC subjects having a low (or lower) biomarker score.

The current or former diagnosis mentioned in the above paragraph may in some embodiments be based on clinical examination and on computer tomography or other radiological assessments at follow-up.

In some embodiments, prognostic methods can identify patients at higher risk and subsequently guide the therapeutic choices. Thus, treatment regimens may be decided upon depending on whether the subject has a good prognosis (low risk) or poor prognosis (high risk).

In a preferred embodiment, the prognosis is not for non-clear cell RCC.

In some embodiments, subjects may be receiving systemic treatment for metastatic disease (e.g. with sunitinib or everolimus or nivolumab) or be on follow-up observation.

In some embodiments, subjects may not be receiving (or may never have received) systemic treatment for metastatic disease.

In one preferred method for prognosis of RCC (e.g. of metastatic ccRCC), the bodily fluid is urine and the prognosis is in terms of progression-free survival.

In one preferred method for prognosis of RCC (e.g. of metastatic ccRCC) the bodily fluid is urine and the prognosis is in terms of overall survival.

In one preferred method for prognosis of RCC (e.g. of metastatic ccRCC) the bodily fluid is plasma and the prognosis is in terms of overall survival.

In one preferred embodiment, the prognosis is of mccRCC (e.g. patients known to have current diagnosis of mcRCC) and the bodily fluid is urine.

In a particularly preferred method the prognosis is of mccRCC (e.g. patients known to have current diagnosis of mcRCC), the bodily fluid is urine and the prognosis is in terms of progression-free survival.

As mentioned above, in some embodiments of the prognostic methods of the invention an altered level and/or composition of chondroitin sulfate (CS) and/or heparan sulfate (HS) in said sample in comparison to a control (or cut-off or threshold) level and/or composition is indicative of prognosis for renal cell carcinoma (e.g. ccRCC or metastatic ccRCC) in said subject. Control levels are discussed elsewhere herein and appropriate control levels for use in the prognostic methods of the invention can be readily determined by a person skilled in the art.

Altered levels (or scores), for example increased or decreased levels, are discussed elsewhere herein. Whether an altered level (or score) for one or more of the GAG forms (GAG properties) is indicative of good or poor prognosis may depend on the GAG form(s) being analysed. Purely by way of example, if a control level is the level of a given GAG form that is increased in mccRCC, then an increased level of that GAG form in the subject in comparison to the control level may be indicative of poor (or poorer) prognosis, or conversely, a decreased level in that GAG form in the subject in comparison with the control level may be indicative of good (or better prognosis). By way of another example, if a control level is the level of a given GAG form that is decreased in mccRCC, then an increased level of that GAG form in the subject in comparison to the control level may be indicative of good (or better) prognosis, or conversely, a decreased level in that GAG form in the subject in comparison with the control level may be indicative of poor (or poorer prognosis). GAG forms whose levels are altered in mccRCC (increased or decreased as the case may be) are described elsewhere herein, for example in Table A herein.

In some embodiments of the prognostic methods of the invention the control level of the marker (GAG form or score) is the level of the marker (GAG form or score) in a control (or reference) subject or sample, or control (or reference) population of subjects or samples (e.g. an average, for example the median, in a control population) that has RCC (e.g. ccRCC or mccRCC), and/or has had a former diagnosis of RCC (e.g. with no evidence of the disease at the time of acquisition of the sample), and/or has no current diagnosis of RCC (e.g. a healthy subject). Preferably, said control subject or population has a known outcome in terms of survival (e.g. overall survival or progression-free survival).

In some embodiments of the prognostic methods of the invention the control level of the marker (GAG form or score) is the level of the marker (GAG form or score) in a control (or reference) subject or sample, or control (or reference) population of subjects or samples (e.g. an average, for example the median, in a control population) that has RCC (e.g. ccRCC or mccRCC), and/or has had a former diagnosis of RCC (e.g. with no evidence of the disease at the time of acquisition of the sample). Preferably, said control subject or population has a known outcome in terms of survival (e.g. overall survival or progression-free survival).

In some embodiments of the prognostic methods of the invention the control level of the marker (GAG form or score) is the level of the marker (GAG form or score) in a control (or reference) subject or sample, or control (or reference) population of subjects or samples (e.g. an average, for example median, in the control population) that has ccRCC, and/or has had a former diagnosis of ccRCC (e.g. with no evidence of the disease at the time of acquisition of the sample). Preferably, said control subject or population has a known outcome in terms of survival (e.g. overall survival or progression-free survival).

In some embodiments of the prognostic methods of the invention the control level of the marker (GAG form or score) is the level of the marker (GAG form or score) in a control (or reference) subject or sample, or control (or reference) population of subjects or samples (e.g. an average, for example median, in the control population) that has mccRCC, and/or has had a former diagnosis of ccRCC (e.g. with no evidence of the disease at the time of acquisition of the sample). Preferably, said control subject or population has a known outcome in terms of survival (e.g. overall survival or progression-free survival).

In some embodiments of the prognostic methods of the invention the control level of the marker (GAG form or score) is the median (or other statistical average) level of the marker (GAG form or score) in a control population, e.g. a population of subjects (or samples) having RCC (preferably ccRCC, more preferably mccRCC) and/or subjects that have had a former diagnosis of RCC, ccRCC or mccRCC (e.g. with no evidence of the disease at the time of acquisition of the sample). Preferably, said control population (the individuals within the population) has a known outcome in terms of survival (e.g. overall survival or progression-free survival).

In some embodiments of the prognostic methods of the invention the control level of the marker (GAG form or score) is the median (or other statistical average) level of the marker (GAG form or score) in a control population, e.g. a population of subjects (or samples) having RCC (preferably ccRCC, more preferably mccRCC) and subjects that have had a former diagnosis of RCC, ccRCC or mccRCC (e.g. with no evidence of the disease at the time of acquisition of the sample). Preferably, said control population (the individuals within the population) has a known outcome in terms of survival (e.g. overall survival or progression-free survival).

In some embodiments of the prognostic methods of the invention the control level of the marker (GAG form or score) is the median (or other statistical average) level of the marker (GAG form or score) in a control population, e.g. a population of subjects (or samples) having RCC (preferably ccRCC, more preferably mccRCC). Preferably, said control population (the individuals within the population) has a known outcome in terms of survival (e.g. overall survival or progression-free survival).

In some embodiments of the prognostic methods of the invention the control level of the marker (GAG form or score) is the median (or other statistical average) level of the marker (GAG form or score) in a control population, e.g. a population of subjects (or samples) with no current diagnosis of RCC (preferably healthy subjects). Preferably, said control population (the individuals within the population) has a known outcome in terms of survival (e.g. overall survival or progression-free survival).

In some embodiments of the methods for the prognosis of metastatic ccRCC (mccRCC), the control level (or score) is the median level (or score) in a control population of subjects (or samples) comprising subjects having metastatic cancer (e.g. being treated with sunitinib or everolimus or other therapy for RCC) and subjects having had a former diagnosis of ccRCC (e.g. with no evidence of the disease at the time of acquisition of the sample).

In some embodiments, where the median level (or other average) (or score) in a control population is used as the control level, the population has at least 10, at least 20, at least 30, at least 40, at least 50 or at least 100 individual subjects. In one preferred embodiment, a control population has at least 20 individual subjects. In one preferred embodiment, a control population has at least 30 individual subjects.

In some such embodiments, at least 50%, at least 60%, at least 70%, at least 80%, at least 90% or 100% of the individual subjects (or samples) in the control (or reference) population have the disease to be prognosed (RCC, preferably ccRCC, more preferably mccRCC). In one preferred embodiment, at least 70% of the individual subjects (or samples) in the control population have the disease to be prognosed.

A useful population (cohort) of subjects for the establishment of a "median" control (or cut-off) level (or score) is described in Example 2 herein.

Control (or cut-off or threshold) levels (or scores) may vary depending on the nature of the individuals or populations used to derived the control level or score and/or the GAG form (GAG property) being analysed. A person skilled in the art could readily determine appropriate control levels or scores.

As described in Example 2 herein, an exemplary cut-off (or control) score when using the preferred plasma score formula described herein is 0.89. Thus, in some embodiments, subjects having a plasma score below 0.89 (or below any other appropriate cut-off score) have (or are predicted to have) a good prognosis (e.g. in terms of overall survival or progression-free survival), for example in comparison with a subject having a plasma score above 0.89 (or above any other appropriate cut-off score). Conversely, in some embodiments, subjects having a plasma score above 0.89 (or above any other appropriate cut-off score) have (or are predicted to have) a poor prognosis (e.g. in terms of overall survival or progression-free survival), for example in comparison with a subject having a plasma score below 0.89 (or below any other appropriate cut-off score).

As described in Example 2 herein, an exemplary cut-off (or control) score when using the preferred urine score formula described herein is 1.18. Thus, in some embodiments, subjects having a urine score below 1.18 (or below any other appropriate cut-off score) have (or are predicted to have) a good prognosis (e.g. in terms of overall survival or progression-free survival), for example in comparison with a subject having a urine score above 1.18 (or above any other appropriate cut-off score). Conversely, in some embodiments, subjects having a urine score above 1.18 (or above any other appropriate cut-off score) have (or are predicted to have) a poor prognosis (e.g. in terms of overall survival or progression-free survival), for example in comparison with a subject having a urine score below 1.18 (or below any other appropriate cut-off score).

Other cut-off (control) scores may include about 0.8, 0.9 or 1 for the preferred plasma scoring formula. Other cut-off (control) scores may include about 1.15 or 1.2 for the preferred urine scoring formula.

As discussed elsewhere herein, an altered (increased or decreased as the case may be) level or composition (or score) in comparison to a control level or composition (or score) is indicative of prognosis for (e.g. overall survival or progression-free survival prospects) for RCC (preferably for ccRCC, more preferably for mccRCC). When the preferred scoring formulae are used (plasma score and/or urine score), high (or higher) scores in comparison to the control (or cut-off) score (e.g. in comparison to the median score in a control or reference population) are predicative of poor (or poorer) prognosis (e.g. in terms of OS or PFS or RFS) and low (or lower) scores in comparison to the control (or cut-off) score (e.g. in comparison to the median score in a control or reference population) are indicative of good (or better) prognosis (e.g. in terms of OS or PFS or RFS).

A good (or better) prognosis may be a good (or better) prognosis relative to the prognosis for a control subject or control population. A poor prognosis may be poor (or worse) prognosis relative to the prognosis for a control subject or population.

Thus, a good (or better) prognosis may be a good (or better) prognosis relative to the average (e.g. median) prognosis for a control population, e.g. relative to the median survival (OS or PFS or RFS) for that population. Conversely, a poor (or worse) prognosis may be a poor (or worse) prognosis relative to the average (e.g. median) prognosis for a control population, e.g. relative to the median survival (OS or PFS or RFS) for that population.

Practitioners in this technical field would be able to establish what constitutes a good (or better) prognosis and what constitutes a poor (or worse) prognosis, for example by comparing the level of the marker (GAG form or score) for the subject (test subject) with a control level or score that has been obtained from a control (or reference) subject or population that has a known outcome or known probability of outcome (e.g. survival outcome such as death (time period until death) in the case of OS) or disease progression (time period until disease progression) in the case of PFS) wherein an alteration (increase or decrease as the case may be) in the level (or score) in the test subject relative to the control level is indicative of good (or better) prognosis (outcome or probability of outcome) or poor (or worse) prognosis (outcome or probability of outcome), as the case may be, relative to the control subject or control population.

In some embodiments, a good prognosis (e.g. in ccRCC subjects/patients such as mccRCC subjects/patients) in terms of progression-free survival is a ≥75% probability (e.g. ≥0%, ≥85%, ≥90%, ≥95% or 100% probability) that no disease progression will occur within a 6 month time period from the date of sampling, or a ≥70% probability (e.g. ≥75%, ≥80%, ≥85%, ≥90%, ≥95% or 100% probability) that no disease progression will occur within a 12 month time period from the date of sampling, or a ≥65% probability (e.g.

≥70%, ≥75%, ≥85%, ≥90%, ≥95% or 100% probability) that no disease progression will occur within a 24 month time period from the date of sampling, or a ≥65% probability (e.g. ≥70%, ≥80%, ≥85%, ≥90%, ≥95% or 100% probability) that no disease progression will occur within a 5 year period from the date of sampling.

In some embodiments, a poor prognosis (e.g. in ccRCC subjects/patients such as mccRCC subjects/patients) in terms of progression-free survival is a <75% probability that no disease progression will occur within a 6 month time period from the date of sampling, or a <70% probability that no disease progression will occur within a 12 month time period from the date of sampling, or a <65% probability that no disease progression will occur within a 24 month time period from the date of sampling, or a <65% probability that no disease progression will occur within a 5 year time period from the date of sampling.

In some embodiments, a good prognosis (e.g. in ccRCC subjects/patients such as mccRCC subjects/patients) in terms of overall survival is a ≥85% probability (e.g. ≥90%, ≥95% or 100% probability) that death will not occur within a 12 month time period from the date of sampling, or a ≥75% probability (e.g. ≥80%, ≥85%, ≥90%, ≥95% or 100% probability) that death will not occur within a 24 month time period from the date of sampling, or a ≥75% probability (e.g. ≥80%, ≥85%, ≥90%, ≥95% or 100% probability) that death will not occur within a 5 year time period from the date of sampling.

In some embodiments, a poor prognosis (e.g. in ccRCC subjects/patients such as mccRCC subjects/patients) in terms of overall survival is a <85% probability that death will not occur within a 12 month time period from the date of sampling, or a <75% probability that death will not occur within a 24 month time period from the date of sampling, or a <75% probability that death will not occur within a 5 year time period from the date of sampling.

Further probabilities of survival (OS or PFS) over a given time period may be derived from the Kaplan-Meier curves of Example 2/FIGS. 9-12 herein. In some such embodiments, further probabilities may be derived from Kaplan-Meier curves based on urine samples. In other such embodiments, further probabilities may be derived from Kaplan-Meier curves based on plasma samples.

In some preferred embodiments, time periods for survival (and e.g. associated probabilities such as those discussed above) are calculated from the date of sampling (date the sample was obtained). In other embodiments, time periods for survival (and e.g. associated probabilities such as those discussed above) may be calculated from the start date of treatment.

For prognostic methods any appropriate method may be used for the measurement of GAGs (as described elsewhere herein). In some embodiments, capillary electrophoresis with laser-induced fluorescence is used.

The features and discussion herein in relation to the method of screening for RCC (e.g. in relation to preferred GAG forms or combinations thereof for measurement) can be applied, mutatis mutandis, to prognostic methods of the present invention.

In one aspect, the present invention provides a method of detecting (or determining) the level and/or chemical composition of one or both of the glycosaminoglycans (GAGs) chondroitin sulfate (CS) and heparan sulfate (HS) in a body fluid sample, wherein said sample has been obtained from a subject.

In one aspect, the present invention provides a method of detecting the level and/or chemical composition of one or both of the glycosaminoglycans (GAGs) chondroitin sulfate (CS) and heparan sulfate (HS) in a patient, said method comprising:
    (a) obtaining a body fluid sample from a human patient; and
    (b) detecting the level and/or chemical composition of one or both of the glycosaminoglycans (GAGs) chondroitin sulfate (CS) and heparan sulfate (HS) in said sample.

The features and discussion herein in relation to the method of screening for RCC (e.g. method of diagnosing, method for prognosis etc.), for example in relation to preferred GAG forms or combinations thereof for measurement, can be applied, mutatis mutandis, to methods of detecting of the present invention.

Figure 1B:
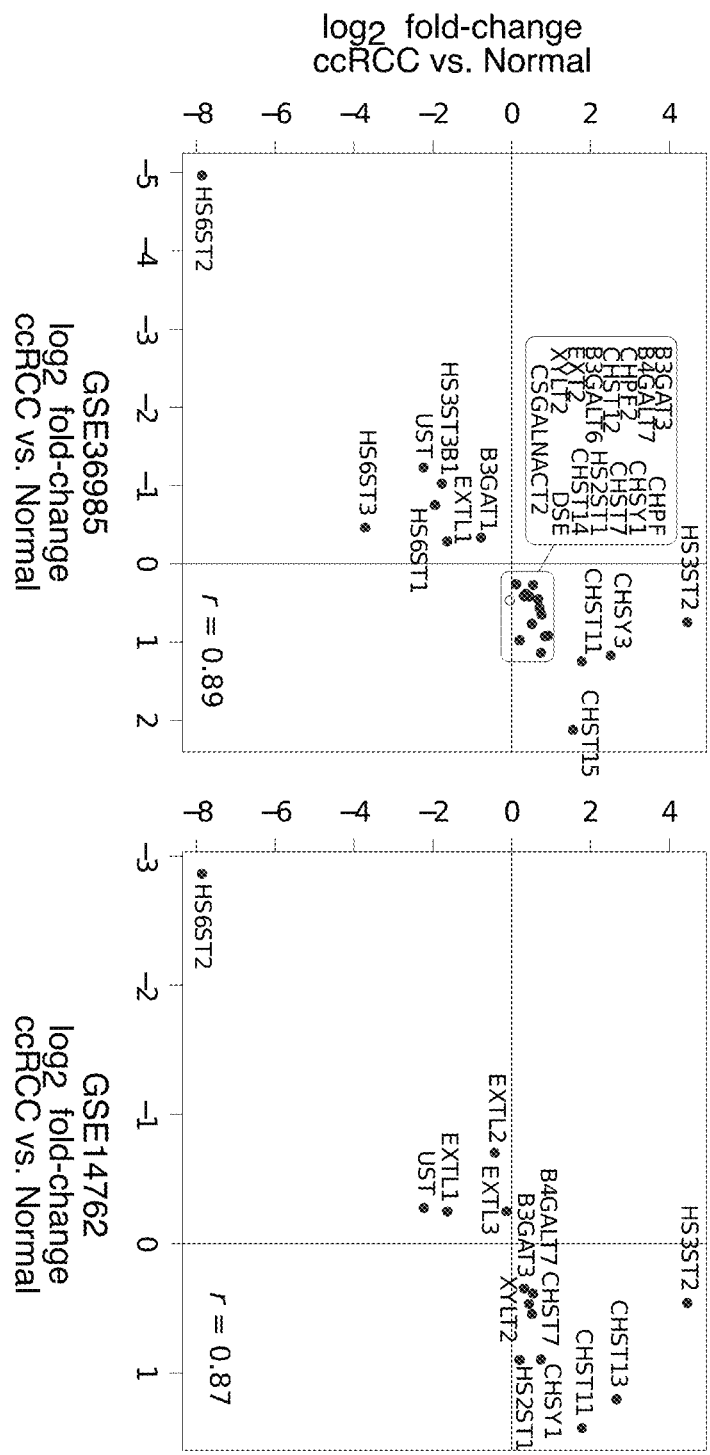

The invention will be further described with reference to the following non-limiting Examples with reference to the following drawings in which:

FIGS. 1A-1B: Coordinated regulation of glycosaminoglycan biosynthesis in ccRCC vs. tumor-adjacent normal kidney tissue. FIG. 1A) Pathway-view of glycosaminoglycan biosynthesis in ccRCC. Each box shows the enzyme(s) carrying out a given reaction in the pathway. For clarity, enzyme names are additionally stated beside some of the boxes. The color represents the $\log_{10}$-fold-change in ccRCC vs. non-tumor tissue for the enzyme-coding gene, while the symbol next to each box reports the significance for the corresponding gene regulation (in terms of false discovery rate). For clarity, each of the colors has also been given a letter identifier (A, B, C, D, E or F) and these identifiers are stated beside the boxes, as appropriate. The pathway has been drawn according to KEGG gene associations (note that genes related to dermatan sulfate biosynthesis or sulfation at C3 in heparan sulfate are not shown, the latter event being rarely observed. Solid arrows indicate the addition of a molecule, dashed lines indicate the conversion of a molecule, and dotted lines indicate the final disaccharide composition up to that point. FIG. 1B) Correlation of gene expression $\log_2$ fold-changes in the glycosaminoglycan biosynthesis pathway between TCGA samples (y-axis) and two independent studies (GSE36986 and GSE14762).

Figure 2:
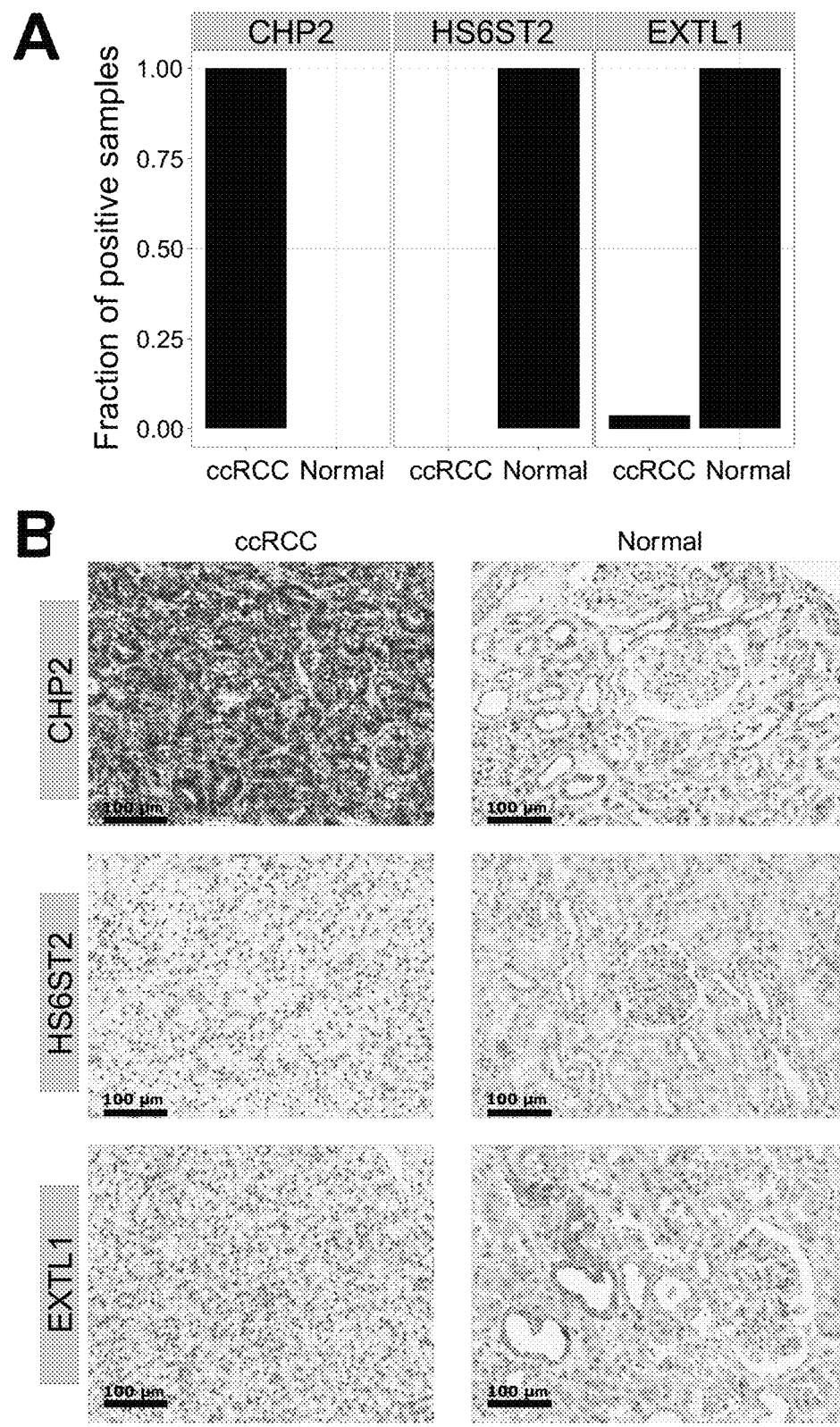

FIG. 2: Immunohistochemical staining of three proteins in glycosaminoglycan biosynthesis in ccRCC vs. normal kidney tissue. A) Fraction of samples positive for CHPF2, HS6ST2, and EXTL1 in ccRCC (21 to 27 tissue samples) vs. normal kidney (2 samples). The results are presented as the consensus of staining performed in duplicates. B) Staining for CHPF2, HS6ST2, and EXTL1 in representative ccRCC and normal samples.

Figure 3A:
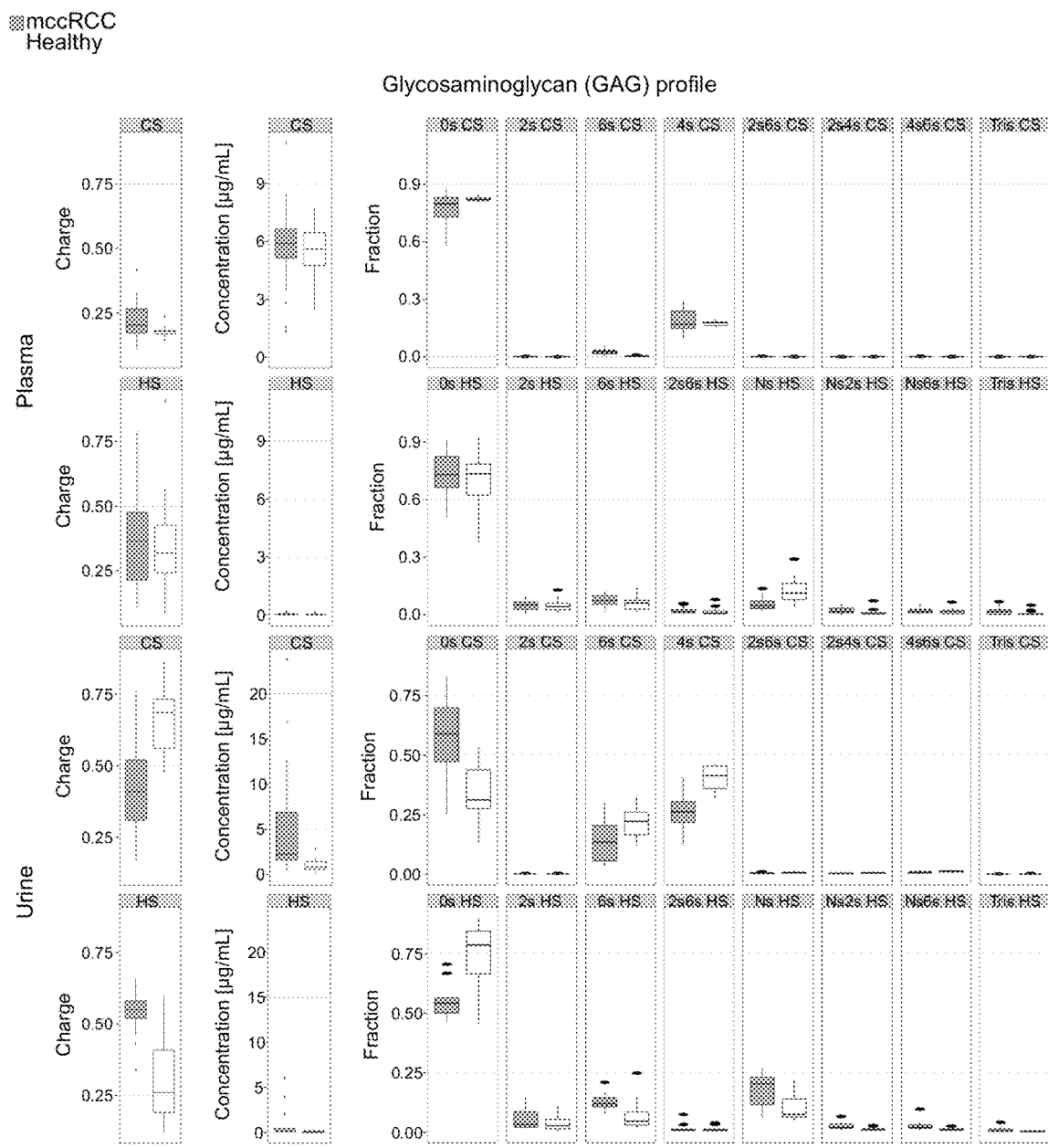
Figure 3B:
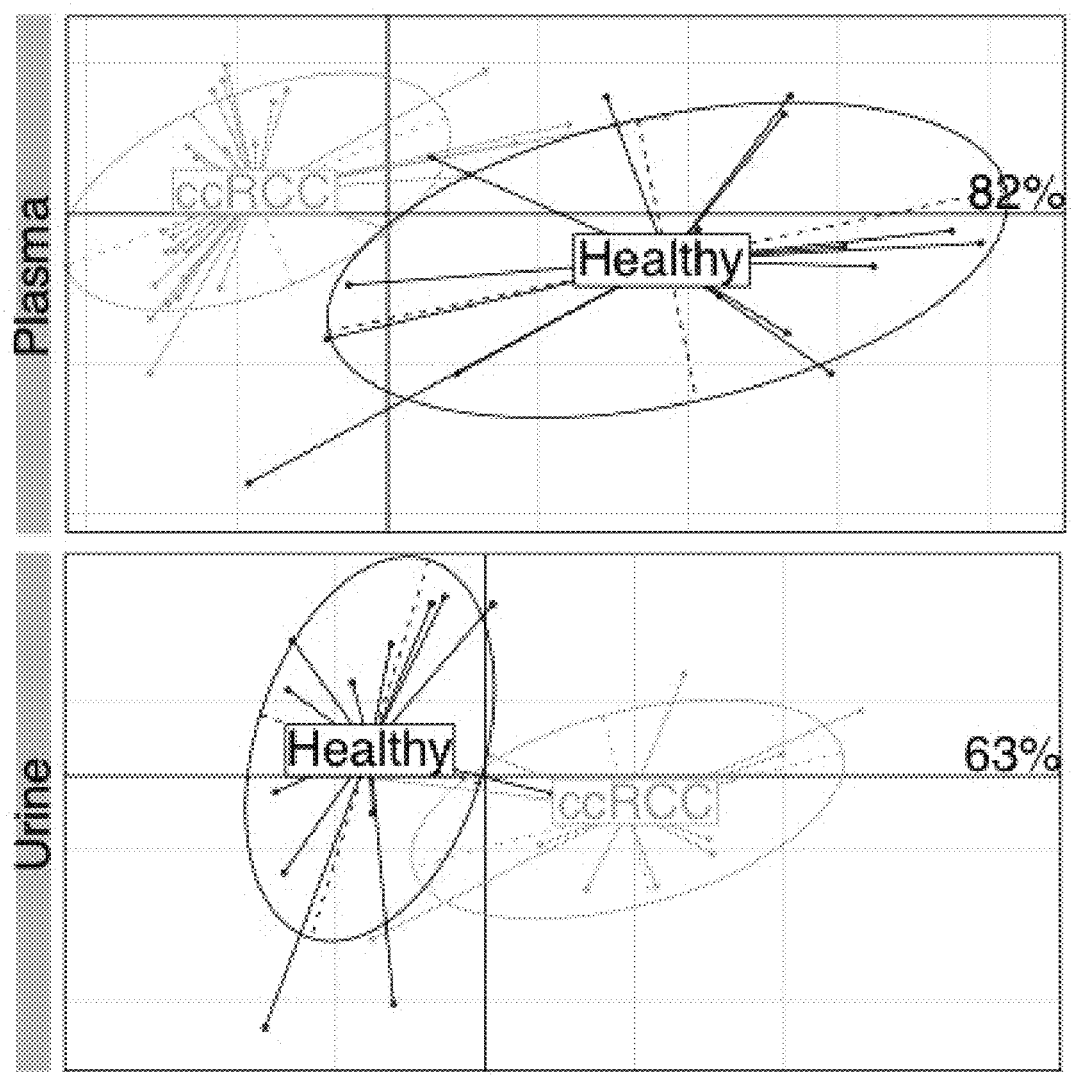

FIGS. 3A-3B: The glycosaminoglycan plasma and urine profiles of mccRCC (grey boxes) and healthy (white boxes) patients. FIG. 3A) Each profile comprises 18 independent measurements of GAGs (9 related to CS and 9 related to HS), which refer to the total concentration and the disaccharide composition, plus other dependent measurements such as the charge. FIG. 3B) Principal component analysis of mccRCC versus healthy GAG profiles using measurements from plasma (top) or urine (bottom).

Figure 4:
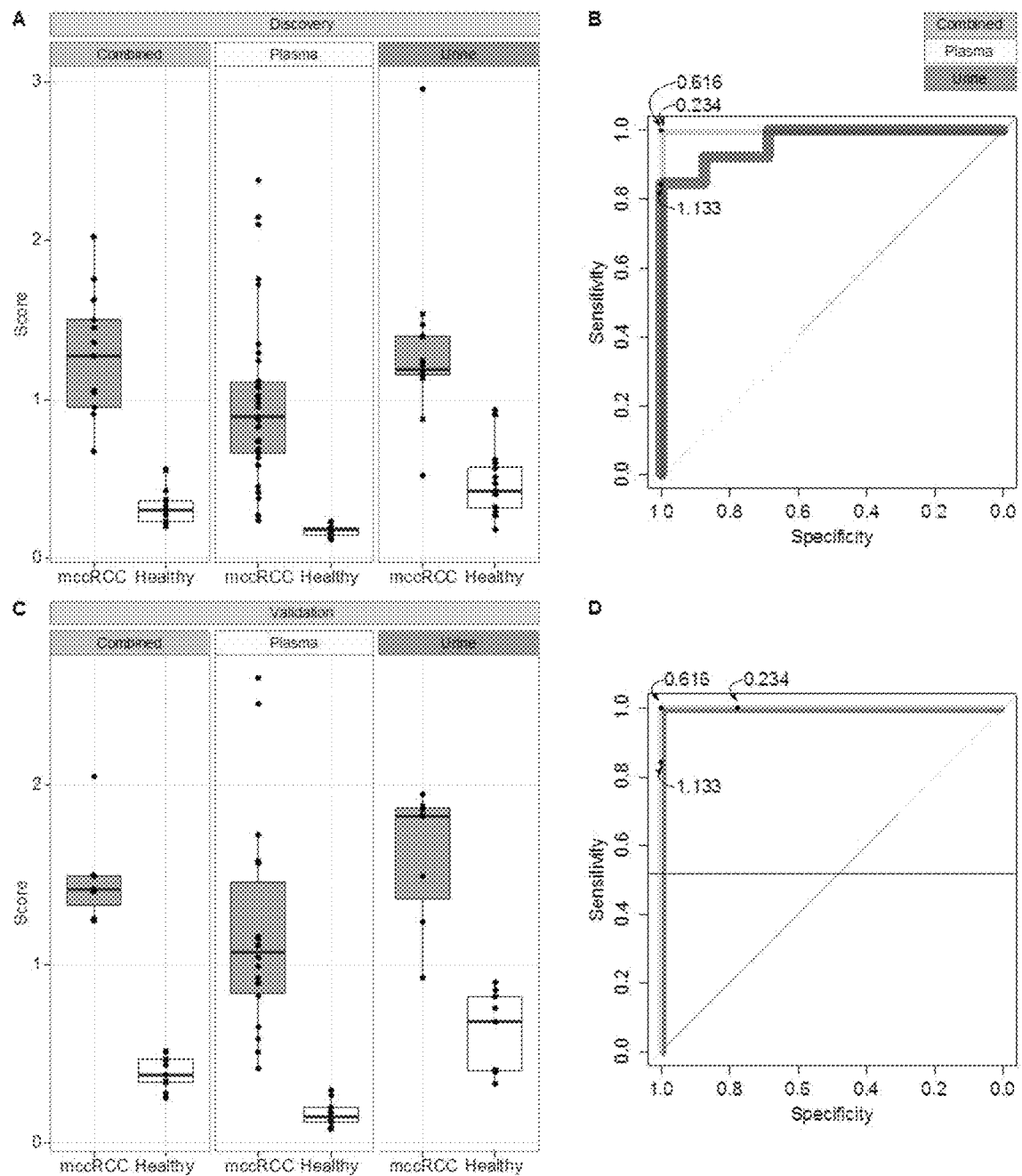

FIG. 4: The glycosaminoglycan profile can be summarized in three scores (based on measurements in the plasma, urine, or both) that can accurately predict occurrence of mccRCC. A) Plasma, urine, and combined scores in mccRCC patients (grey boxplots) and healthy individuals (white boxplots) belonging to the discovery cohort (34 samples vs. 17, respectively). B) Receiver-operating-characteristic (ROC) curves in the classification of samples of the discovery cohort as either mccRCC or healthy based on the combined, plasma, and urine scores. For each marker, an optimal cut-off scores that maximizes the positive predictive value is indicated. C) Plasma, urine, and combined scores in mccRCC patients (grey boxplots) and healthy individuals (white boxplots) belonging to the validation cohort (18 samples vs. 9, respectively). D) ROC curves in the classification of samples of the validation cohort as either mccRCC or healthy based on the combined, plasma, and urine scores.

Figure 5:
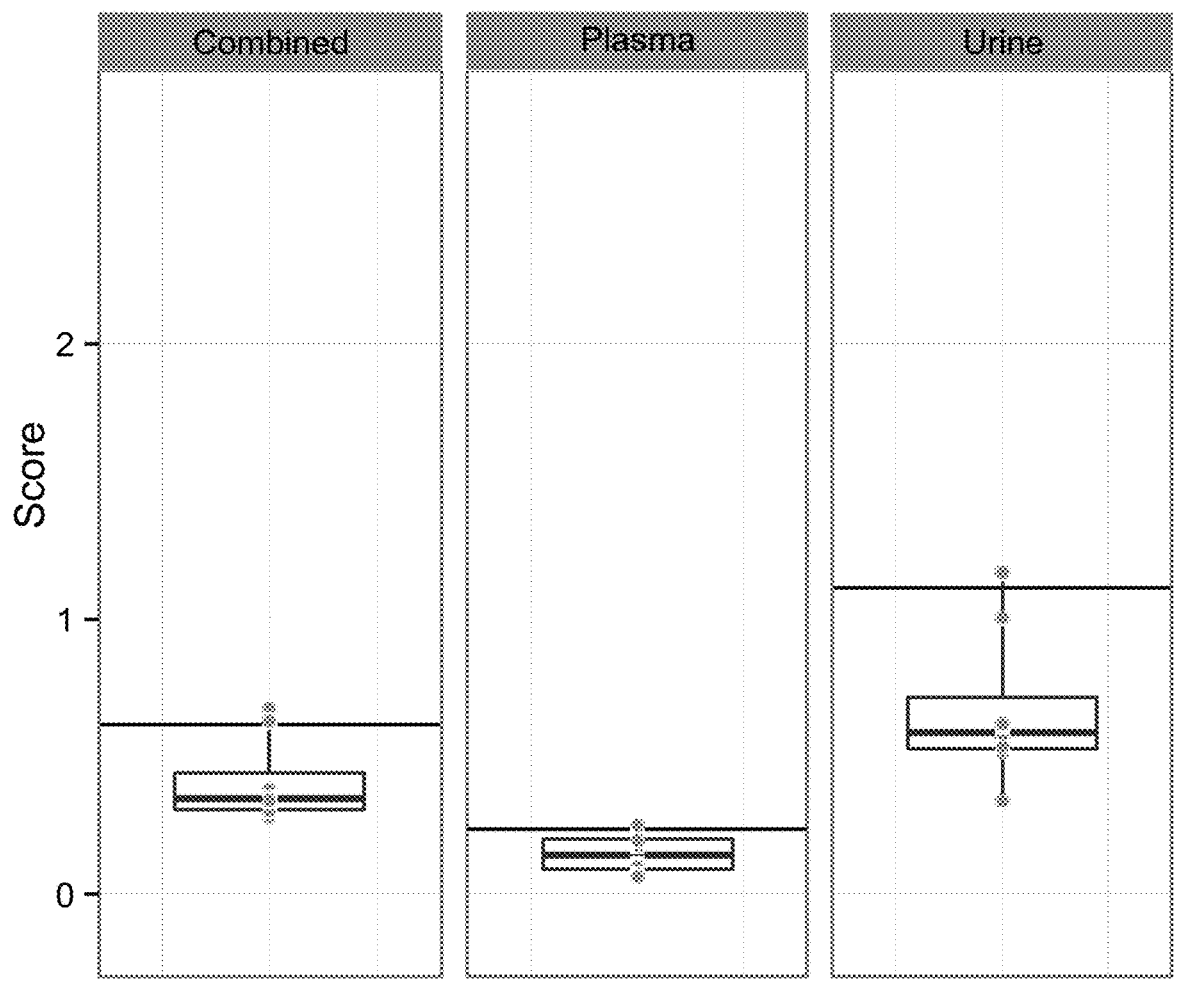

FIG. 5: Combined, plasma, and urine scores in subjects previously diagnosed with mccRCC but with no evidence of disease at the time of sampling. The horizontal lines represent the optimal cut-off scores at which a subject is classified as either mccRCC or healthy.

Figure 6:
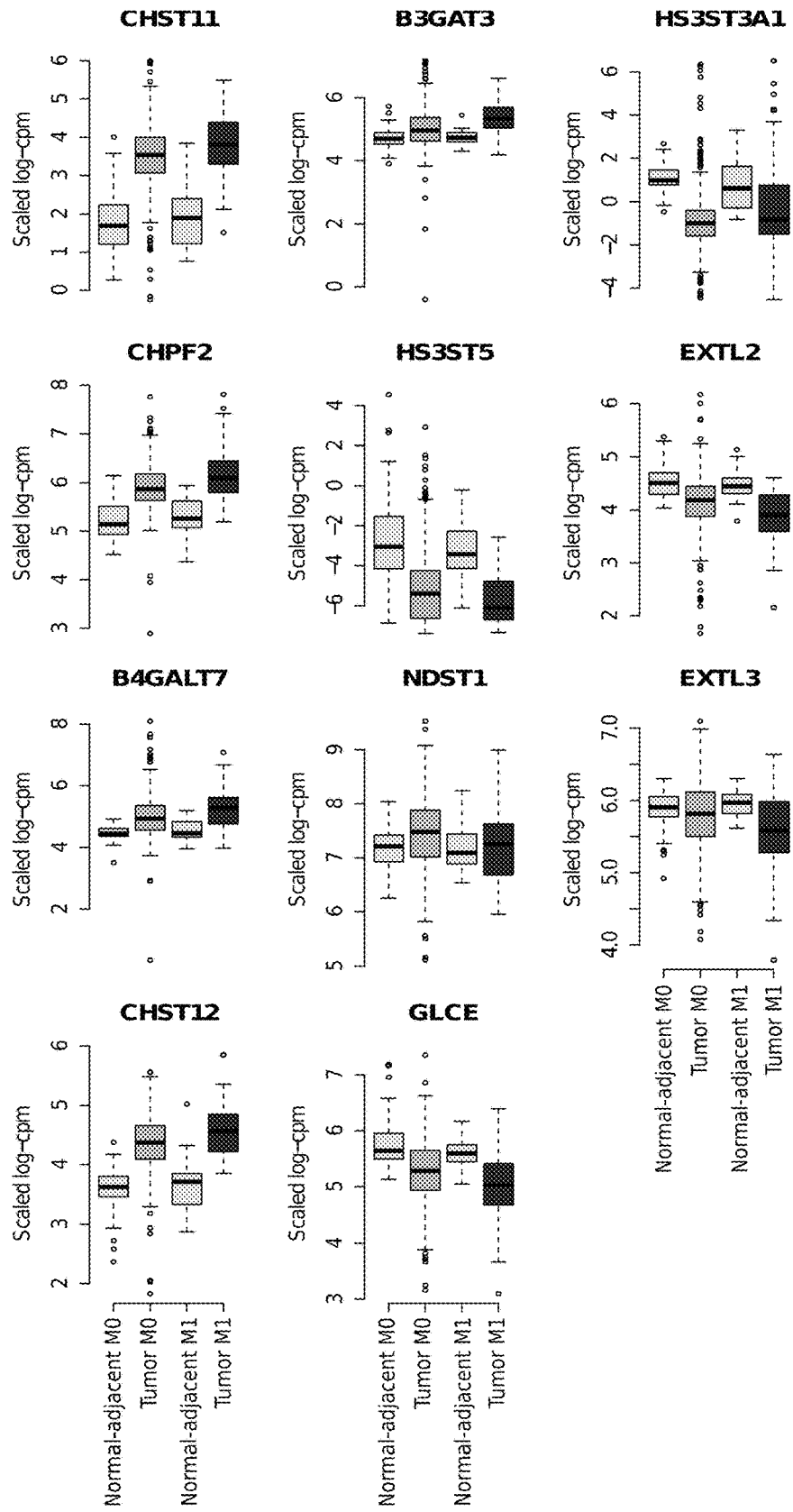

FIG. 6: Boxplots of gene expression for genes involved in glycosaminoglycan biosynthesis in ccRCC and tumor-adjacent normal samples, binned according to the sample metastatic status. The effect of metastasis (black boxplots) on GAGs genes has been estimated using linear regression. The boxplots above illustrate that metastasis exacerbate up-regulation of chondroitin sulfate associated genes and down-regulation of heparan sulfate associated genes (false discovery rate <5%). Legend: light grey—normal tissue adjacent to either metastatic (M1) or not-metastatic (M0) ccRCC; dark grey—not metastatic (M0) ccRCC; black—metastatic (M1) ccRCC.

Figure 7:
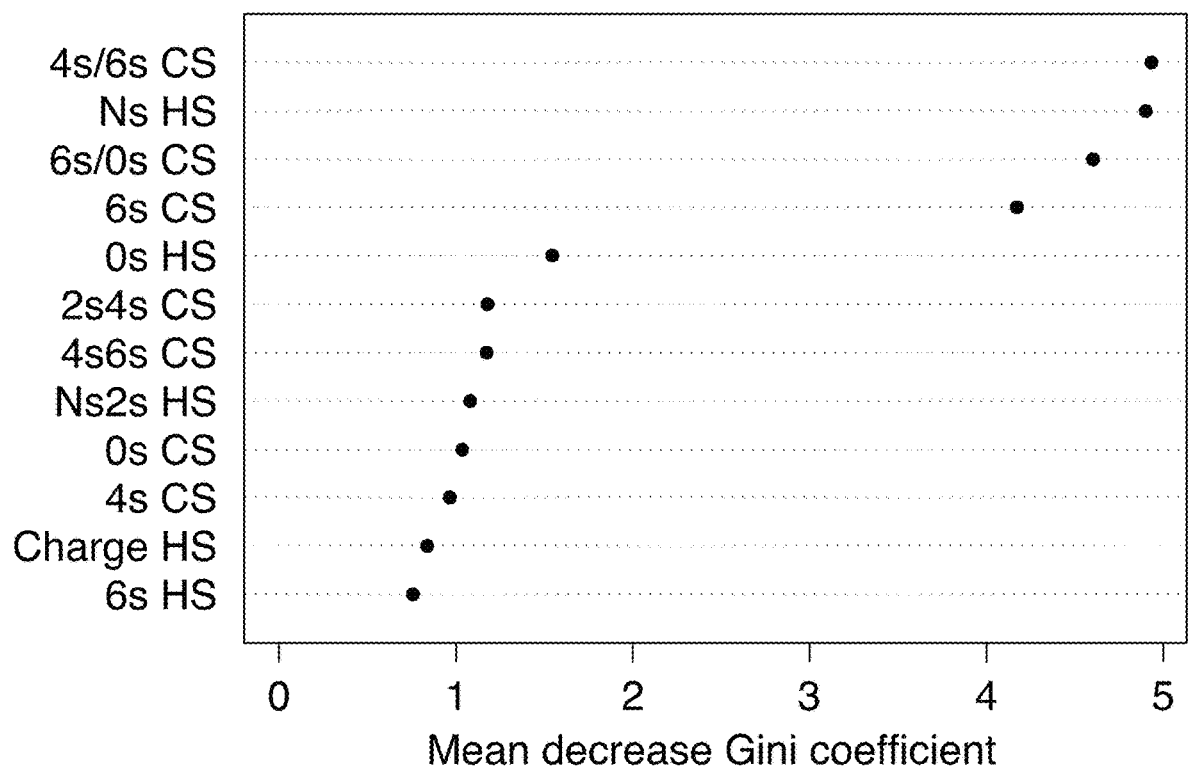

FIG. 7: Ranking of the plasmatic GAG properties in terms of decreased accuracy of a random forest classifier when the property is omitted (the decrease in accuracys is measured as mean decrease in the Gini coefficient). The classifier was trained on GAG properties of plasma samples. Only the 12 best properties are shown.

Figure 8:
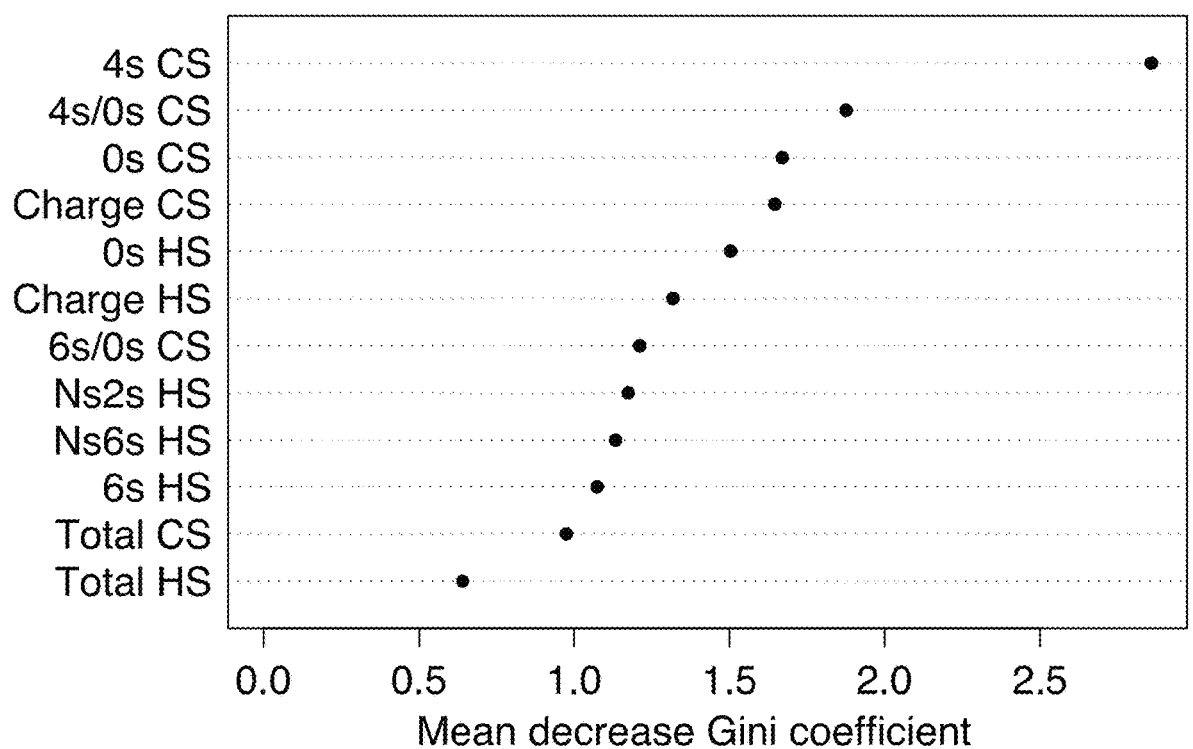

FIG. 8: Ranking of the urinary GAG properties in terms of decreased accuracy of a random forest classifier when the property is omitted (the decrease in accuracys is measured as mean decrease in the Gini coefficient). The classifier was trained on GAG properties of urine samples. Only the 12 best properties are shown.

Figure 9:
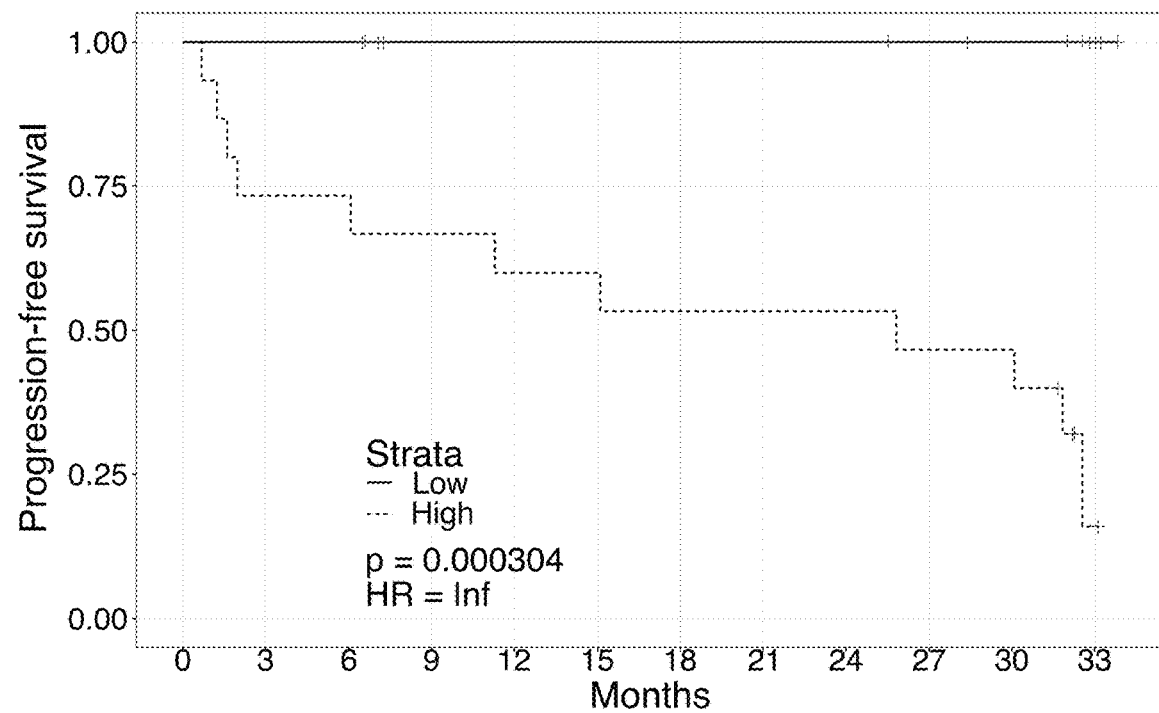
Figure 9:
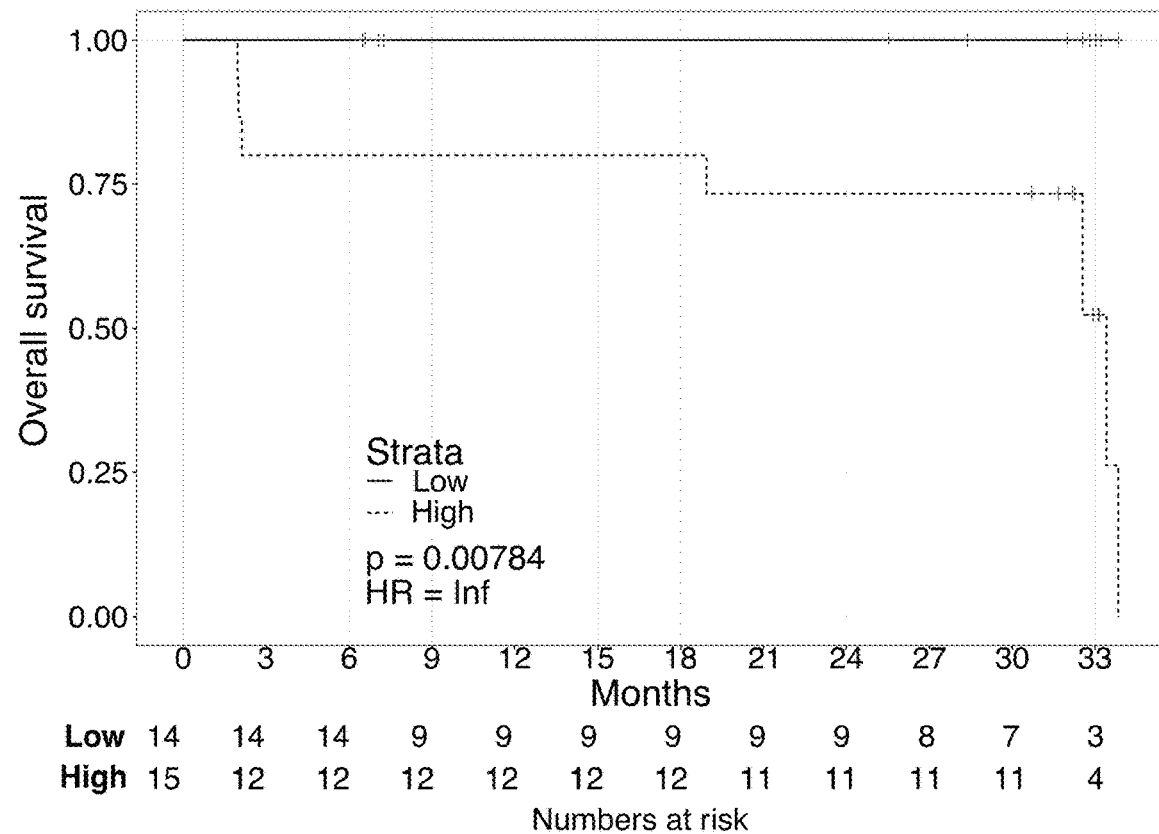

FIG. 9: Kaplan-Meier curves for PFS (top) or OS (bottom) in ccRCC patients stratified according to urine biomarker score level at follow-up. The prospective cohort of patients (N=29) was classified as "Low" (solid) versus "High" (dashed) biomarker score at the time of sampling. Censored data are displayed as grey crosses (short vertical-ticks). PFS: Progression-free survival. OS: Overall survival.

Figure 10:
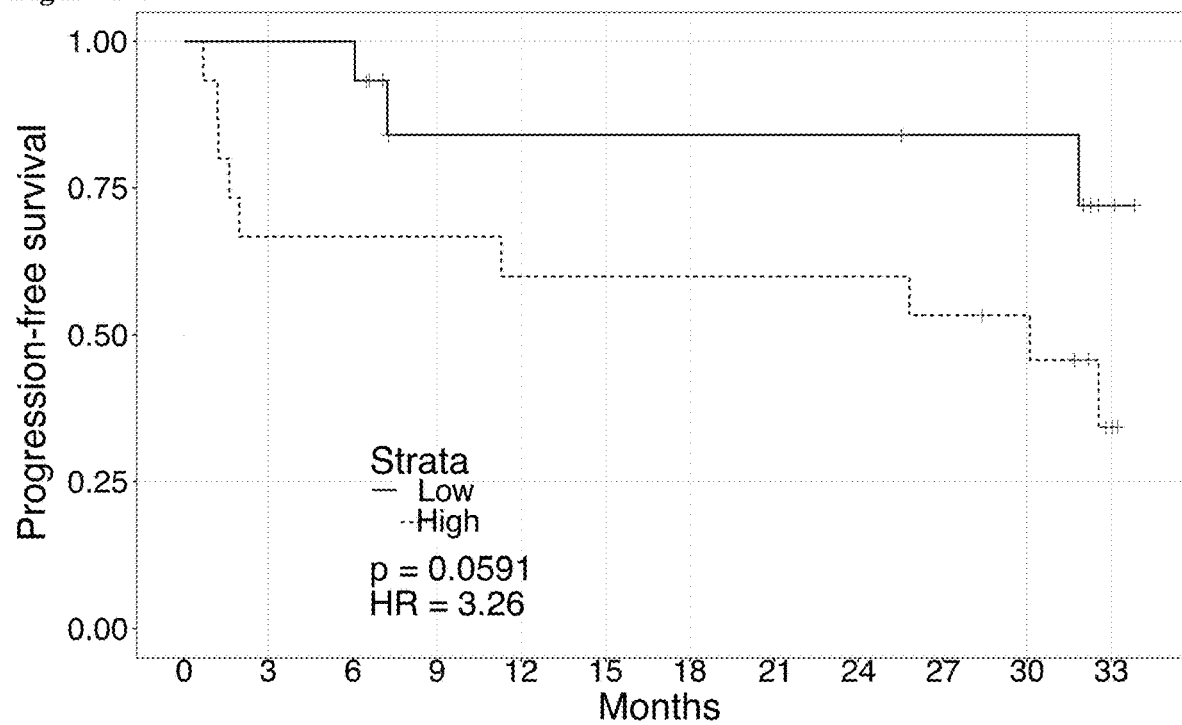
Figure 10:
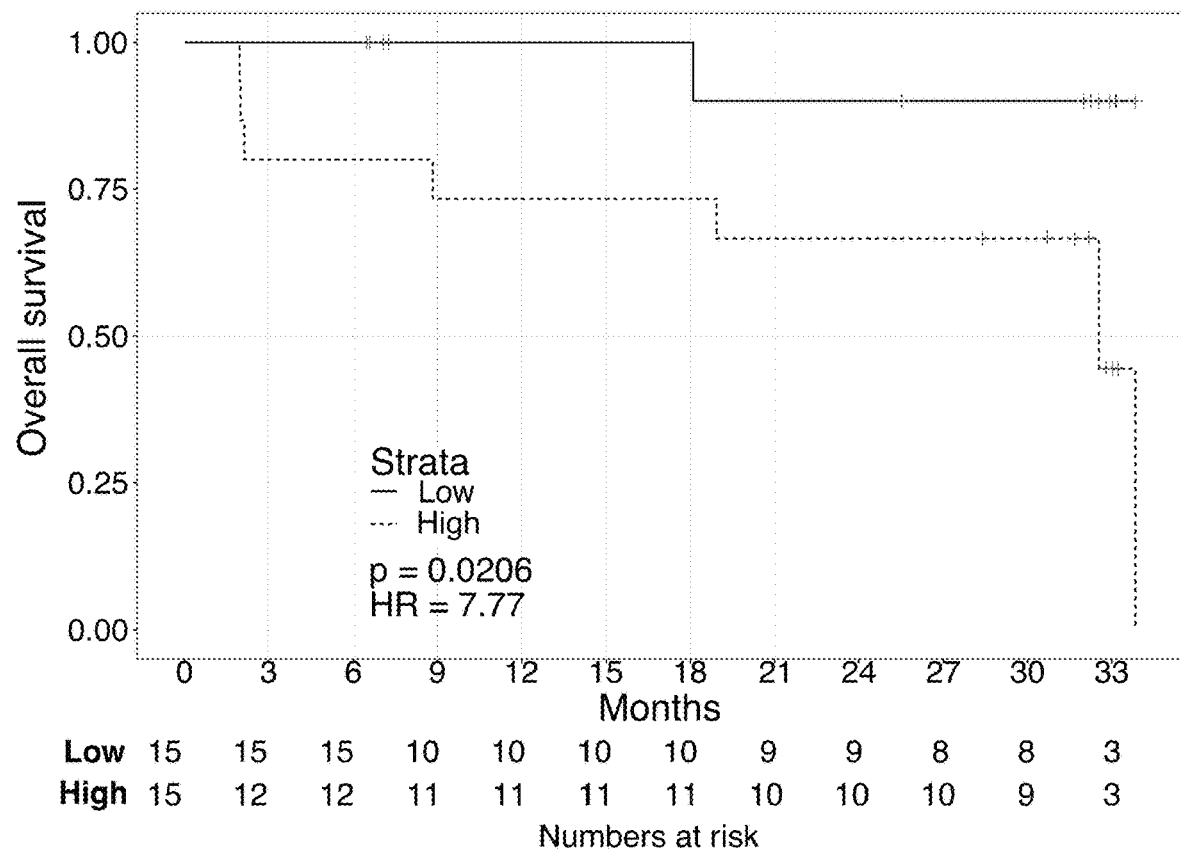

FIG. 10: Kaplan-Meier curves for PFS (top) or OS (bottom) in ccRCC patients stratified according to plasma biomarker score level at follow-up. The prospective cohort of patients (N=30) was classified as "Low" (solid) versus "High" (dashed) biomarker score at the time of sampling. Censored data are displayed as grey crosses (short vertical ticks). PFS: Progression-free survival. OS: Overall survival.

Figure 11A:
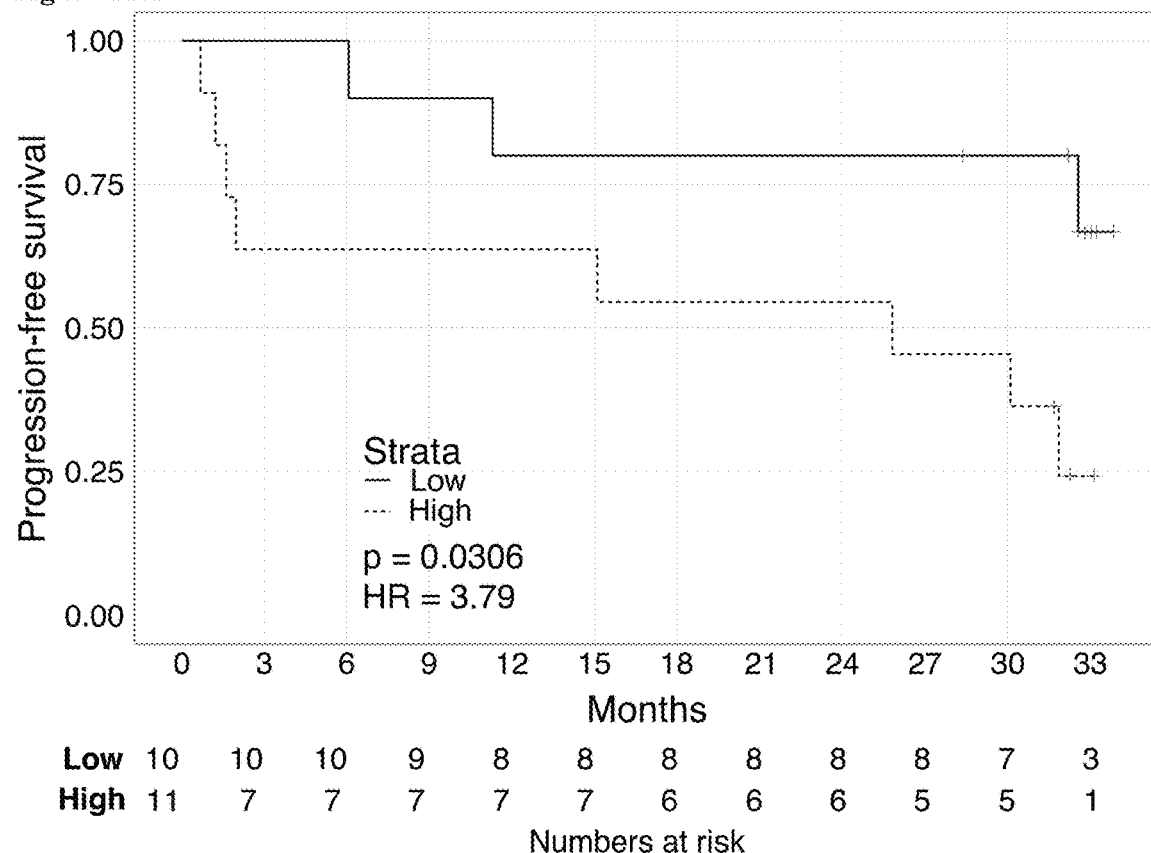
Figure 11A:
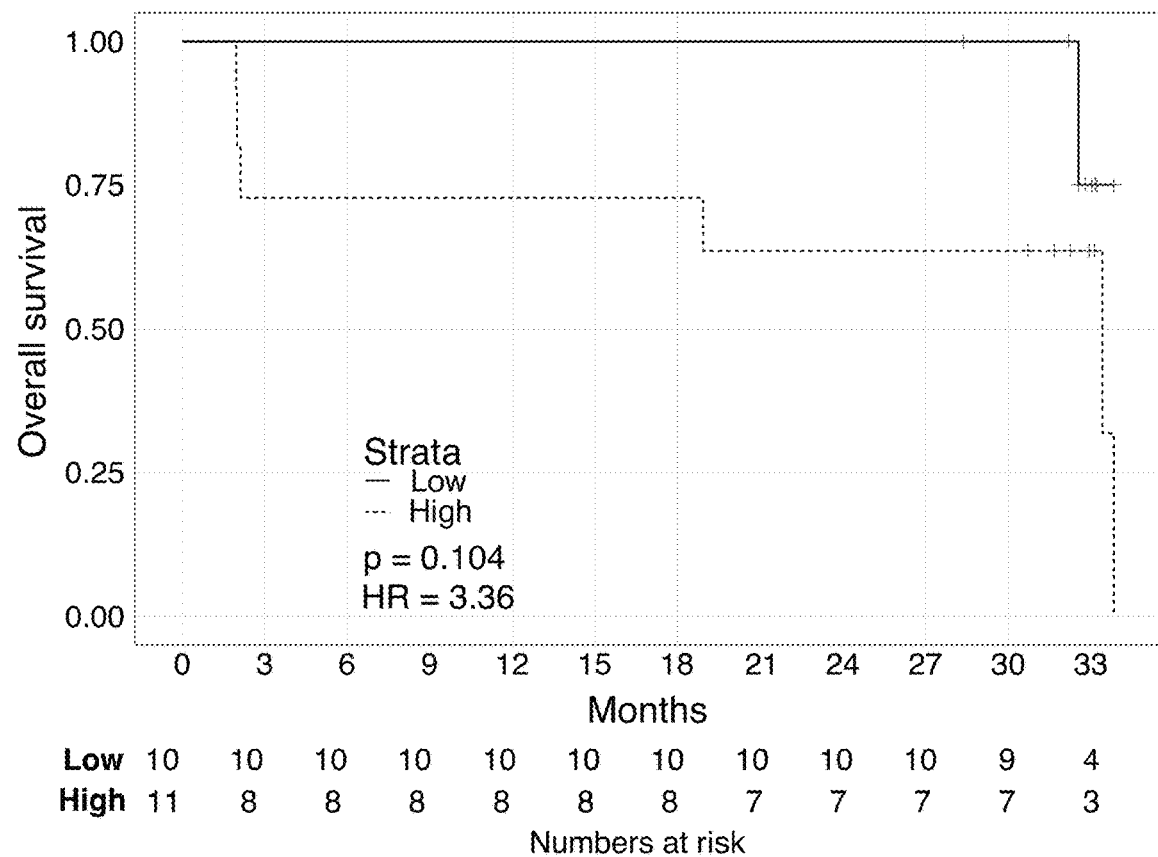
Figure 11B:
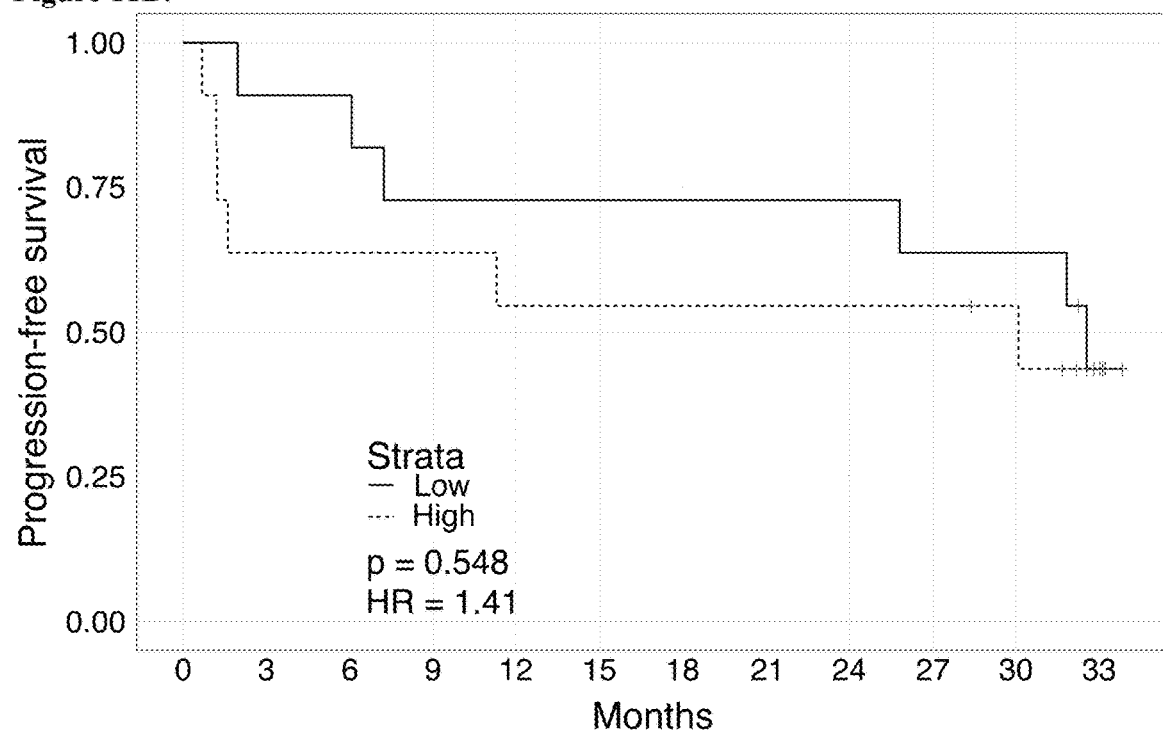
Figure 11B:
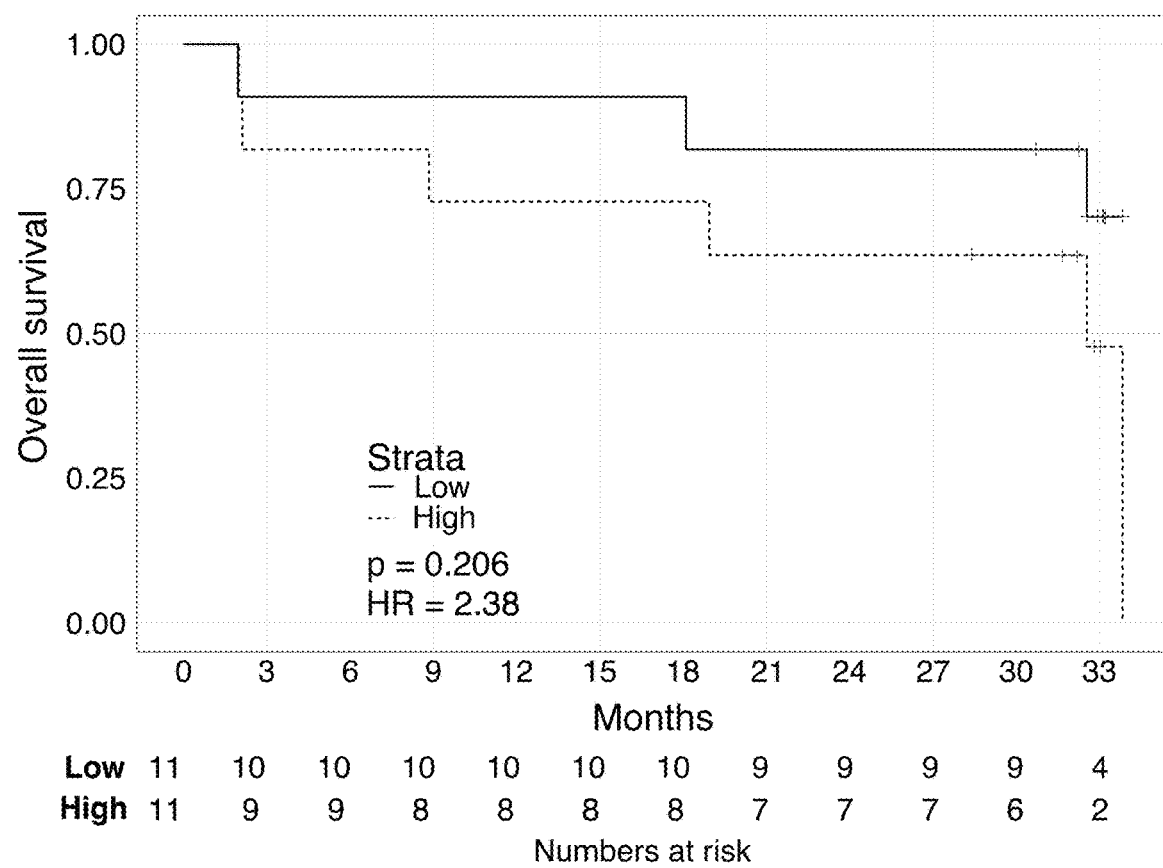

FIGS. 11A-11B: Kaplan-Meier curves for PFS (top) or OS (bottom) limited to patients with current diagnosis of metastatic ccRCC at follow-up stratified according to the urine (FIG. 11A) or plasma (FIG. 11B) biomarker score level at follow-up. The prospective cohort of patients (N=23) was classified as "Low" (solid) versus "High" (dashed) biomarker score at the time of sampling. Censored data are displayed as grey crosses (short vertical-ticks). PFS: Progression-free survival. OS: Overall survival.

Figure 12A:
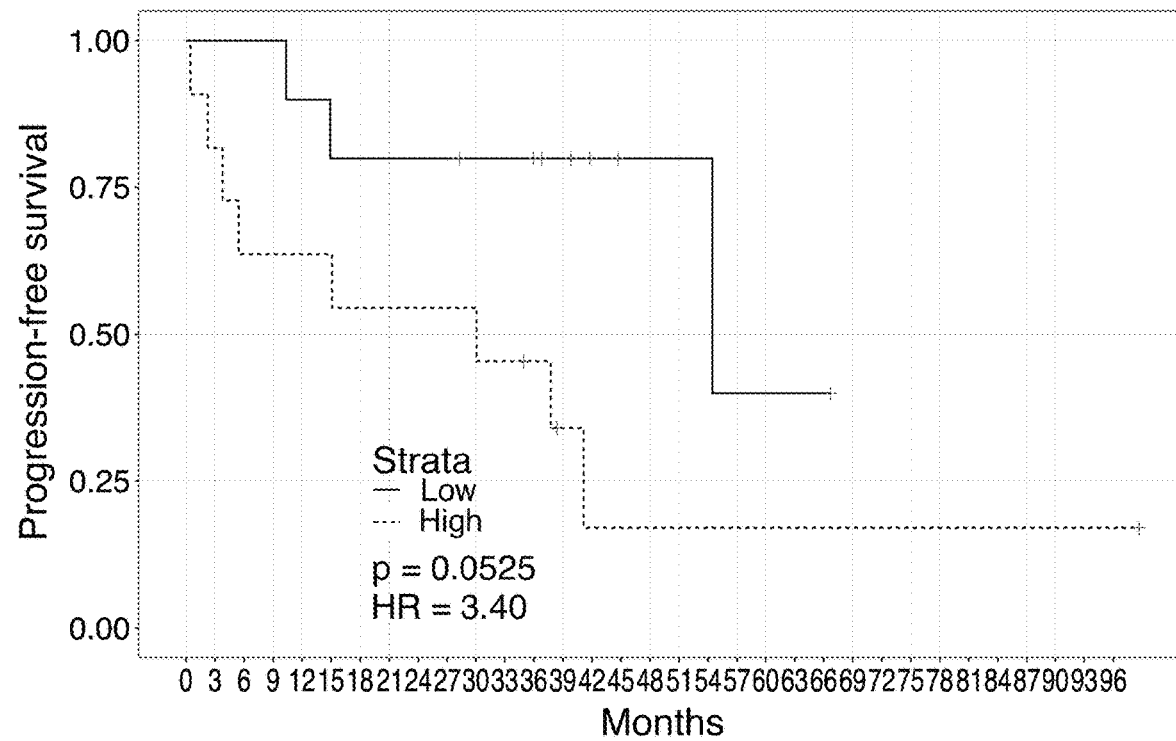
Figure 12A:
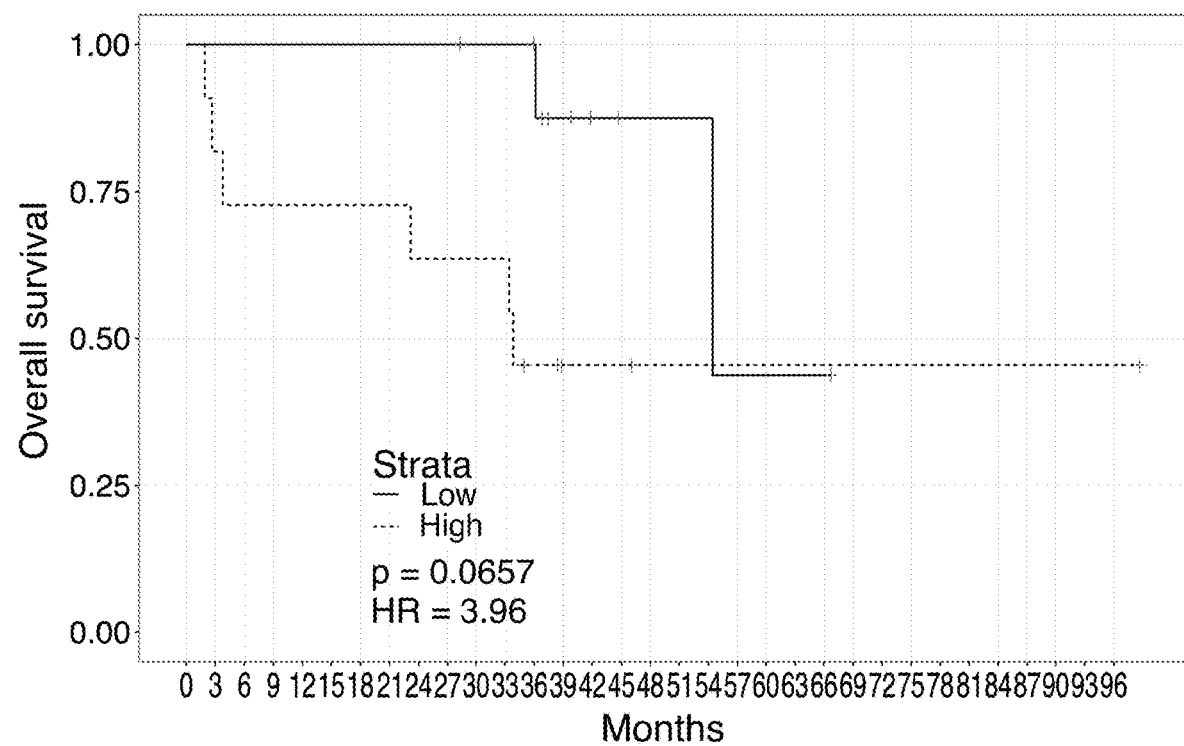
Figure 12B:
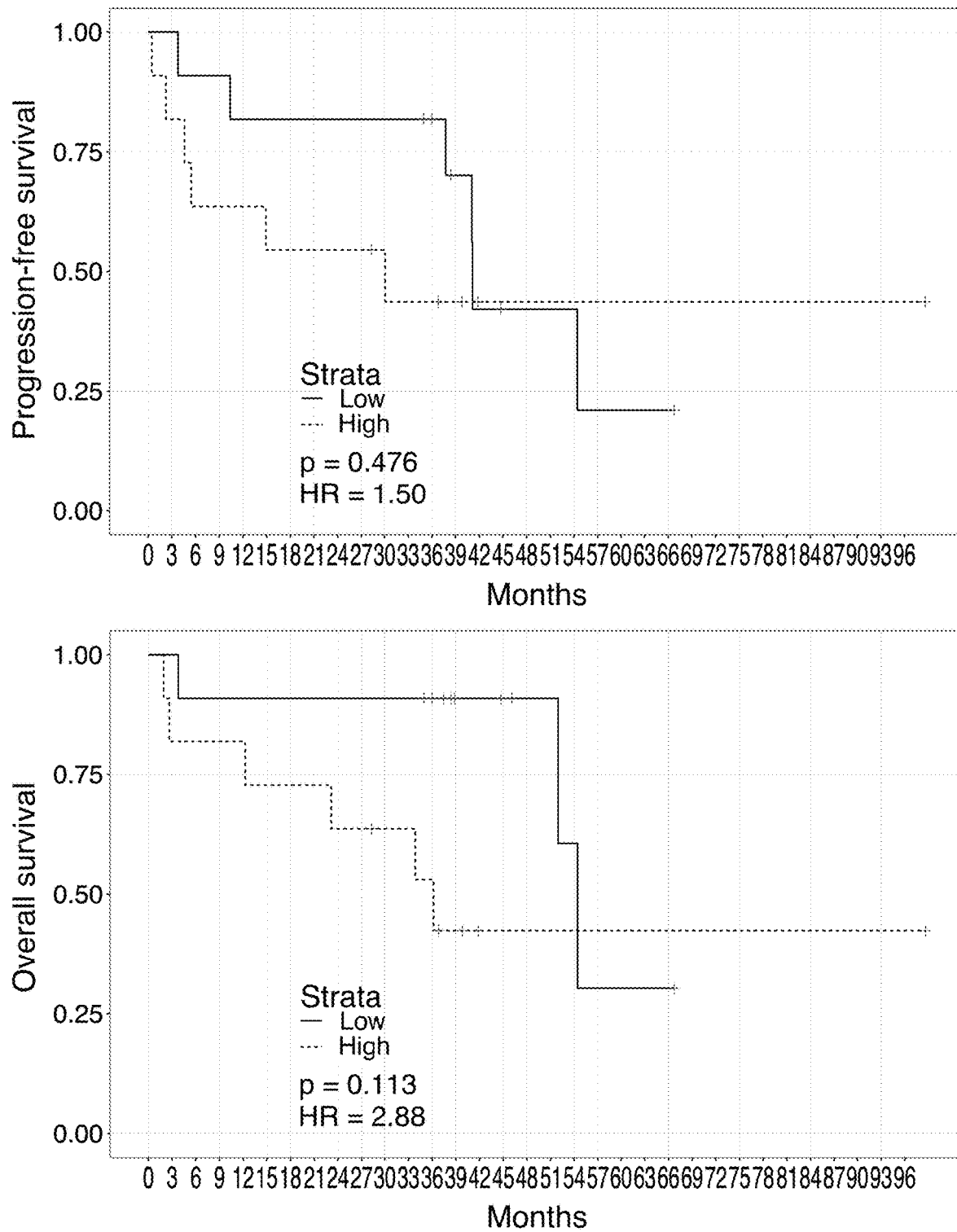

FIGS. 12A-12B: Kaplan-Meier curves for PFS (top) or OS (bottom) calculated from the start date of the treatment in ccRCC patients stratified according to the urine (FIG. 12A) or plasma (FIG. 12B) biomarker score level at follow-up. The prospective cohort of patients (N=23) was classified as "Low" (solid) versus "High" (dashed) biomarker score at the time of sampling. Censored data are displayed as grey crosses (short vertical-ticks). PFS: Progression-free survival. OS: Overall survival.

Figure 13:
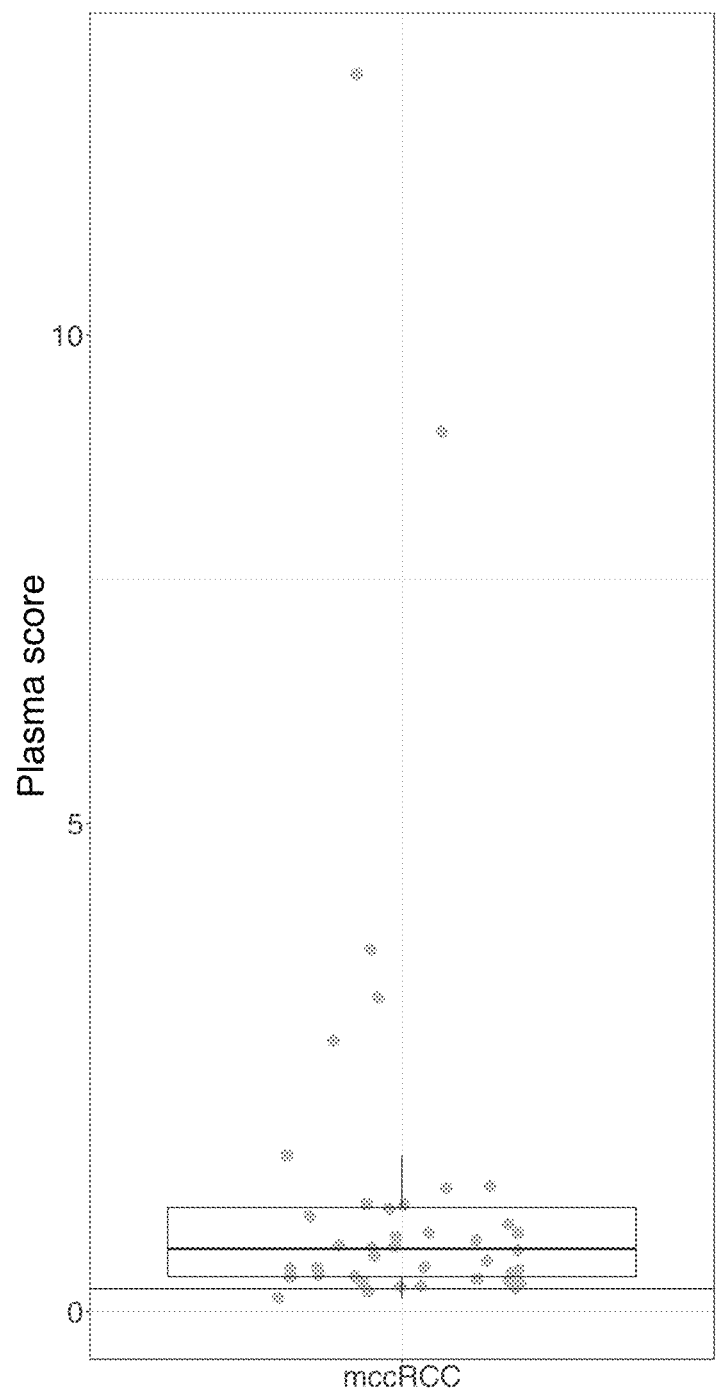

FIG. 13: Boxplot of plasma scores in 40 samples taken from subjects with diagnosis of metastatic ccRCC at the time of sampling. The horizontal line defines the previously defined cutoff score above which a subject is classified as having metastatic ccRCC.

EXAMPLES

Example 1

Clear cell renal cell carcinoma (ccRCC) is the most common form of kidney cancer. As part of the invention described herein, the inventors used genome-scale metabolic modeling to pinpoint unique metabolic reprogramming in ccRCC. Contrary to six other tested cancers, the inventors discovered a strong coordinated regulation of glycosaminoglycan (GAG) biosynthesis only in ccRCC, both at the gene expression and protein level. More specifically, the inventors measured 18 independent GAG properties in plasma and urine samples of 34 mccRCC patients and 16 healthy individuals. These former GAG profiles were distinctively altered in mccRCC. Based on these data, the inventors then designed three GAG markers that distinguished mccRCC from healthy individuals with an accuracy ranging from 82.7% to 100%. A positive predictive value ranging from 90% to 100% was further validated in an independent cohort of 18 mccRCC patients and 9 healthy individuals. In addition, these GAG bio-markers were predictive independent of age, gender, BMI, or dietary intake. Thus, in summary, the results described herein demonstrate that a coordinated regulation of GAG biosynthesis takes place in ccRCC and that GAG profiling in accessible fluids is suitable for diagnosis of mccRCC.

Experimental Procedures
Gene Expression Analysis

RNAseq gene expression profiles for 481 ccRCC primary tumor and 71 tumor-adjacent normal-like samples were retrieved at The Cancer Genome Atlas (TCGA). Differential gene expression analysis for ccRCC vs. non-tumor was performed using voom (Law et al., 2014). 2090 genes with no annotation (3%) or no more than 10 counts in less than 10% of the samples (7%) were discarded. The effect of metastasis was accounted by adding the metastatic status of each sample as a covariate in the linear model used in voom. Two independent microarray-generated datasets where retrieved in GEO (GSE36895 and GSE14762) and the differential expression analysis for ccRCC vs. non-tumor was performed using limma (Smyth, 2004). The significance for changes in gene expression using either RNAseq or microarray data was tested using empirical Bayes estimation on a linear model for a given comparison (in the case of RNAseq the count variance was moderated as proposed in voom (Law et al., 2014)). Consensus gene-set enrichment analysis (GSA) using piano (Varemo et al., 2013) was performed using as gene-sets either KEGG pathways or metabolites (i.e., a gene-set is the list of reaction-encoding genes that involve a given metabolite, where the gene-set p-value is defined as the median p-value for the following GSA methods: Fisher's test, Stouffer's test, reporter test, tail-strength test, mean, and median. The significance of a gene-set for each GSA method was tested using a permutation test by shuffling gene labels 10,000 times. Gene-set relatedness between gene-sets was computed in terms of the underlying network using Kiwi (Väremo et al., 2014), where gene-set were considered related if the mutual shortest path length is lesser than 2 in the network (to increase interpretability, gene-sets with more than 10 genes were neglected). In the case of metabolites, the gene-set network was extracted from the genome-scale metabolic model HMR2 (Agren et al., 2014). The gene-set network resulting as most significant from this analysis was subject to manual inspection and curation, as it represents the metabolic sub-network most regulated in the comparison of interest (i.e. ccRCC vs. non-cancerous adjacent kidney). All the above methods were implemented using the respective R-packages, except Kiwi that is a Python module.

Immunohistochemical Staining

A tissue microarray containing 32 ccRCC samples and 2 normal kidney samples in duplicates was prepared and used for immunohistochemistry. An experienced urological pathologist selected all cases. The ethical approval was granted by the ethical committee at Lund University (LU289-07). Tissue sections of 4 µm were deparaffinized and rehydrated according to standard protocols. Antigen retrieval was performed using pressure cooking of the samples for 20 minutes in 10 mmol/L citrate buffer, pH 6.0. Immunohistochemical staining was performed using a Dako Techmate 500 unit, according to the manufacturer's instructions (Dako, Glostrup, Denmark). Antibodies and dilutions used were HPA020992 (CHP2 1:35), HPA034625 (HS6ST2 1:125) and HPA037749 (EXTL1 1:35), all from Atlas Antibodies AB, Stockholm, Sweden. Only tumor samples where both duplicates could be scored were included in the analysis (21 for CHP2, 32 for HS6ST2 and 27 for EXTL1).

Blood and Urine Sample Collection

In the discovery cohort, plasma and urine samples were obtained from 34 patients with metastatic clear cell renal carcinoma in two sites, IOV-IRCCS, Padova, Italy and Sahlgrenska University Hospital, Göteborg, Sweden. For 21 patients, only plasma samples were obtained. A control group was formed using 16 healthy individuals without any renal or liver malignancy, nor inflammatory pathologies. In the validation cohort, plasma and urine samples were obtained from 18 patients with metastatic clear cell renal carcinoma in two sites, IOV-IRCCS, Padova, Italy and Sahlgrenska University Hospital, Göteborg, Sweden. For 11 patients, only plasma samples were obtained. A control group was formed using 9 healthy individuals without any renal or liver malignancy, nor inflammatory pathologies. All subjects provided written informed consent. Baseline characteristics are described in Table C. The present observational study was notified to the Ethics Committee at IOV-IRCCS, Padova, Italy on January 2013. The approval to collect and analyze blood samples at the Sahlgrenska University Hospital, Göteborg, Sweden was obtained from the Regional Ethics Board of Västra Götaland, Sweden. Whole blood samples were collected in EDTA-coated tubes. The tubes were centrifuged (2,500 g for 15 minutes at 4° C.) and the plasma extracted and collected in a separate tube. Urine were collected in polypropilene tubes. The samples were stored at −80° C. until they were shipped for analysis in dry ice. The present study was carried out with compliance to the regulations of local Human Ethics Research Committee at the IOV-IRCCS, Padova, Italy.

Glycosaminoglycan Profile Determination

Sample preparation including extraction and purification steps were performed as previously described by Volpi and Maccari 2005[1 and 2] and Coppa et al., 2011), while sample GAGs separation and quantification were performed as described in (Volpi et al., 2014; Volpi and Linhardt, 2010).

Briefly, to extract the GAGs, 500 µl of sample was lyophilized, reconstituted with 1 ml of a 20-mM TRIS-Cl buffer pH 7.4 and treated with protease (Proteinase K from Tritirachium album [E.C. 3.4.21.64], >500 units ml_1 from Sigma-Aldrich) at 60° C. for 12 h. After boiling for 10 min, centrifugation and filtration on 0.45-µm filters, the filtrate was lyophilized. The powder was dissolved in 1 ml of distilled water by prolonged mixing. After centrifugation at 5000 g for 15 min, 0.2 ml of 20% trichloro-acetic acid was added to the supernatant. After 2 h at 4° C., the mixture was centrifuged at 5000 g for 15 min, and the supernatant was recovered and lyophilized. After solubilization in 0.4 ml of bidistilled water and centrifugation at 10 000 g for 10 min, the supernatant was collected and further analysed. To purify the GAGs, after reconstitution with 500 µl 10 mM NaCl, sample GAGs were further purified on anion-exchange resin (QAE Sephadex A-25). After centrifugation at 10,000×g for 5 min, the supernatant was applied to a column (1 cm×4 cm) packed with about 3 ml of resin previously equilibrated with 10 mM NaCl. After washing the resin with 20 ml of 10 mM NaCl, 10 ml of 2.5 M NaCl were added. Fifty milliliters of ethanol were added to the eluate (10 ml) and stored at −20° C. for 24 h. After centrifugation at 5000×g for 15 min, the pellet was dried at 60° C. for 12 h. After reconstitution with 80 µl of 50 mM ammonium acetate pH 8.0, the material was treated with 20 µl of chondroitinase ABC at 37° C. for 12 h. To separate and quantify the GAGs, after boiling for 5 min, the samples were injected in HPLC with both post-column derivatization and fluorimetric detection and on-line electrospray ionization mass spectrometry (ESI-MS).

Eighteen independent GAG properties were measured in each sample (either plasmatic or urinary): CS concentration, HS concentration, and fractions of disaccharide composition for both CS and HS. The charge is the sum over all sulfated disaccharide fractions. Principal component analysis was performed on available GAG properties for three cases: only plasmatic, only urinary, or both plasmatic and urinary (combined). Principal component analysis was implemented using R-package ade4 (centering was performed by the mean).

Bio-Marker Design

To design the markers in the only plasmatic or in the only urinary case, we used Lasso penalized logistic regression (Tibshirani, 1996) with leave-one-out cross-validation to select those GAG properties that are most predictive of the clinical outcome (i.e. mccRCC vs. healthy) at the optimal Lasso penalty value. This was calculated using the glmnet R-package as the penalty value for which the cross-validation error was within 1 standard error of the minimum. The markers were built as the ratio between the sum of the GAG properties robustly predictive of mccRCC over the sum of the GAG properties robustly predictive of healthy state. Each property value was normalized using the respective regression coefficient (rounded to the nearest rational number). The marker for the combined case was taken as the mean of the so-designed plasmatic and urinary markers. The highest density interval (HDI) for the mean difference in marker scores between mccRCC vs. healthy was calculated using Bayesian estimation under the following assumptions: scores are sampled from a t-distribution of unknown and to be estimated normality (i.e. degrees of freedom); high uncertainty on the prior distributions; the marginal distribution is well approximated by a Markov chain Monte Carlo sampling with no thinning and chain length equal to 100, 000. The estimation was performed using BEST R-package (the above assumptions are reflected by the default parameters). Bayesian estimation was preferred over the widely used t-test since it provides a robust and reliable estimation of mean difference even under uncertainty of the underlying score distribution for the two groups (that is the case when the number of samples is limited).

Accuracy Metrics

For each marker (plasma, urine, or combined), we evaluated its performance in the binary classification of a sample as either mccRCC or healthy at varying threshold scores by deriving the receiver-operating-characteristic (ROC) curves. We measured the accuracy of each marker as the area under the curve (AUC) of its ROC curve (AUC is 1 for a perfect classifier and 0.5 for a random classifier). We selected as a potential cut-off value for a given marker the score for which the positive predictive value was maximum, i.e. a sample whose marker score is above this cut-off value has the maximum probability of being mccRCC. We assumed a prevalence equal to the proportion of mccRCC samples in each cohort. The ROC curves were calculated using the pROC R-package, while the optimal cut-off using the OptimalCutpoints R-package.

Analysis of Covariance

The analysis of covariance was performed using logistic regression on the clinical outcome (mccRCC vs. control) on selected covariates among those reported in the clinical and dietary information. These covariates were selected using Lasso penalized logistic regression with leave-one-out cross-validation as the most predictive of the clinical outcome at the optimal Lasso penalty value (chosen as described in Marker design). These covariates are age, weekly consumption of pasta and rice, and use of alcohol. Next, we performed logistic regression on the clinical outcome based on the combined score and the four selected covariates. The significance of each coefficient was tested using the Wald z-statistics for the hypothesis that the corresponding parameter is zero. The same procedure was followed to check the effect of systemic therapy as covariate, but using only plasma samples to regress the clinical outcome (since only for such sub-cohort there were enough patients that did not undergo any systemic therapy). In this case, either only one covariate was used to indicate the presence or absence of undergoing therapy, or a second covariate to account for the specific effect of sunitinib was added. Logistic regression was implemented adopting the Firth bias-reduction method using the brglm R-package. The performance of the two alternative models for logistic regression (either combined score+age+weekly consumption of pasta+weekly consumption of rice+use of alcohol; or combined score) was evaluated according to the minimum Kullback-Leibler divergence criterion by calculating the Akaike's information criterion (AIC) for the models and deriving the model probability in terms of AIC weights.

Results

Metabolic Modeling Reveals a Coordinated Regulation of Glycosaminoglycan Biosynthesis Unique to Clear Cell Renal Cell Carcinoma Our recent study suggests that metabolic reprogramming in ccRCC is unique and is likely due to genetic alterations in tumor progression. The exceptionality of metabolic regulation in ccRCC may have important clinical implications as a potential molecular biomarker. Thus, we sought to fully characterize metabolic regulation in ccRCC computationally. We retrieved a large number of gene expression profiles from The Cancer Genome Atlas (TCGA) (481 tumor samples vs. 71 tumor-adjacent normal samples, here simply referred to as non-tumor, and integrated two methods in genome-scale metabolic modeling named Piano (Varemo et al., 2013) and Kiwi (Varemo et al., 2014) to pinpoint deregulation in either metabolic pathways or connected components in the metabolic network of ccRCC, respectively. When we analyzed differential gene expression in ccRCC vs. non-tumor samples using these methods, the analyses returned a previously unreported sub-network of metabolites that comprises precursors of chondroitin and heparan sulfates (FIG. 1A). Chondroitin (CS) and heparan (HS) sulfates are glycosaminoglycans (GAGs) that share a common biosynthetic route in the linkage to the core protein, but thereafter they differ in polymerization: CS repeating disaccharide is constituted by N-acetylgalactosamine and glucuronic acid residues, while HS repeating disaccharide is constituted by N-acetylglucosamine and glucuronic acid residues. In ccRCC, we observed a coordinated regulation of GAG biosynthesis, defined by a substantial up-regulation of most genes specific to CS biosynthesis (11/13), and a concurrent down-regulation of genes specific to HS biosynthesis (8/13), pointing to a relative change in GAG disaccharide composition, sulfation, and chain length in ccRCC (FIG. 1A). We confirmed such coordinated regulation of GAG biosynthesis in two independent datasets that compared gene expression in ccRCC vs. non-tumor samples, with high and significant correlations between expression fold-changes in these studies and the TCGA samples (Pearson correlation coefficient p=0.87-0.89, FIG. 1B).

To evaluate if the coordinated regulation of GAG biosynthesis is also represented at the level of protein expression, we used immunohistochemistry on a ccRCC tissue microarray to detect the presence of three representative proteins characteristic for the pathway (CHPF2 in CS biosynthesis and HS6ST2 and EXTL1 in HS biosynthesis) in ccRCC vs. normal kidney samples (FIG. 2A). In accordance with gene expression changes, CHPF2 displayed strong staining in all tested tumor samples (positive in 21 of 21 samples) and only weak and likely unspecific staining in the kidney proximal tubule cells (0/2); HS6ST2 showed weak or no staining in all tested tumor samples (positive in 0 of 32), while it was detected in both the podocytes in the kidney glomeruli and the endothelial cells of larger vessels (2/2); and EXTL1 was undetected in 96% of the tested tumor samples (positive in 1 of 27), but it stained strongly in the kidney collecting duct cells (2/2) (representative samples in FIG. 2B). Taken together, these results suggest that a coordinated regulation of GAG biosynthesis is a prominent metabolic event occurring exquisitely in the kidney during ccRCC transformation.

Altered Regulation of Glycosaminoglycan Biosynthesis is Exacerbated in Metastasis and it is Detectable in Patients' Urine and Plasma CS and HS have been long implicated in the regulation of angiogenesis, adhesion, invasion, and migration, which are key steps in the metastatic cascade. We extended our differential gene expression analysis to verify whether genes in GAG biosynthesis showed further regulation in ccRCC patients with metastasis. We found that 11 genes involved in GAG biosynthesis were differentially regulated in metastasis, exacerbating the overexpression of CS-associated genes and the repression of HS-associated genes (FIG. 6). This suggests that a coordinated regulation of GAG biosynthesis is an event exacerbated by metastasis. While the assembly of GAG chains takes place intracellularly, the completed proteoglycan is secreted in the extracellular matrix. Hence, all considered, we speculated that not only eventual changes in GAGs due to ccRCC progression might be reflected in kidney-proximal fluids but also that these changes might be easier to detect in metastatic ccRCC (mccRCC) patients.

To verify whether changes in the GAG profile occur in mccRCC and can be measured in accessible body fluids, we recruited a discovery cohort of 50 subjects, consisting of 34 patients with mccRCC and 16 healthy individuals (Table C). Plasma and urine samples were taken from all subjects, except in 21 mccRCC patients for whom only plasma samples were available. CS and HS concentration and their disaccharide compositions were quantified in the samples using liquid chromatography with on-line electrospray ionization mass spectrometry (ESI-MS). In total, 18 independent GAG properties were measured in every fluid sample (note that the GAG charge is the sum of all sulfated disaccharide fractions). In this experiment, the collection of all these data points defines a GAG profile.

We observed remarkable differences between the GAG profiles and in individual GAG properties of mccRCC patients compared with healthy individuals (FIG. 3A and Table A), both in the plasma and in the urine samples. Principal component analysis (PCA) of either the plasma or the urine GAG profile revealed that mccRCC patients clearly separate from healthy individuals (82% and 63% of variance is explained along the first component, respectively, FIG. 3B). These results indicate that mccRCC entails alterations in systemic GAG composition that are markedly distinct from those of healthy individuals.

Design of mccRCC Markers Based on Plasma and Urine GAG Profiles

The changes in the plasma and urine GAG properties and profiles, which are largely attributed to the occurrence of mccRCC, open the opportunity to design accessible markers based on the GAG properties that best distinguish the disease from a healthy state. We utilized Lasso penalized logistic regression (Tibshirani, 1996) with leave-one-out cross-validation to select robust GAG properties that are most predictive of the clinical outcome (i.e., mccRCC vs. healthy). A marker was subsequently designed as a ratio, where the numerator is the sum of the properties associated with mccRCC and the denominator is the sum of the properties associated with the healthy state. Each term was normalized using the regression coefficients. We derived three potential disease markers, based on either plasma or urine or combined measurements:

$$\text{Plasma score} = \frac{[6s\ CS] + CS_{tot}}{\frac{3}{10}\frac{[4s\ CS]}{[6s\ CS]} + [Ns\ HS]}$$

$$\text{Urine score} = \frac{[Ns6s\ Hs] + 60 \cdot \text{Charge } HS}{[4s\ CS]}$$

Combined score = mean (Plasma score, Urine score)

where terms in brackets represent the fraction of the disaccharide for the corresponding GAG (the abbreviations describe different sulfation patterns for CS and HS as per FIG. 3A), $CS_{tot}$ is the total concentration of CS (in μg/mL) and Charge HS is the total fraction of sulfated disaccharides of HS. We then calculated the three scores for each sample and observed that mccRCC samples have recurrently elevated scores with respect to healthy samples (FIG. 4A). We computed significant non-null mean differences in all three scores between the two groups using robust Bayesian estimation. The mean difference was equal to 2.15 for the combined score (95% High Density Interval [HDI] 1.72 to 2.60), 2.49 for the plasma score (95% HDI 1.94 to 3.05), and 0.79 for the urine score (95% HDI 0.52 to 1.06). The performance of the three markers was evaluated using the receiver-operating-characteristic (ROC) curves, and the area under the curve (AUC) was found to be 1 (perfect classifier) in the case of the combined and plasma scores, and 0.966 for the urine score (FIG. 4B, Table B). A straightforward clinical implementation of these markers would be to monitor mccRCC patients after surgery and diagnose response to treatment using a simple accessible test in addition to or in substitution of standard radiological tests. Thus, from each ROC curve, we computed a score cut-off that maximizes the positive predictive value (PPV) of the marker (Table B). Taken together, these findings demonstrate that alterations in plasma and urine GAG composition occurring in mccRCC can be summarized into scores. In turn, these scores accurately distinguished diseased from healthy individuals.

Validation of the mccRCC Markers in an Independent Cohort and in Patients with No Evidence of Disease To validate whether these scores have a reproducible accuracy in an independent cohort, we recruited 27 subjects, consisting of 18 patients with mccRCC and 9 healthy individuals (Table C). Plasma and urine samples were taken from all subjects, except in 11 mccRCC patients for whom only plasma samples were available. We analyzed the three markers for each individual and computed the corresponding scores. The scores were also remarkably higher in mccRCC compared with healthy controls in this validation cohort (FIG. 4C). We computed an AUC value equal to 1 for all three markers (FIG. 4D and Table B). Additionally, the PPV at the previously determined cut-off score ranged 90% for the plasma marker to 100% for the combined and urine markers (Table B). This evidence strongly suggests that the three markers have the potential to indicate the occurrence of mccRCC by means of an accessible analytical test. Nevertheless, a rigorous validation of the test to monitor mccRCC requires the calculation of the scores in subjects previously diagnosed with mccRCC but with no evidence of disease. Therefore, we analyzed the markers and calculated the corresponding scores in a cohort of 8 individuals diagnosed with mccRCC but with no evidence of disease at the time of sampling. We observed a remarkable decrease in the scores from the expected value in mccRCC, even though the accuracy of the classification differed among scores. The accuracy was high for both the plasma and urine scores, where the computed scores were not above the cut-off in 7 of 8 cases and hence 87.5% of the subjects were correctly identified as not bearing mccRCC (FIG. 5). The accuracy was lower for the combined score, with 6 of 8 subjects (75%) correctly classified according to the cut-off. Although only a clinical trial can corroborate a positive correlation between the tumor burden and the scores, these results argue that plasma and urine GAG composition can be used as a robust and accurate diagnostic biomarker for the occurrence of mccRCC.

Analysis of the Predictive Value of mccRCC Markers Accounting for Confounding Factors We sought to identify the extent to which the measured systemic GAG alterations are purely attributable to ccRCC progression, as suggested by the underlying transcriptional regulation, or whether they are also dependent on other confounding factors. Therefore, we gathered clinical and dietary information, which may confound the association of the scores with the clinical outcome, for 33 individuals (17 mccRCC and 16 healthy). As reported in Table C, we observed an uneven distribution of some baseline characteristics, for example gender, pasta consumption and alcohol consumption. Therefore, we tested whether the clinical outcome could be purely inferred by some of the confounding factors rather than by the marker scores. First, we determined the most biased factors between the mccRCC vs.

healthy groups. To this end, we regressed the clinical outcome based on the confounding factors and the combined score using Lasso penalized logistic regression. This analysis selected four potentially relevant confounding factors: age, weekly consumption of pasta and of rice, and use of alcohol. Then, we performed analysis of covariance using logistic regression to test the strength of the association between the clinical outcome and the combined score using the four confounding factors as covariates. Notably, none of the covariates have a significant contribution in the regression of the clinical outcome (p=0.27 to and 0.44). In addition, we calculated that the logistic regression model based solely on the combined score is the most likely (p=99.2%) according to the minimum Kullback-Leibler divergence criterion: the Akaike information criterion for the regression based on the sole combined score is significantly lower than for the regression based also on the four covariates (7.8 vs. 17.5, respectively). A similar conclusion was reached for the plasma score (6.0 vs. 17.9), but not for the urine score (23.0 vs. 17.5), where pasta consumption displayed a significant effect in the regression of the clinical outcome (p=0.03).

Finally, we explored if systemic therapy has an effect on the marker scores given that these are calculated by profiling body fluids. We limited our analysis to the patients for which only plasma samples were collected (and hence we checked solely the effect on the plasma scores) because for this group we noticed a comparable number of treated (n=19) and untreated (n=33) patients. We did not observe any significant correlation between the plasma score and the use of systemic therapy, based on a linear regression of the score on the treatment status of the sample (p=0.518) and the type of treatment (sunitinib vs. other regiments, p=0.508). Overall, these analyses of covariance show that GAG measurements in the form of the proposed scores can robustly predict the occurrence of mccRCC despite baseline and treatment differences across patients. This robustness is likely due to a coordinated regulation of GAG biosynthesis intrinsic to ccRCC progression, which is mirrored at the level of kidney-adjacent fluids.

Discussion

This study reveals that a coordinated regulation of GAG biosynthesis, which features a concurrent up-regulation of the branch leading to CS formation and down-regulation of the branch leading to HS formation, is a prominent event in ccRCC. Additionally, many pathway-associated genes are further up- or down-regulated in metastasis.

Currently, there is no diagnostic biomarker that has entered routine practice for metastatic ccRCC (Jonasch et al., 2012; Moch et al., 2014). At the same time, the metastatic disease is invariably incurable, although rare complete responses were reported in association with oncological targeted therapies with or without metastasectomy. Therefore, it would undoubtedly represent an important clinical advancement if changes in the GAG profile could constitute an indicator of occurrence of the disease. The availability of such a test would be valuable for a number of medical decisions: to monitor ccRCC before and after surgery or systemic treatment; to rule out the relapse of the disease also during a longer period of time after which a patient is typically declared cured; to assess the occurrence of ccRCC in a population at risk, such as genetically predisposed individuals; to ascertain whether a metastasis is due to ccRCC or other neoplasms; and to follow treatment response in mccRCC. In consideration of this, we designed three markers that are distinctive of occurrence of mccRCC, that are calculated based on measurements in accessible fluids, that are predictive of the clinical outcome independently of the here-considered confounding factors, and that, most importantly, are accurate and robust predictors of the disease.

The plasma and urine GAG profiles loosely resemble the expected pattern from the underlying transcriptional regulation, i.e., an increased output of CS with respect to HS in ccRCC. At the same time, the GAG profiles reveal some novel biological insights attributable to the occurrence of this cancer type. The GAG composition in the plasma of healthy individuals is typically not affected by any tissue. Here, we observed a systemic alteration of GAG composition concomitant to metastatic ccRCC. The enrichment of 4s- and 6s-CS and 6s-HS in mccRCC samples is strikingly reminiscent of the GAG composition of lymphocytes. It is therefore tempting to speculate that infiltration of the immune system in mccRCC could lie behind the observed transcriptional regulation in the tumor. In the urine, the GAG composition in healthy individuals is not as well characterized. The alterations here reported in the GAG profiles of mccRCC samples might reflect a progressive damaging of cells in the kidney glomeruli. Collectively, this evidence seems to underscore the importance of alterations in GAGs in the progression of ccRCC. Intriguingly, the uniqueness of these GAG alterations could be exploited to deliver drugs specifically to ccRCC, as recently shown by a study in which cancer was targeted using a GAG binding malaria protein (Salanti et al., 2015).

Thus far, among the major difficulties that have impaired biomarker discovery and its translation in the clinical practice are the detection of targets in accessible samples and the reproducibility of results (Sawyers, 2008). Here, we provide evidence for a plasmatic and/or urinary marker of metastatic ccRCC that is supported by an intensely and consistently regulated biological process in ccRCC samples. We envision that future longitudinal studies that monitor the trend between the tumor load and the test scores may establish these markers for a diverse range of diagnostic tools in the clinical management of ccRCC.

Example 2

Approximately 50% of cases of clear cell renal cell carcinoma (ccRCC), the most common form of kidney cancer, develop metastatic disease, which is usually incurable. In sharp contrast to early diagnosed ccRCC, the median survival of metastatic patients is significantly worse. The introduction of sequential use of tyrosine-kinase inhibitors (sunitinib, pazopanib, sorafenib, axitinib) and mTOR inhibitors (temsirolimus and everolimus) vastly improved the prognosis of metastatic ccRCC, though with large variation in overall survival. These differences highlight the need to identify the critical biological processes underlying ccRCC aggressiveness, as this would allow elucidation of molecular prognostic markers that can identify patients at higher risk and subsequently guide the therapeutic choices.

Using a systems biology approach, we have reported that transcriptional regulation of glycosaminoglycan (GAG) biosynthesis is a prominent event in ccRCC, exacerbated in metastasis, Example 1 and Gatto et al., 2016. We have further demonstrated that this regulation is mirrored by systemic alterations in the subjects' GAG profile, both in urine and plasma samples and we designed a plasma and/or urine score that leverages on this GAG profile. Because of accuracy and minimal invasiveness, GAG profiling is an attractive, novel biomarker for ccRCC and exemplifies a systems biomarker.

The primary goal of the observational study described in this Example was to understand whether GAG profiling (e.g. the novel GAG plasma and/or urine biomarker score) also correlated with (and thus may be used for) the prognosis of ccRCC in the patients enrolled in the study described in Example 1.

Experimental Procedure

Study Design and Patient Selection

This study report was written in compliance with the REMARK guidelines. A prospective and consecutive cohort of ccRCC patients had been enrolled in our previous biomarker study comprising subjects followed at the Instituto Oncologico Veneto, IOV-IRCCS, Padova, Italy. The series was enrolled between January 2013 and June 2015 (Example 1). The patient population considered for the present study included 31 individuals and the inclusion criteria were as follows: (i) a former or current histological diagnosis of clear cell renal cell carcinoma; (ii) any disease stage; (iii) patients either receiving systemic treatment for metastatic disease or on follow-up observation; and (iv) written informed consent, while the exclusion criteria were as follows: (i) non-clear cell subtypes. The assessment of diagnosis was based on clinical examination and on computed tomography, or other radiological assessments at follow-up. Patients could be receiving different types of oncological treatment at the time of enrolment, as we have previously shown that the biomarker score can be independent from use or type of drug treatment (Gatto et al., 2016). The patient follow-up period ended on December 2015 and the median follow-up time (from day of sampling to the event, e.g., death or right censoring) was 2.7 years. All patients in this study were examined routinely every 3-6 months during the follow-up period at the same clinic. All deaths were attributed to metastatic cancer. The present observational study was notified to the Institutional Review Board at IOV-IRCCS, Padova, Italy on January 2013.

Biomarker Determination

The biomarker score was calculated based on plasma and urine samples taken once during patient follow-up. Whole blood samples were collected in EDTA-coated tubes. The tubes were centrifuged (2,500 g for 15 minutes at 4° C.) and the plasma extracted and collected in a separate tube. Urine were collected in polypropilene tubes. The samples were stored at −80° C. until they were shipped for analysis on dry ice. Glycosaminoglycan measurements were conducted using capillary electrophoresis with laser-induced fluorescence, as previously described (Galeotti et al., 2014; Kottler et al., 2013). Based on these measurements, the plasma and urine biomarkers were scored according to the following formula and as reported herein (e.g., page 15):

$$\text{Plasma score} = \frac{[6s\ CS] + CS_{tot}}{\frac{3}{10}\frac{[4s\ CS]}{[6s\ CS]} + [Ns\ HS]}$$

$$\text{Urine score} = \frac{[Ns6s\ Hs] + 60 \cdot \text{Charge } HS}{[4s\ CS]}$$

where [6s CS] represents the fraction of the 6-sulfated chondroitin sulfate, [4s CS] represents the fraction of the 4-sulfated chondroitin sulfate, [Ns6s HS] represents the fraction of the N-sulfated 6-sulfated heparan sulfate, [Ns HS] represents the fraction of the N-sulfated heparan sulfate, $CS_{tot}$ is the total concentration of CS (in μg/mL) and Charge HS is the total fraction of sulfated disaccharides of HS.

Survival Analysis

Survival was calculated as the time (in days) between the date of sampling and the time of the "event." The time of the "event" is defined as right-censoring (e.g., the date of last follow-up without the event) or as the date of death in case of overall survival and the date of progression in case of progression-free survival. Univariate and multivariate survival analyses were performed by fitting a Cox proportional hazard model to estimate the odds-ratio for the variables of interest and a 95% confidence interval. The log-rank statistical test was utilized to determine the significance of the regression. Initial candidate variables were either the plasma score (2 missing data points) or the urine scores (1 missing data point), as continuous variables computed as per the formula above. For each fluid, the scores were also used to dichotomize the patients into two groups, "Low" versus "High" score, where the median score for the former fluid was used as an unbiased cut-off. Kaplan-Meier survival curves were fitted for the two groups and the statistical significance for survival difference was evaluated using the log-rank test. In addition, we also repeated the above analysis, firstly, by excluding patients with no evidence of disease at follow-up (8 patients) and secondly, by further calculating survival as the time (in days) between the date of starting treatment for the metastatic disease and the time of the event.

Further variables were considered for regression of survival using a univariate Cox model as described above: age (continuous, in years), performance status ECOG score (integer, 0 to 4), Furhman grade (categorical, less versus more than II, 4 missing data points), Heng score (categorical, good vs. intermediate, 1 missing data point), and neutrophile-to-lymphocyte ratio (continuous, 2 missing data points). Patients with missing data from the former analysis were omitted. A multivariate Cox model was pre-specified using variables from the univariate analysis that reached statistical significance (missing data were omitted, yielding 27 and 28 patients evaluated for urine or plasma scores, respectively). In addition, we constructed a multivariate Cox model that featured validated prognostic factors: age and performance status. The validity of the proportional hazard assumption was checked using a two-sided t-test between transformed survival time and the scaled Schoenfeld residuals. The sample size was not powered specifically for this study, because no prior knowledge on the prognostic value of the plasma and/or urine score was available for ccRCC, or any related pathology, at the time of design of this pilot study. We checked for severe overfitting by performing internal validation of the univariate and multivariate models using a bootstrapping algorithm (1,000 bootstraps) and observing the change in Somers' D rank correlation statistics in the original datasets as opposed to the test set. The so corrected Somers' D rank correlation statistics is reported as a metric for the predictive discrimination of each individual pre-specified model. Statistical analyses were performed using the packages survival and rms in R programming language, v. 3.2.3. p-values <0.05 were considered significant.

Results

The prospective cohort comprised 31 patients. 23 patients were metastatic and were being treated with either sunitinib or everolimus; 8 patients had a former diagnosis of ccRCC with no evidence of disease at the time of acquisition of blood and urine sample and were thus not treated with antineoplastic drugs. For this cohort, we had calculated the plasma and urine scores in 29 (93%) and 30 (97%) patients respectively. The median score was 0.89 (IQR: 0.33 to 0.96) for plasma and 1.18 (IQR: 0.88 to 1.49) for urine. For each fluid, we classified patients as either "Low" or "High" depending if the biomarker score was below or above the median score, which was chosen a priori as unbiased cut-off (Example 1). We provide a comparison of standard clinicopathologic features between the two groups in Table D.

Kaplan-Meier survival plots for all 31 patients revealed that "Low"-scored patients fared better both in terms of progression-free survival (PFS) and overall survival (OS) than "High" scored patients, both in the case of urine and plasma scores. Notably, the difference was statistically significant in the case of urine scores (log-rank test p=0.0078 for OS and p=3·$10^{-4}$ for PFS, FIG. 9) as well as in the case of OS for plasma scores (p=0.0206 for OS and p=0.0591 for PFS, FIG. 10). When modelled as continuous variables, both scores showed a linear increase in the risk of both PFS and OS, albeit significant only in the case of urine scores (HR: 9.62, 95% CI: 1.66 to 55.82, p=0.011 for OS, HR: 4.29, 95% CI: 1.49 to 12.33, p=0.007 for PFS). Estimates for the univariate analysis are reported in Table E for PFS and Table F for OS.

We repeated the survival analysis above to evaluate two additional scenarios: the correlation between biomarker score and survival in the subset of patients with a current metastatic ccRCC diagnosis (excluding 8 patients with no evidence of disease); and, within this subset, the correlation between the biomarker score and survival calculated from the start of the first systemic therapy. In the first scenario, Kaplan-Meier curves for these patients stratified according to either the urine (FIG. 11A) or the plasma (FIG. 11B) biomarker score underscored a negative association with PFS and OS for "High"-scored patients (FIG. 11, statistically significant in the case of PFS for urine biomarker (log-rank test p=0.0306). As continuous variables, we confirmed a statistically significant negative correlation between urine scores and PFS or OS (HR: 3.63, 95% CI: 1.20 to 10.95, p=0.022 for PFS, HR: 8.40, 95% CI: 1.41 to 49.96, p=0.019 for OS), while results for the plasma scores were not statistically significant (HR: 0.94, 95% CI: 0.30 to 2.90, p=0.912 for PFS, HR: 1.64, 95% CI: 0.49 to 5.45, p=0.420 for OS). In the second scenario, Kaplan-Meier curves for patients stratified according to either the urine or the plasma biomarker score revealed in both cases that "High"-scored patients tended to have worse prognosis even when survival time was calculated from the start date of treatment (FIG. 12; FIG. 12A—urine; FIG. 12B—plasma).

We next evaluated the correlation between survival and other clinical features in ccRCC: age, performance status, tumor grade, Heng group classification, and the neutrophile-to-lymphocyte ratio (Tables E and F). We recovered a significant linear increase in the hazard ratio for OS (but not PFS) with the neutrophile-to-lymphocyte ratio greater than 3 (HR: 5.03, 95% CI: 1.16 to 21.80, p=0.031). A multivariate analysis on the plasma or urine biomarker score adjusted for the neutrophile-to-lymphocyte ratio confirmed that the urine biomarker score is an independent predictor of PFS (HR: 4.62, 95% CI: 1.66 to 12.83, p=0.003) and OS (HR: 10.13, 95% CI: 1.80 to 57.04, p=0.009), while the plasma biomarker score showed a similar trend (Tables E and F). Thus, specified multivariate models were also statistically significant and showed remarkable concordance with survival in the case of urine scores (likelihood ratio test p=0.003 and C=0.832 for OS, p=0.015 and C=0.745 for PFS). Distinct pre-specified multivariate Cox models that analyzed the estimated effects of the plasma or urine score and established prognostic factors in ccRCC (age and performance status) also provided evidence of statistical associations with survival in the case of urine scores (likelihood ratio test p=0.016 for OS, p=0.031 for PFS).

Discussion

Whilst metastatic ccRCC is considered invariably incurable, patients may reach widely different survival rates according to clinical prognostic factors. In addition, rare complete responses have been reported with current antiangiogenic oncological targeted therapies, with or without metastasectomy. Therefore, it is crucial to determine which biological processes underlie the aggressiveness of ccRCC progression, as these could differentiate patients at higher risk and advocate distinct strategies of treatment. In recent years, several molecular prognostic factors have been shown to effectively predict poor prognosis based on altered expression of proteins or small molecules. However, these biomarkers typically comprise one or few molecules, and are hence unlikely to capture the complexity of the key biological processes driving ccRCC aggressiveness. On the contrary, biological processes driving ccRCC aggression merge from the network of interactions of several biomolecules.

As reported herein, we adopted a systems biology approach to identify the importance of glycosaminoglycan (GAG) biosynthesis regulation in ccRCC. We found that the simultaneous measurements of key GAGs in the plasma and urine effectively capture the regulation of this process and validated the diagnostic value of GAG-profile scores, based this novel systems biomarker (Example 1). The former systems biomarker agglomerates measurements at the metabolite level, which represents an alternative layer of biological information with respect to genetic, protein or immunological markers, which have been extensively investigated in search of novel biomarkers for ccRCC (Maroto and Rini, 2014; Maruzzo et al., 2016; Rossi et al., 2012).

As reported herein, we explored the correlation (and thus the utility) of biomarker scores with prognosis or progression- and overall survival in the prospective cohort of ccRCC patients enrolled in our previous study, described in Example 1.

The strength of the association between biomarker scores and survival was enough to reach statistical significance in both plasma and urine when patients were grouped depending on the median score. As a continuous variable, the urine score achieved the strongest correlation with poor survival, in particular for overall survival (univariate HR=4.62 for PFS and 10.13 for OS), even when limited to the sole metastatic patients (univariate HR=3.63 for PFS and 8.40 for OS). In addition, the urine score was independently associated with OS and PFS in the multivariate analysis (multivariate HR=5.38 for PFS and 16.43 for OS). The plasma score, on the other hand, displayed a weaker trend, which was also stronger in the case of overall survival (univariate HR=1.69 for PFS and 2.23 for OS). We conjecture that the plasma score still has prognostic value because patients with extreme scores fared worse than patients with low scores, as demonstrated by the results when subjects were dichotomized based on the median plasma score (log-rank HR=3.26 for PFS and 7.75 for OS). Taken together, these results constitute evidence that both the plasma and urine biomarker scores at the time of sampling could predict prognosis of ccRCC patients, both in terms of OS and PFS, and that there exists a quantitative linear increase of the risk with increasing scores. These findings demonstrate that our novel systems biomarker or GAG scores have not only demonstrated potential as a diagnostic or a screening tool, but also have a role in prognostics.

Current used prognostic factors in ccRCC are predominantly based on clinical parameters. These include composite scoring systems designed to improve the prognostic value of individual factors, such as tumor size or grade (Sun et al., 2011). The Heng group classification adopted in our study is an example of such a system. An inherent disadvantage of the former systems is that prognosis is based on risk groups rather than quantitative prognostic variables. Nevertheless, no prognostic model based on biomarkers have yet been integrated in routine clinical practice. Limited to blood-based biomarkers, promising results were shown in connection with serum VEGF levels (Negrier et al., 2004) (HR=1.19 for PFS and 1.39 for OS), serum amyloid A (Ramankulov et al., 2008) (HR=2.51-2.81 for OS), serum insulin-like growth factor-1 (Rasmuson et al., 2004) (HR=0.62 for OS). It was noted that these biomarkers could suffer from a number of confounding factors that have no tumor origin (Sun et al., 2011). For example, VEGF levels may be derived from damaged platelets, while amyloid A is a renowned marker of trauma and inflammation. Conversely, the increase of GAG levels in ccRCC patients can be a product of the tumor itself (Ucakturk et al., 2016), possibly due to the up-regulation of the GAG biosynthetic pathway (Gatto et al., 2016). The hazard ratios reported herein for the urine score were not only predictors of poor survival in a continuous and independent fashion, but also of much higher magnitude then the above mentioned biomarkers (multivariate HR=5.38 for PFS and 16.43 for OS).

The distribution of GAG scores further appeared to be independent from other prognostic factors such as age, performance score, tumor grade, Heng group classification, and the neutrophile-to-lymphocyte ratio. Since all 8 non metastatic ccRCC patients had low GAG scores (consistent with the notion that the biomarker correlates with disease severity), therefore, we performed additional analysis in which only the 23 patients with metastatic disease were considered. Once more, the GAG scores retained prognostic significance, suggesting that the prognostic role of this biomarker is likely not an expression of the presence of metastatic disease by itself. Finally, even though the samples were not taken at the start of the treatment, but at different times during patient follow-up, the prediction of disease progression or prognosis showed correlation with overall survival since the start of the treatment as well.

The biomarkers described herein have several, likely clinical advantages because the measurements are minimally invasive, which enables dynamic monitoring of the disease.

In conclusion, we report a correlation between the different profiles of plasma and urine GAGs with PFS and OS of patients with ccRCC and these results demonstrate clinical utility of the GAG scores as a prognostic biomarker for subjects with ccRCC. Overall, capturing the complex expression of glycosaminoglycans by means of a non-invasive, systems biomarker can represent a long awaited clinical biomarker for ccRCC.

REFERENCES

Agren, R., Mardinoglu, A., Asplund, A., Kampf, C., Uhien, M., and Nielsen, J. (2014). Identification of anticancer drugs for hepatocellular carcinoma through personalized genome-scale metabolic modeling. Mol Syst Biol 10, 721.

Galeotti, F., Coppa, G. V., Zampini, L., Maccari, F., Galeazzi, T., Padella, L., Santoro, L., Gabrielli, O., and Volpi, N. (2014). Capillary electrophoresis separation of human milk neutral and acidic oligosaccharides derivatized with 2-aminoacridone. Electrophoresis 35, 811-818.

Gatto, F., Volpi, N., Nilsson, H., Nookaew, I., Maruzzo, M., Roma, A., Johansson, M. E., Stierner, U., Lundstam, S., Basso, U., et al. (2016). Glycosaminoglycan Profiling in Patients' Plasma and Urine Predicts the Occurrence of Metastatic Clear Cell Renal Cell Carcinoma. Cell Rep.

Jonasch, E., Futreal, P. A., Davis, I. J., Bailey, S. T., Kim, W. Y., Brugarolas, J., Giaccia, A. J., Kurban, G., Pause, A., Frydman, J., et al. (2012). State of the science: an update on renal cell carcinoma. Mol Cancer Res 10, 859-880.

Kottler, R., Mank, M., Hennig, R., Muller-Werner, B., Stahl, B., Reichl, U., and Rapp, E. (2013). Development of a high-throughput glycoanalysis method for the characterization of oligosaccharides in human milk utilizing multiplexed capillary gel electrophoresis with laser-induced fluorescence detection. Electrophoresis 34, 2323-2336.

Law, C. W., Chen, Y., Shi, W., and Smyth, G. K. (2014). Voom: precision weights unlock linear model analysis tools for RNA-seq read counts. Genome Biol 15, R29.

Maroto, P., and Rini, B. (2014). Molecular biomarkers in advanced renal cell carcinoma. Clin Cancer Res 20, 2060-2071.

Maruzzo, M., Basso, U., Diminutto, A., Roma, A., Zustovich, F., Brunello, A., Fiduccia, P., Banzato, A., Zattoni, F., and Zagonel, V. (2016). Role of dose exposure and inflammatory status in a single center, real-world analysis of sunitinib in patients with metastatic renal cell carcinoma. Future Oncol 12, 909-919.

Moch, H., Srigley, J., Delahunt, B., Montironi, R., Egevad, L., and Tan, P. H. (2014). Biomarkers in renal cancer. Virchows Arch 464, 359-365.

Negrier, S., Perol, D., Menetrier-Caux, C., Escudier, B., Pallardy, M., Ravaud, A., Douillard, J. Y., Chevreau, C., Lasset, C., Blay, J. Y., et al. (2004). Interleukin-6, interleukin-10, and vascular endothelial growth factor in metastatic renal cell carcinoma: prognostic value of interleukin-6—from the Groupe Francais d'Immunotherapie. J Clin Oncol 22, 2371-2378.

Ramankulov, A., Lein, M., Johannsen, M., Schrader, M., Miller, K., Loening, S. A., and Jung, K. (2008). Serum amyloid A as indicator of distant metastases but not as early tumor marker in patients with renal cell carcinoma. Cancer Lett 269, 85-92.

Rasmuson, T., Grankvist, K., Jacobsen, J., Olsson, T., and Ljungberg, B. (2004). Serum insulin-like growth factor-1 is an independent predictor of prognosis in patients with renal cell carcinoma. Acta Oncol 43, 744-748.

Rossi, E., Fassan, M., Aieta, M., Zilio, F., Celadin, R., Bonin, M., Grassi, A., Troiani, L., Basso, U., Barile, C., et al. (2012). Dynamic changes of live/apoptotic circulating tumour cells as predictive marker of response to sunitinib in metastatic renal cancer. Br J Cancer 107, 1286-1294.

Sawyers, C. L. (2008). The cancer biomarker problem. Nature 452, 548-552.

Smyth, G. K. (2004). Linear models and empirical bayes methods for assessing differential expression in microarray experiments. Stat Appl Genet Mol Biol 3, Article3.

Sun, M., Shariat, S. F., Cheng, C., Ficarra, V., Murai, M., Oudard, S., Pantuck, A. J., Zigeuner, R., and Karakiewicz, P. I. (2011). Prognostic factors and predictive models in renal cell carcinoma: a contemporary review. Eur Urol 60, 644-661.

Tibshirani, R. (1996). Regression shrinkage and selection via the Lasso. Journal of the Royal Statistical Society Series B-Methodological 58, 267-288.

Ucakturk, E., Akman, O., Sun, X., Baydar, D. E., Dolgun, A., Zhang, F., and Linhardt, R. J. (2016). Changes in composition and sulfation patterns of glycoaminoglycans in renal cell carcinoma. Glycoconj J 33, 103-112.

Varemo, L., Gatto, F., and Nielsen, J. (2014). Kiwi: a tool for integration and visualization of network topology and gene-set analysis. BMC Bioinformatics 15, 408.

Varemo, L., Nielsen, J., and Nookaew, I. (2013). Enriching the gene set analysis of genome-wide data by incorporating directionality of gene expression and combining statistical hypotheses and methods. Nucleic Acids Res 41, 4378-4391.

Volpi, N., Galeotti, F., Yang, B., and Linhardt, R. J. (2014). Analysis of glycosaminoglycan-derived, precolumn, 2-aminoacridone-labeled disaccharides with LC-fluorescence and LC-MS detection. Nat Protoc 9, 541-558.

Volpi, N., and Linhardt, R. J. (2010). High-performance liquid chromatography-mass spectrometry for mapping and sequencing glycosaminoglycan-derived oligosaccharides. Nat Protoc 5, 993-1004.

Volpi N and Maccari F. (2005[1]). Glycosaminoglycans composition of the largefreshwater mollusc bivalve Anodonta anodonta. Biomacromolecules 6, 3174-3180.

Volpi N and Maccari F (2005[2]). Microdetermination of chondroitin sulfate in normal human plasma by fluorophore-assisted carbohydrate electrophore-sis (FACE). Clin Chim Acta 356, 125-133.

Coppa G V, Gabrielli O, Buzzega D, Zampini L, Galeazzi T, Maccari F, Bertino E, Volpi N (2011). Composition and structure elucidation of human milk glycosaminoglycans. Glycobiology 21, 295-303.

TABLE A

A metric of statistical confidence that any individual GAG property (CS, HS or HA levels, individual disaccharide compositions, and charge HS or charge CS) displays a significant and practically appreciable alteration between mccRCC and healthy samples was calculated. An alteration was defined as significant and practically appreciable if the difference in means between case and control falls within a so-called Region Of Practical Equivalence in less than 5% of all possible statistical distributions that can fit the data relative to a measurement. Table A shows a summary of the results and shows the mean value for GAG properties as measured in mccRCC vs. healthy subjects plasma or urine and Bayesian estimation for the statistical significance of the mean difference (% in ROPE, Region Of Practical Equivalence, where a % in ROPE >5 indicates that random distributions of values for the two groups have a practically equivalent mean in more than 5% of the cases, and it is therefore not significant).

Table A also shows results where certain ratios of individual types of disaccharide composition have been calculated. 4s.6s CS is the ratio of 4s CS to 6s CS. 6s.0s CS is the ratio of 6s CS to 0s CS (unsulfated CS). 4s.0s CS is the ratio of 4s CS to 0s CS (unsulfated CS).

| Feature | Mean mccRCC | Mean Healthy | ROPE threshold | % in ROPE |
|---|---|---|---|---|
| 0s_CS_plasma | 75.00 | 81.92 | 4.10 | 5.03 |
| 2s_CS_plasma | 0.04 | 0.02 | 0.00 | 1.22 |
| 6s_CS_plasma | 1.99 | 0.33 | 0.02 | 0.00 |
| 4s_CS_plasma | 22.62 | 17.62 | 0.88 | 0.30 |
| 2s6s_CS_plasma | 0.08 | 0.01 | 0.00 | 0.00 |
| 2s4s_CS_plasma | 0.02 | 0.01 | 0.00 | 0.06 |
| 4s6s_CS_plasma | 0.09 | 0.02 | 0.00 | 0.00 |
| Tris_CS_plasma | 0.01 | 0.01 | 0.00 | 8.58 |
| 4s.6s_CS_plasma | 18.28 | 69.62 | 3.48 | 0.00 |
| 6s.0s_CS_plasma | 0.03 | 0.00 | 0.00 | 0.00 |
| 4s.0s_CS_plasma | 0.31 | 0.22 | 0.01 | 0.07 |
| Charge_CS_plasma | 0.25 | 0.18 | 0.01 | 0.03 |
| Tot_HA_plasma | 0.08 | 0.11 | 0.01 | 4.91 |
| Tot_CS_plasma | 5.71 | 5.40 | 0.27 | 32.91 |
| Tris_HS_plasma | 0.51 | 0.33 | 0.02 | 5.15 |
| Ns6s_HS_plasma | 1.81 | 1.38 | 0.07 | 8.20 |
| Ns2s_HS_plasma | 1.01 | 0.66 | 0.03 | 2.82 |
| Ns_HS_plasma | 4.44 | 15.84 | 0.79 | 0.00 |
| 2s6s_HS_plasma | 1.21 | 1.05 | 0.05 | 10.09 |
| 6s_HS_plasma | 6.39 | 6.81 | 0.34 | 25.47 |
| 2s_HS_plasma | 4.09 | 5.16 | 0.26 | 10.02 |
| 0s_HS_plasma | 78.71 | 64.99 | 3.25 | 0.47 |
| Charge_HS_plasma | 0.28 | 0.42 | 0.02 | 1.92 |
| Tot_HS_plasma | 0.07 | 0.05 | 0.00 | 1.60 |
| 0s_CS_urine | 56.43 | 34.91 | 1.75 | 0.01 |
| 2s_CS_urine | 0.08 | 0.08 | 0.00 | 14.98 |
| 6s_CS_urine | 14.61 | 21.56 | 1.08 | 0.90 |
| 4s_CS_urine | 26.98 | 40.53 | 2.03 | 0.00 |
| 2s6s_CS_urine | 0.47 | 0.61 | 0.03 | 9.08 |
| 2s4s_CS_urine | 0.34 | 0.46 | 0.02 | 5.30 |
| 4s6s_CS_urine | 0.88 | 1.18 | 0.06 | 5.92 |
| Tris_CS_urine | 0.02 | 0.04 | 0.00 | 3.42 |
| 4s.6s_CS_urine | 2.31 | 2.01 | 0.10 | 16.35 |
| 6s.0s_CS_urine | 0.31 | 0.74 | 0.04 | 0.09 |
| 4s.0s_CS_urine | 0.49 | 1.26 | 0.06 | 0.00 |
| Charge_CS_urine | 0.44 | 0.65 | 0.03 | 0.01 |
| Tot_HA_urine | 0.11 | 0.06 | 0.00 | 3.64 |
| Tot_CS_urine | 1.99 | 0.81 | 0.04 | 0.29 |
| Tris_HS_urine | 0.86 | 0.39 | 0.02 | 0.34 |
| Ns6s_HS_urine | 2.13 | 1.15 | 0.06 | 0.08 |
| Ns2s_HS_urine | 3.17 | 1.41 | 0.07 | 0.02 |
| Ns_HS_urine | 18.80 | 12.37 | 0.62 | 0.47 |
| 2s6s_HS_urine | 0.93 | 0.96 | 0.05 | 19.79 |
| 6s_HS_urine | 11.45 | 6.82 | 0.34 | 0.19 |
| 2s_HS_urine | 5.21 | 3.63 | 0.18 | 4.55 |
| 0s_HS_urine | 55.58 | 71.79 | 3.59 | 0.06 |
| Charge_HS_urine | 0.54 | 0.33 | 0.02 | 0.00 |
| Tot_HS_urine | 0.25 | 0.11 | 0.01 | 0.20 |

Table A also shows results where certain ratios of individual types of disaccharide composition have been calculated. 4s.6s CS is the ratio of 4s CS to 6s CS. 6s.0s CS is the ratio of 6s CS to 0s CS (unsulfated CS). 4s.0s CS is the ratio of 4s CS to 0s CS (unsulfated CS).

TABLE B

Measures of accuracy for GAG-based markers in the prediction of the clinical outcome (mccRCC vs. healthy) for the discovery and validation cohorts at the optimal cut-off score (as calculated in the discovery cohort).

|  | AUC | Optimal cut-off score | Accuracy | Specificity | Sensitivity | Negative predictive value | Positive predictive value |
|---|---|---|---|---|---|---|---|
| Discovery cohort | | | | | | | |
| Combined marker | 1 | 0.616 | 100% | 100% | 100% | 100% | 100% |
| Plasma marker | 1 | 0.234 | 100% | 100% | 100% | 100% | 100% |
| Urine marker | 0.966 | 1.133 | 93.1% | 100% | 84.6% | 88.9% | 100% |
| Validation cohort | | | | | | | |
| Combined marker | 1 | — | 100% | 100% | 100% | 100% | 100% |
| Plasma marker | 1 | — | 92.6% | 100% | 77.8% | 100% | 90% |
| Urine marker | 1 | — | 93.7% | 100% | 85.7% | 90% | 100% |

TABLE C

Clinical data for the discovery (n = 50) and validation (n = 27) cohorts. All results are presented as medians ($25^{th}$, $75^{th}$ percentile) or percent. Missing values were omitted.

|  | mccRCC (n = 34) | Healthy (n = 16) | mccRCC (n = 18) | Healthy (n = 9) |
|---|---|---|---|---|
| Cohort characteristics | | | | |
| Class | Discovery | Discovery | Validation | Validation |
| Both plasma and urine samples | 13 | 16 | 7 | 9 |
| Only plasma samples | 21 | 0 | 11 | 0 |
| Baseline characteristics | | | | |
| Age [years] | 64.6 (59.2-70.5) | 62.7 (57.6-65) | 56.1 (50.7-64.6) | 55.2 (42.2-64.3) |
| Female | 23.1% | 62.5% | 14.3% | 44.4% |
| Caucasian | 100% | 100% | 100% | 100% |
| BMI [kg/m$^2$] | 26.1 (23.7-26.7) | 25.7 (22.8-29.1) | 23.1 (22.3-28.8) | 23.5 (21.7-25.8) |
| Current oncological therapy | | | | |
| None | 64.7% | 100% | 61.1% | 100% |
| Sunitinib | 20.6% | 0% | 27.8% | 0% |
| Other antineoplastic agents | 14.7% | 0% | 11.1% | 0% |
| Lifestyle characteristics | | | | |
| Physical exercise [h/week] | 2 (2-3.5) | 3 (2-6) | 3 (3-4.75) | 4 (3-7) |
| Bread consumption [servings/week] | 10 (7-14) | 10 (6.25-14.5) | 14 (12-14) | 7 (4-7) |
| Pizza consumption [servings/week] | 1 (0.5-1) | 0 (0-0) | 1 (0.25-1) | 0 (0-1) |
| Pasta consumption [servings/week] | 7 (5-7) | 1 (0.5-1) | 7 (5-7) | 2 (0-3) |
| Rice consumption [servings/week] | 3 (2-3) | 1 (1-2) | 2 (1.5-3) | 1 (1-1) |
| Alcohol consumers | 23.1% | 87.5% | 71.4% | 100% |
| Fiber consumers | 23.1% | 50% | 57.1% | 66.7% |
| Smoking habits | | | | |
| Never smokers | 61.5% | 56.25% | 71.4% | 66.7% |
| Ex smokers | 38.5% | 37.5% | 28.6% | 33.3% |
| Smokers | 0% | 6.25% | 0% | 0% |

TABLE D

Clinicopathological features in the prospective cohort in all patients. Stratified according to "Low" and "High" biomarker score in urine or plasma. The distributions are summarized as median and interquantile ranges in brackets.

| Factors | All N = 31 | Stratified upon plasma score | | Stratified upon urine score | |
|---|---|---|---|---|---|
| | | Low (N = 15) | High (N = 15) | Low (N = 14) | High (N = 15) |
| Age | 65 [58-77] | 67 [61-80] | 63 [56-74] | 65 [56-74] | 65 [58-77] |
| Gender | | | | | |
| Female | 9 | 7 | 2 | 6 | 3 |
| Male | 22 | 8 | 13 | 8 | 12 |

TABLE D-continued

Clinicopathological features in the prospective cohort in all patients. Stratified according to "Low" and "High" biomarker score in urine or plasma. The distributions are summarized as median and interquantile ranges in brackets.

| Factors | All N = 31 | Stratified upon plasma score | | Stratified upon urine score | |
|---|---|---|---|---|---|
| | | Low (N = 15) | High (N = 15) | Low (N = 14) | High (N = 15) |
| BMI | 23.6 [22.5-26.7] | 23.2 [23.1-24.5] | 26.1 [22.3-28.1] | 23.0 [20.3-23.9] | 26.1 [23.3-28.0] |
| Smoking habits | | | | | |
| Never smoker | 18 | 9 | 8 | 8 | 9 |
| Ex-smoker | 8 | 1 | 7 | 1 | 6 |
| Primary neoplastic disease | | | | | |
| Metastatic ccRCC | 23 | 7 | 15 | 6 | 15 |
| NED | 8 | 8 | 0 | 8 | 0 |
| Tumor stage | | | | | |
| T1/T1a/T1b | 9 | 7 | 2 | 7 | 2 |
| T2/T2a | 10 | 5 | 5 | 3 | 6 |
| T3> | 9 | 2 | 6 | 3 | 5 |
| N0 | 16 | 9 | 7 | 8 | 8 |
| N1 | 1 | 0 | 1 | 0 | 1 |
| NX | 14 | 6 | 6 | 6 | 6 |
| Tumor grade | | | | | |
| Grade 2 | 14 | 7 | 6 | 5 | 9 |
| Grade 3 | 9 | 4 | 5 | 3 | 5 |
| Grade 4 | 4 | 2 | 2 | 4 | 0 |
| Performance score | | | | | |
| 0 | 18 | 10 | 8 | 10 | 7 |
| 1 | 13 | 5 | 7 | 4 | 8 |
| Heng classification | | | | | |
| Good | 15 | 10 | 5 | 8 | 6 |
| Intermediate | 15 | 4 | 10 | 5 | 9 |
| Neutrophile-to-lymphocite | | | | | |
| <3 | 24 | 10 | 13 | 10 | 13 |
| >=3 | 5 | 3 | 2 | 2 | 2 |
| Biomarker score | — | 0.25 [0.14-0.67] | 1.37 [1.10-1.74] | 0.75 [0.54-1.10] | 1.49 [1.24-1.87] |

TABLE E

Hazard ratio (HR) for clinical factors in the progression-free survival of metastatic clear cell renal cell carcinoma. The cohort size is 31 patients, missing data are omitted from this count.

| Factors | N [n progr.] | Univariate | | | Multivariate | | |
|---|---|---|---|---|---|---|---|
| | | HR | 95% CI | p | HR | 95% CI | p |
| Age | 29 | 0.98 | 0.94-1.03 | 0.600 | | | |
| Tumor grade | | | | | | | |
| Grade 2 | 14 [7] | 1 | | | | | |
| Grade >2 | 13 [4] | 0.39 | 0.11-1.41 | 0.393 | | | |
| Performance score | | | | | | | |
| 0 | 18 [6] | 1 | | | | | |
| 1 | 13 [7] | 2.26 | 0.75-6.77 | 0.146 | | | |

TABLE E-continued

Hazard ratio (HR) for clinical factors in the progression-free survival of metastatic clear cell renal cell carcinoma. The cohort size is 31 patients, missing data are omitted from this count.

| Factors | N [n progr.] | Univariate HR | 95% CI | p | Multivariate HR | 95% CI | p |
|---|---|---|---|---|---|---|---|
| Heng classification | | | | | | | |
| Good | 11 [6] | 1 | | | | | |
| Intermediate | 14 [7] | 0.84 | 0.28-2.53 | 0.761 | | | |
| Neutrophyle-to-lymphocyte | | | | | | | |
| NLR <3 | 20 [10] | 1 | | | | | |
| NLR >=3 | 4 [3] | 2.49 | 0.68-9.20 | 0.169 | 6.92 | 1.09-44.03 | 0.040 |
| Urine biomarker score | 29 | 4.62 | 1.66-12.83 | 0.003 | 5.38 | 1.65-17.57 | 0.005 |
| Plasma biomarker score | 30 | 1.69 | 0.71-4.01 | 0.232 | | | |

TABLE F

Hazard ratio (HR) for clinical factors in the overall survival of metastatic clear cell renal cell carcinoma. The cohort size is 31 patients, missing data are omitted from this count.

| Factors | N [n death] | Univariate HR | 95% CI | p | Multivariate HR | 95% CI | p |
|---|---|---|---|---|---|---|---|
| Age | 29 | 0.98 | 0.94-1.03 | 0.508 | | | |
| Tumor grade | | | | | | | |
| Grade 2 | 14 [10] | 1 | | | | | |
| Grade >2 | 13 [3] | 0.85 | 0.17-4.26 | 0.844 | | | |
| Performance score | | | | | | | |
| 0 | 18 [7] | 1 | | | | | |
| 1 | 13 [6] | 2.06 | 0.57-7.42 | 0.268 | | | |
| Heng classification | | | | | | | |
| Good | 11 [3] | 1 | | | | | |
| Intermediate | 14 [7] | 2.01 | 0.52-7.79 | 0.314 | | | |
| Neutrophyle-to-lymphocyte | | | | | | | |
| NLR <3 | 20 [7] | 1 | | | | | |
| NLR >=3 | 4 [3] | 4.95 | 1.15-21.28 | 0.032 | 17.77 | 1.58-200.4 | 0.020 |
| Urine biomarker score | 29 | 10.13 | 1.80-57.04 | 0.009 | 16.43 | 2.07-130.5 | 0.008 |
| Plasma biomarker score | 30 | 2.23 | 0.79-6.25 | 0.127 | | | |

TABLE G

Hazard ratio (HR) for individual glycosaminoglycan properties in the progression-free survival of clear cell renal cell carcinoma. The cohort size is 31 patients (missing data omitted)

| Glycosaminoglycan property | HR | p |
|---|---|---|
| 0s_CS_urine | 1.0469 | 0.0357 |
| 2s_CS_urine | 0.0025 | 0.1495 |
| 6s_CS_urine | 0.9306 | 0.0946 |
| 4s_CS_urine | 0.8891 | 0.0159 |
| 2s6s_CS urine | 0.2371 | 0.1967 |
| 2s4s_CS_urine | 0.1841 | 0.2626 |
| 4s6s_CS_urine | 0.8107 | 0.6706 |
| Tris_CS_urine | 0.0015 | 0.3156 |
| 4s.6s_CS_urine | 1.1950 | 0.5146 |
| 6s._0S_CS_urine | 0.1512 | 0.1344 |
| 4s._0S_CS_urine | 0.1153 | 0.0790 |
| Charge_CS_urine | 0.0110 | 0.0375 |
| Total_HA_urine | 334.5807 | 0.0024 |
| Total_CS_urine | 1.1752 | 0.0014 |
| 0s_CS_plasma | 1.3162 | 0.0378 |
| 2s_CS_plasma | 0.0000 | 0.0803 |
| 6s_CS_plasma | 1.3189 | 0.1488 |
| 4s_CS_plasma | 0.6753 | 0.0106 |
| 2s6s_CS_plasma | 0.0000 | 0.2428 |
| 2s4s_CS_plasma | 0.0000 | 0.1853 |
| 4s6s_CS_plasma | 0.0017 | 0.5139 |
| Tris_CS_plasma | 0.0000 | 0.0889 |
| 4s.6s_CS_plasma | 0.7920 | 0.1493 |
| 6s.0s_CS_plasma | 315339826.9335 | 0.2129 |
| 4s.0s_CS_plasma | 0.0000 | 0.0141 |
| Charge_CS_plasma | 0.0000 | 0.0470 |
| Total_HA_plasma | 4540.3161 | 0.0292 |
| Total_CS_plasma | 1.3780 | 0.0835 |

TABLE G-continued

Hazard ratio (HR) for individual glycosaminoglycan properties in the progression-free survival of clear cell renal cell carcinoma. The cohort size is 31 patients (missing data omitted)

| Glycosaminoglycan property | HR | p |
|---|---|---|
| Tris_HS_urine | 1.2268 | 0.2959 |
| Ns6s_HS_urine | 0.8547 | 0.3981 |
| Ns2s_HS_urine | 1.5877 | 0.0496 |
| Ns_HS_urine | 1.2131 | 0.0078 |
| 2s6s_HS_urine | 0.9467 | 0.7706 |
| 6s_HS_urine | 1.0524 | 0.4142 |
| 2s_HS_urine | 0.9243 | 0.3746 |
| 0s_HS_urine | 0.9154 | 0.0567 |
| Charge_HS_urine | 1319.2376 | 0.0546 |
| Total_HS_urine | 1.9800 | 0.0031 |
| Tris_HS_plasma | 0.8720 | 0.5082 |
| Ns6s_HS_plasma | 0.7903 | 0.3807 |
| Ns2s_HS_plasma | 1.0687 | 0.7035 |
| Ns_HS_plasma | 0.9351 | 0.3291 |
| 2s6s_HS_plasma | 0.9870 | 0.9460 |
| 6s_HS_plasma | 1.0826 | 0.4860 |
| 2s_HS_plasma | 0.9070 | 0.4281 |
| 0s_HS_plasma | 1.0516 | 0.3106 |
| Charge_HS_plasma | 0.0678 | 0.3792 |
| Total_HS_plasma | 10.1842 | 0.8744 |

TABLE H

Hazard ratio (HR) for individual glycosaminoglycan properties in the overall survival of clear cell renal cell carcinoma. The cohort size is 31 patients (missing data omitted)

| Glycosammoglycan property | HR | p |
|---|---|---|
| 0s_CS_urine | 1.064 | 0.057 |
| 2s_CS_urine | 0.000 | 0.058 |
| 6s_CS_urine | 0.909 | 0.103 |
| 4s_CS_urine | 0.829 | 0.028 |
| 2s6s_CS_urine | 0.198 | 0.310 |
| 2s4s_CS_urine | 0.387 | 0.638 |
| 4s6s_CS_urine | 1.309 | 0.680 |
| Tris_CS_urine | 0.001 | 0.470 |
| 4s.6s_CS_urine | 1.227 | 0.594 |
| 6s.0s_CS_urine | 0.029 | 0.120 |
| 4s.0s_CS_urine | 0.017 | 0.101 |
| Charge_CS_urine | 0.002 | 0.062 |
| Total_HA_urine | 72.180 | 0.005 |
| Total_CS_urine | 1.338 | 0.002 |
| 0s_CS_plasma | 1.755 | 0.005 |
| 2s_CS_plasma | 0.000 | 0.093 |
| 6s_CS_plasma | 1.219 | 0.431 |
| 4s_CS_plasma | 0.415 | 0.003 |
| 2s6s_CS_plasma | 0.000 | 0.539 |
| 2s4s_CS_plasma | 0.000 | 0.534 |
| 4s6s_CS_plasma | 0.059 | 0.755 |
| Tris_CS_plasma | 0.000 | 0.112 |
| 4s.6s_CS_plasma | 0.763 | 0.249 |
| 6s.0s_CS_plasma | 36503.447 | 0.608 |
| 4s.0s_CS_plasma | 0.000 | 0.002 |
| Charge_CS_plasma | 0.000 | 0.009 |
| Total_HA_plasma | 81731.527 | 0.020 |
| Total_CS_plasma | 1.385 | 0.167 |
| Tris_HS_urine | 1.477 | 0.084 |
| Ns6s_HS_urine | 0.508 | 0.126 |
| Ns2s_HS_urine | 1.763 | 0.079 |
| Ns_HS_urine | 1.243 | 0.037 |
| 2s6s_HS_urine | 0.830 | 0.542 |
| 6s_HS_urine | 1.072 | 0.402 |
| 2s_HS_urine | 0.921 | 0.496 |
| 0s_HS_urine | 0.921 | 0.156 |
| Charge_HS_urine | 1144.606 | 0.162 |
| Total_HS_urine | 2.361 | 0.006 |
| Tris_HS_plasma | 0.795 | 0.395 |
| Ns6s_HS_plasma | 0.690 | 0.284 |
| Ns2s_HS_plasma | 0.949 | 0.812 |
| Ns_HS_plasma | 0.864 | 0.149 |
| 2s6s_HS_plasma | 0.757 | 0.284 |
| 6s_HS_lasma | 1.119 | 0.427 |
| 2s_HS plasma | 1.080 | 0.602 |
| 0s_HS_plasma | 1.086 | 0.192 |
| Charge_HS_plasma | 0.004 | 0.178 |
| Total_HS_plasma | 79661841.974 | 0.278 |

Example 3

We designed an independent experiment in which the primary endpoint was to further confirm that plasma scores are diagnostic of metastatic ccRCC. The primary endpoint was considered met if the accuracy of the classification based on the previously derived cut-off was equal or above the accuracy reported for the plasma score in the validation cohort of our previous experiment (92.6%).

To this end, we sought to obtain plasma samples from subjects known to have metastatic ccRCC and measured the plasma GAG profile as previously described. Next, we calculated the plasma GAG score in each sample. If the GAG score was above the previously identified cutoff for the plasma score—equal to 0.234—then the subjects from which the sample was taken was classified as having metastatic ccRCC, and vice versa if the score was below the previously identified cutoff.

We therefore performed a retrospective collection of plasma samples from Sahlgrenska University Hospital. The eligibility criteria were the following:

Histological diagnosis of clear cell renal cell carcinoma (ccRCC);
Patients either:
 1. with metastatic disease, untreated; or
 2. with metastatic disease, under systemic treatment In total, 26 unique subjects were enrolled for this study and 40 plasma samples were overall collected, meaning that multiple samples were obtained from the same subject over time. The diagnosis of metastatic ccRCC was confirmed at each time of sampling for all subjects.

Plasma GAG scores were above the previously derived cutoff in 38 of 40 samples (FIG. 13). Given that all samples were taken from subjects with a diagnosis of metastatic ccRCC, the accuracy of the plasma GAG scores was 95%. We conclude that the primary endpoint was met and the that plasma GAG scores are suitable to diagnose metastatic ccRCC.

The invention claimed is:

1. A method of screening for renal cell carcinoma in a subject, said method comprising determining the level and/or chemical composition of one or both of the glycosaminoglycans (GAGs) chondroitin sulfate (CS) and heparan sulfate (HS) in a body fluid sample obtained from said subject,
   wherein said GAGs are subjected to a step of fragmentation or cleavage or digestion by enzyme treatment followed by a step of derivatization, and
   wherein an altered level and/or chemical composition of CS and/or HS in said sample, as determined by analysing GAGs that have been subjected to said enzyme treatment and derivatization, in comparison to a control level and/or chemical composition is indicative of renal cell carcinoma in said subject.

2. The method of claim 1, wherein said determination of the chemical composition comprises determining the level in the sample of one or more GAG properties selected from the group consisting of: one or more of the specific sulfated or unsulfated forms of CS or HS disaccharides, the fraction of sulfated disaccharides of HS out of the total HS disaccharides present (charge HS), the fraction of sulfated disaccharides of CS out of the total CS disaccharides present (charge CS), the total concentration of CS or the total concentration of HS.

3. The method of claim 1, wherein said determination of the chemical composition comprises determining the level in the sample of one or more of the GAG properties selected from the group consisting of: the specific sulfated or unsulfated forms of CS or HS disaccharides selected from the group consisting of: 0s CS, 2s CS, 6s CS, 4s CS, 2s6s CS, 2s4s CS, 4s6s CS, Tris CS, 0s HS, 2s HS, 6s HS, 2s6s HS, Ns HS, Ns2s HS, Ns6s HS, Tris HS, the ratio of 4s CS to 6s CS, the ratio of 6s CS to 0s CS and the ratio of 4s CS to 0s CS; the fraction of sulfated disaccharides of HS out of the total HS disaccharides present (charge HS); the fraction of sulfated disaccharides of CS out of the total CS disaccharides present (charge CS); the total concentration of CS (CS tot); and the total concentration of HS (HS tot).

4. The method of claim 1,
wherein said determination of the chemical composition comprises determining the level in the sample of one or more of the GAG properties selected from the group consisting of: 6s CS, 4s CS, Ns HS, Ns6s HS, the ratio of 4s CS to 6s CS, charge HS and CS total; or
wherein said determination of the chemical composition comprises determining the level in the sample of one or more of the GAG properties selected from the group consisting of: the ratio of 6s CS to 0s CS or the ratio of 4s CS to 0s CS.

5. The method of claim 1 wherein the body fluid sample is a plasma sample and wherein said determination of the chemical composition comprises determining the level in the sample of one or more of the GAG properties selected from the group consisting of: charge CS, CS tot, 2s CS, 6s CS, 4s CS, 2s6s CS, 2s4s CS, 4s6s CS, the ratio of 4s CS to 6s CS, the ratio of 6s CS to 0s CS, the ratio of 4s CS to 0s CS, charge HS, HS tot, 0s HS, Ns HS and Ns2s HS.

6. The method of claim 1 wherein the body fluid sample is a plasma sample and wherein said determination of the chemical composition comprises determining the level in the sample of:
(i) one or more, or all, of the GAG properties: 6s CS, CS tot, the ratio of 4s CS to 6s CS, and Ns HS; or
(ii) one or more, or all, of the GAG properties: 6s CS, CS tot, and the ratio of 4s CS to 6s CS; or
(iii) the ratio of 4s CS to 6s CS; or
(iv) one or more, or all, of the GAG properties: 6s CS, the ratio of 4s CS to 6s CS, Ns HS, and the ratio of 6s CS to 0s CS.

7. The method of claim 1 wherein the body fluid sample is a urine sample and wherein said determination of the chemical composition comprises determining the level in the sample of one or more of the GAG properties selected from the group consisting of: charge CS, CS tot, 0s CS, 6s CS, 4s CS, Tris CS, the ratio of 6s CS to 0s CS, the ratio of 4s CS to 0s CS, charge HS, HS tot, 0s HS, 2s HS, 6s HS, Ns HS, Ns2s HS, Ns6s HS and Tris HS.

8. The method of claim 1 wherein the body fluid sample is a urine sample and wherein said determination of the chemical composition comprises determining the level in the sample of:
(i) one or more, or all, of the GAG properties: Ns6s HS, charge HS, and 4s CS; or
(ii) one or more, or all, of the GAG properties: 4s CS, the ratio of 4s CS to 0s CS, charge CS and 0s HS.

9. The method of claim 1, wherein an increased concentration of CS in said sample and/or an increased concentration of HS in said sample is indicative of RCC in said subject.

10. The method of claim 1, wherein an increased level in said sample of one or more of: Ns2s HS, Ns6s HS, and Tris HS, is indicative of RCC in said subject.

11. The method of claim 2,
wherein said method comprises determining the level of more than one of said GAG properties; or
wherein said method comprises determining the level of two or more, three or more, four or more, or all, of said GAG properties.

12. The method of claim 3, wherein said method comprises determining the level of up to 8, or all 8, of the sulfated and unsulfated CS forms: 0s CS, 2s CS, 6s CS, 4s CS, 2s6s CS, 2s4s CS, 4s6s CS and Tris CS, optionally together with total CS and/or charge CS; and/or wherein said method comprises determining the level of up to 8, or all 8, of the sulfated and unsulfated HS forms: 0s HS, 2s HS, 6s HS, 2s6s HS, Ns HS, Ns2s HS, Ns6s HS and Tris HS, optionally together with total HS and/or charge HS.

13. The method of claim 1, wherein said method is used for diagnosing renal cell carcinoma (RCC), for the prognosis of RCC, for monitoring subjects at risk of the occurrence of RCC, for monitoring the progression of RCC in a subject, for determining the clinical severity of RCC, for predicting the response of a subject to therapy or surgery for RCC, for determining the efficacy of a therapeutic or surgical regime being used to treat RCC, for detecting the recurrence of RCC, or for distinguishing small renal masses suspicious of RCC from other non malignant diseases.

14. The method of claim 1, wherein said renal cell carcinoma (RCC) is stage III or IV RCC, metastatic RCC, or is clear cell RCC.

15. The method of claim 1, wherein said subject is a subject at risk of developing renal cell carcinoma (RCC), or at risk of the occurrence of RCC, or is a subject having or suspected of having RCC.

16. The method of claim 1, wherein said body fluid sample is plasma and/or urine.

17. The method of claim 1, wherein said level or chemical composition of said GAG or GAG property is determined by electrophoresis such as capillary electrophoresis, preferably capillary electophoresis with laser-induced fluorescence detection, or is determined by HPLC and mass spectrometry.

18. The method of claim 2, wherein the levels of one or more of the specific sulfated or unsulfated forms of CS or HS disaccharides are determined, and wherein the GAGs are subjected to a processing step to obtain the disaccharide units for analysis.

19. The method of claim 1, wherein said method further comprises a step of treating renal cell carcinoma (RCC) by therapy or surgery.

20. A method for the prognosis of renal cell carcinoma (RCC) in a subject, said method comprising determining the level and/or chemical composition of one or both of the glycosaminoglycans (GAGs) chondroitin sulfate (CS) and heparan sulfate (HS) in a body fluid sample obtained from said subject, wherein said GAGs are subjected to a step of fragmentation or cleavage or digestion, and wherein an altered level and/or chemical composition of CS and/or HS in said sample in comparison to a control level and/or chemical composition is indicative of prognosis for renal cell carcinoma in said subject.

21. The method of claim 20, wherein said prognosis is in terms of progression-free survival or in terms of overall survival.

22. The method of claim 20, wherein said renal cell carcinoma is clear cell renal cell carcinoma, preferably metastatic clear cell renal cell carcinoma.

23. The method of claim 1, wherein said level and/or chemical composition of said GAG is determined by capillary electrophoresis with laser-induced fluorescence detection or by high performance liquid chromatography-electrospray ionization-mass spectrometry (HPLC ESI-MS).

\* \* \* \* \*